US011866398B2

(12) United States Patent
Li et al.

(10) Patent No.: US 11,866,398 B2
(45) Date of Patent: Jan. 9, 2024

(54) TOTAL SYNTHESIS OF PROSTAGLANDIN J NATURAL PRODUCTS BY STEREORETENTIVE METATHESIS

(71) Applicant: California Institute of Technology, Pasadena, CA (US)

(72) Inventors: Jiaming Li, Pasadena, CA (US); Xu Chen, Pasadena, CA (US); Tonia S. Ahmed, Pasadena, CA (US); Brian M. Stoltz, Pasadena, CA (US); Robert H. Grubbs, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 556 days.

(21) Appl. No.: 17/055,970

(22) PCT Filed: May 14, 2019

(86) PCT No.: PCT/US2019/032259
§ 371 (c)(1),
(2) Date: Nov. 16, 2020

(87) PCT Pub. No.: WO2019/222244
PCT Pub. Date: Nov. 21, 2019

(65) Prior Publication Data
US 2021/0332011 A1 Oct. 28, 2021

Related U.S. Application Data

(60) Provisional application No. 62/803,603, filed on Feb. 11, 2019, provisional application No. 62/671,891, filed on May 15, 2018.

(51) Int. Cl.
*C07C 405/00* (2006.01)
*B01J 23/46* (2006.01)

(52) U.S. Cl.
CPC ....... *C07C 405/0016* (2013.01); *B01J 23/462* (2013.01); *C07C 2601/10* (2017.05)

(58) Field of Classification Search
CPC .. B01J 23/462; C07C 2601/10; C07C 405/00; C07C 405/0016; C07C 45/68; C07C 49/707; C07F 15/0046; C07F 7/188; C07F 7/1892
See application file for complete search history.

(56) References Cited

U.S. PATENT DOCUMENTS

| | | |
|---|---|---|
| 2014/0106960 A1 | 4/2014 | Endo et al. |
| 2015/0051410 A1 | 2/2015 | Wei et al. |
| 2015/0336923 A1 | 11/2015 | Wei et al. |
| 2016/0237056 A1 | 8/2016 | Yiannikouros et al. |
| 2018/0050999 A1 | 2/2018 | Wei et al. |

FOREIGN PATENT DOCUMENTS

| | | |
|---|---|---|
| CN | 103402628 A | 11/2013 |
| JP | 2005-330191 A | 12/2005 |
| JP | 2015-036382 A | 2/2015 |
| JP | 2016-533393 A | 10/2016 |
| WO | 2017/100585 A1 | 6/2017 |
| WO | 2017/165170 A1 | 9/2017 |
| WO | WO2017165170 | * 9/2017 |
| WO | 2019/222244 A1 | 11/2019 |

OTHER PUBLICATIONS

Acharya et al., "Highly efficient total synthesis of Delta12-PGJ2, 15-deoxy-Delta12,14-PGJ2, and their analogues," Tetrahedron, vol. 62, No. 14, Apr. 3, 2006, pp. 3329-3343.
Acharya et al., "Total Synthesis of Delta12-PGJ2, 15-Deoxy-Delta12,14-PGJ2, and Related Compounds," Tetrahedron Letters, vol. 45, No. 6, Feb. 2, 2004, pp. 1199-1202.
Ahmed et al., "Fast-Initiating, Ruthenium-based Catalysts for Improved Activity in Highly E-Selective Cross Metathesis," Journal of the American Chemical Society, vol. 139, No. 4, Jan. 20, 2017, pp. 1532-1537.
Ahmed et al., "Using stereoretention for the synthesis of E-macrocycles with ruthenium-based olefin metathesis catalysts," Chemical Science, vol. 9, No. 14, Mar. 14, 2018, pp. 3580-3583.
Arisetti et al., "Traceless Stereoinduction for the Enantiopure Synthesis of Substituted-2-Cyclopentenones," Organic Letters, vol. 17, No. 1, Dec. 12, 2014, pp. 94-97.
Bai et al., "Total Synthesis of (−)-Spinosyn A via Carbonylative Macrolactonization," Journal of the American Chemical Society, vol. 138, No. 34, Aug. 10, 2016, pp. 10838-10841.
Bickley et al., "Synthesis of Optically Active Prostaglandin-J2 and 15-Deoxy-Delta12,14-prosta-glandin-J2," Synlett, vol. 8, Jan. 2003,pp. 1170-1174.
Brummond et al., "The First Total Synthesis of 15-Deoxy-Delta12,14-prostaglandin J2 and the Unambiguous Assignment of the C14 Stereochemistry," Organic Letters, vol. 6, No. 2, 2004, pp. 149-152.
Cheng-Sánchez et al., "Recent Advances in Total Synthesis via Metathesis Reactions," Synthesis, vol. 50, No. 19, Jul. 18, 2018, pp. 3749-3786.
Corey et al., "Stereo-controlled synthesis of dl-prostaglandins F2.alpha. and E2," Journal of the American Chemical Society, vol. 91, No. 20, Sep. 1, 1969, pp. 5675-5677.
Couturier et al., "A Cyclometalated Aryloxy(chloro) neopentylidenetungsten Complex: A Highly Active and Stereoselective Catalyst for the Metathesis of cis- and trans-2-Pentene, Norbornene, 1-Methyl-norbornene, and Ethyl Oleate," Angewandte Chemie International Edition, vol. 31, No. 5, May 1992, pp. 628-631.
Das et al., "Recent Developments in the Synthesis of Prostaglandins and Analogues," Chemical Reviews, vol. 107, No. 7, Jun. 23, 2007, pp. 3286-3337.
Egger et al., "Total Synthesis of Prostaglandin 15d-PGJ2 and Investigation of its Effect on the Secretion of IL-6 and IL-12," Organic Letters, vol. 17, No. 17, Aug. 24, 2015, pp. 4340-4343.

(Continued)

*Primary Examiner* — Jafar F Parsa
*Assistant Examiner* — Blaine G Doletski
(74) *Attorney, Agent, or Firm* — Faegre Drinker Biddle & Reath LLP

(57) ABSTRACT

This invention relates generally to the synthesis of $\Delta^{12}$-Prostaglandin J product using stereoretentive ruthenium olefin metathesis catalysts supported by dithiolate ligands. $\Delta^{12}$-Prostaglandin J products were generated with excellent selectivity (>99% Z) and in moderate to high/good yields (47% to 80% yield; 58% to 80% yield).

10 Claims, No Drawings

(56) References Cited

OTHER PUBLICATIONS

Endo et al., "Chelated Ruthenium Catalysts for Z-Selective Olefin Metathesis," Journal of the American Chemical Society, vol. 133, No. 22, May 12, 2011, pp. 8525-8527.

Funk, C. D., "Prostaglandins and leukotrienes: advances in eicosanoid biology," Science, vol. 294, No. 5548, Nov. 30, 2001, pp. 1871-1875.

Fürstner, A., "Metathesis in total synthesis," Chemical Communications, vol. 47, No. 23, Apr. 26, 2011, pp. 6505-6511.

Hegde et al., "Delta12-prostaglandin J3, an omega-3 fatty acid-derived metabolite, selectively ablates leukemia stem cells in mice," Blood, vol. 118, No. 26, Dec. 22, 2011, pp. 6909-6919.

Herbert et al., "Z-Selective Cross Metathesis with Ruthenium Catalysts: Synthetic Applications and Mechanistic Implications," Angewandte Chemie International Edition, vol. 54, No. 17, Apr. 20, 2015, pp. 5018-5024.

Hoveyda, A. H., "Evolution of Catalytic Stereoselective Olefin Metathesis: From Ancillary Transformation to Purveyor of Stereochemical Identity," The Journal of Organic Chemistry, vol. 79, No. 11, Apr. 10, 2014, pp. 4763-4792.

International Preliminary Report on Patentability received for PCT Patent Application No. PCT/US2019/032259, dated Jul. 1, 2020, 7 pages.

Johns et al., "High Trans Kinetic Selectivity in Ruthenium-Based Olefin Cross-Metathesis through Stereoretention," Organic Letters, vol. 18, No. 4, Feb. 3, 2016, pp. 772-775.

Jung et al., "Toward Perfect Regiocontrol for β-Selective Cyclopolymerization Using a Ru-Based Olefin Metathesis Catalyst," Macromolecules, vol. 51, No. 12, Jun. 7, 2018, pp. 4564-4571.

Keitz et al., "Improved Ruthenium Catalysts for Z-Selective Olefin Metathesis," Journal of the American Chemical Society, vol. 134, No. 1, Nov. 19, 2011, pp. 693-699.

Khan et al., "Readily Accessible and Easily Modifiable Ru-Based Catalysts for Efficient and Z-Selective Ring-Opening Metathesis Polymerization and Ring-Opening/Cross-Metathesis," Journal of the American Chemical Society, vol. 135, No. 28, Jul. 3, 2013, pp. 10258-10261.

Kim et al., "Concise and Enantioselective Total Synthesis of 15-Deoxy-Delta12,14-Prostaglandin J2," The Journal of Organic Chemistry, vol. 75, No. 21, Oct. 8, 2010, pp. 7458-7460.

Koh et al., "Broadly Applicable Z- and Diastereoselective Ring-Opening/Cross-Metathesis Catalyzed by a Dithiolate Ru Complex," Angewandte Chemie International Edition, vol. 53, No. 7, Feb. 10, 2014, pp. 1968-1972.

Koh et al., "High-value alcohols and higher-oxidation-state compounds by catalytic Z-selective cross-metathesis," Nature, vol. 517, No. 7533, Jan. 7, 2015, pp. 181-186.

Koh et al., "Molybdenum chloride catalysts for Z-selective olefin metathesis reactions," Nature, vol. 542, No. 7639, Feb. 2, 2017, pp. 80-85.

Kudva et al., "Evaluation of the Stability, Bioavailability, and Hypersensitivity of the Omega-3 Derived Anti-Leukemic Prostaglandin: Delta 12-Prostaglandin J3," Plos One, vol. 8, No. 12, Dec. 2, 2013, e80622, pp. 1-10.

Lam et al., "Synthesis and Evaluation of Molybdenum and Tungsten Monoaryloxide Halide Alkylidene Complexes for Z-Selective Cross-Metathesis of Cyclooctene and Z-1,2-Dichloroethylene," Journal of the American Chemical Society, vol. 138, No. 48, Nov. 10, 2016, pp. 15774-15783.

Li et al., "Concise Syntheses of delta 12-Prostaglandin J Natural Products via Stereoretentive Metathesis", Journal of the American Chemical Society, vol. 141, Jan. 9, 2019, pp. 154-158.

Montgomery et al., "Stereoretentive Olefin Metathesis: An Avenue to Kinetic Selectivity," Angewandte Chemie International Edition, vol. 56, No. 37, Sep. 4, 2017, pp. 11024-11036.

Nguyen et al., "Kinetically controlled E-selective catalytic olefin metathesis," Science, vol. 352, No. 6285, Apr. 29, 2016, pp. 569-575.

Nicolaou et al., "Synthesis and Biological Investigation of Delta12-Prostaglandin J3 (Delta12-PGJ3) Analogues and Related Compounds," Journal of the American Chemical Society, vol. 138, No. 20, May 12, 2016, pp. 6550-6560.

Nicolaou et al., "Total Synthesis of delta 12-Prostaglandin J3: Evolution of Synthetic Strategies to a Streamlined Process", Chemistry A European Journal. May 17, 2016, vol. 22, pp. 8559-8570.

Nicolaou et al., "Total Synthesis of Delta12-Prostaglandin J3, a Highly Potent and Selective Antileukemic Agent," Angewandte Chemie International Edition, vol. 53, No. 39, Sep. 22, 2014, pp. 10443-10447.

Nicolaou et al., Metathesis Reactions in Total Synthesis, Angewandte Chemie International Edition, vol. 44, No. 29, Jul. 18, 2005, pp. 4490-4527.

Noyori et al., "Prostaglandin Syntheses by Three-Component Coupling. New Synthetic Methods (49)," Angewandte Chemie International Edition, vol. 23, No. 11, Nov. 1984, pp. 847-876.

Pelss et al., Reoptimization of the Organocatalyzed Double Aldol Domino Process to a Key Enal Intermediate and Its Application to the Total Synthesis of Delta12-Prostaglandin J3, Chemistry—A European Journal, vol. 24, No. 38, Jul. 5, 2018, pp. 9542-9545.

Peng et al., "Recent advances in asymmetric total synthesis of prostaglandins," Organic Biomolecular Chemistry, vol. 15, No. 30, Jul. 10, 2017, pp. 6281-6301.

Shen et al., "Kinetically E-selective macrocyclic ring-closing metathesis," Nature, vol. 541, No. 7637, Jan. 9, 2017, pp. 380-385.

Straus et al., "Cyclopentenone prostaglandins: new insights on biological activities and cellular targets," Medicinal Research Reviews, vol. 21, No. 3, May 2001, pp. 185-210.

Ulbrich et al., "Enantioselective synthesis of 4-heterosubstituted cyclopentenones," The Journal of Organic Chemistry, vol. 78, No. 8, Mar. 25, 2013, pp. 4202-4206.

Xu et al., "In Situ Methylene Capping: A General Strategy for Efficient Stereoretentive Catalytic Olefin Metathesis. The Concept, Methodological Implications, and Applications to Synthesis of Biologically Active Compounds," Journal of the American Chemical Society, vol. 139, No. 31, Jul. 27, 2017, pp. 10919-10928.

Yadav et al., "Stereoselective Total Synthesis of the Marine Macrolide Sanctolide A," European Journal of Organic Chemistry, vol. 2015, No. 26, Sep. 2015, pp. 5856-5863.

International Search Report for PCT/US2019/032259 dated Jul. 25, 2019.

Written Opinion of the International Searching Authority for PCT/US2019/032259 dated Jul. 25, 2019.

* cited by examiner

TOTAL SYNTHESIS OF PROSTAGLANDIN J NATURAL PRODUCTS BY STEREORETENTIVE METATHESIS

CROSS-REFERENCE TO RELATED APPLICATIONS

This application is a national stage application (under 35 U.S.C. § 371) of PCT/US2019/032259, filed May 14, 2019, which claims benefit of U.S. Application Nos. 62/671,891, filed May 15, 2018, and 62/803,603, filed Feb. 11, 2019, all of which are incorporated herein by reference in their entirety.

RELATED APPLICATIONS

This application claims the benefit of U.S. Provisional Patent Application No. 62/671,891 filed May 15, 2018, and of U.S. Provisional Patent Application No. 62/803,603 filed Feb. 11, 2019, the contents of which are incorporated herein by reference.

STATEMENT REGARDING FEDERALLY SPONSORED RESEARCH OR DEVELOPMENT

This invention was made with government support under NIH Grant No. GM031332. The U.S. Government has certain rights in the invention.

TECHNICAL FIELD

Prostaglandins are an important class of naturally occurring molecules that are found in mammalian tissues and exhibit a broad range of biological functions and widespread medical applications. [Marks F. and Fürstenberger G. *Prostagandins, Laukotrienes and Other Eicosanoids*; Wiley-Blackwell, 1999. Funk, C. D. Prostaglandins and Leukotrienes: Advances in Eicosanoid Biology. *Science* 2001, 294, 1871-1875.]

Efforts directed toward the synthesis of various prostaglandins has had a profound effect on the development of new strategies and tactics employed in the field of synthetic chemistry, emanating from the seminal studies of Corey beginning in the 1960's. [Corey, E. J.; Weinshenker, N. M.; Schaaf, T. K.; Huber, W. Stereo-Controlled Synthesis of DI-Prostaglandins F2.alpha, and E2. *J. Am. Chem. Soc.* 1969, 91, 5675-5677. Das, S.; Chandrasekhar, S.; Yadav, J. S.; Grée, R. Recent Developments in the Synthesis of Prostaglandins and Analogues. *Chem. Rev.* 2007, 107, 3286-3337. Peng, H.; Chen, F.-E. Recent Advances in Asymmetric Total Synthesis of Prostaglandins. *Org. Biomol. Chem.* 2017, 15, 6281-6301.]

BACKGROUND

The recently discovered $\Delta^{12}$-prostaglandin J family (1), (2), (3) and (4) as shown in FIG. 1, features a unique cross-conjugated dienone motif and appealing anticancer activity. [Straus D. S.; Glass C. K. Cyclopentenone Prostaglandins: New Insights on Biological Activities and Cellular Targets. *Med. Res. Rev.* 2001, 21, 185-210.]

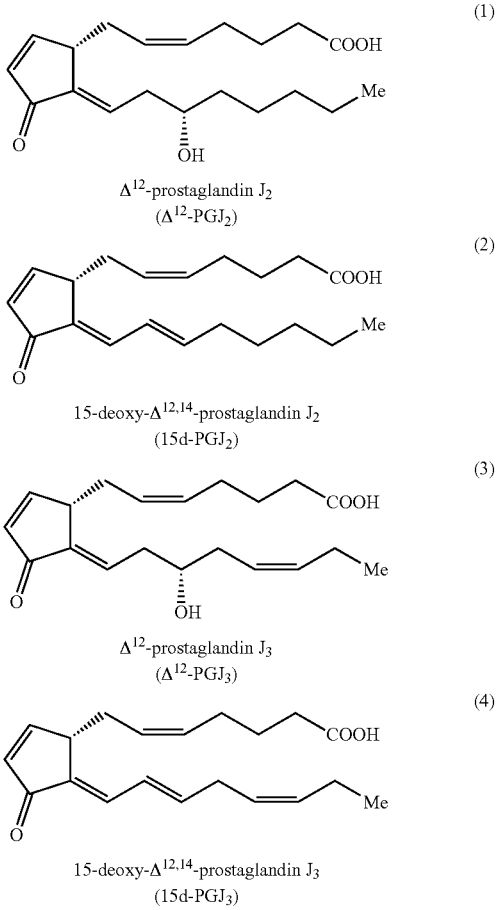

Figure 1. $\Delta^{12}$-Prostaglandin J Natural Products $\Delta^{12}$-PGJ$_3$ (3), for example, was isolated as a secondary metabolite and was shown to selectively induce apoptosis of leukemia stem cells over normal hematopoietic stems cells with high potency. [Hegde, S.; Kaushal. N.; Ravindra K. C.; Chiaro, C.; Hafer, K. T.; Gandhi, U. H.; Thompson, J. T.; van den Heuvel, J. P.; Kennett, M. J.; Hankey, P.; Paulson R. F.; Prabhu K. S. $\Delta^{12}$-Prostaglandin J$_3$, an Omega-3 Fatty Acid-Derived Metabolite, Selectively Ablates Leukemia Stem Cells in Mice. *Blood* 2011, 118, 6909-6919.]

Studies of its stability, bioavailability, and hypersensitivity make $\Delta^{12}$-PGJ$_3$ an intriguing drug candidate for leukemia treatment. [Kudva, A. K.; Kaushal, N.; Mohinta, S.; Kennett, M. J.; August, A.; Paulson, R. F.; Prabhu, K. S. Evaluation of the Stability, Bioavailability, and Hypersensitivity of the Omega-3 Derived Anti-Leukemic Prostaglandin: $\Delta^{12}$-Prostaglandin J$_3$ *PLOS ONE* 2013, 8, e80622.]

Synthetic efforts toward $\Delta^{12}$-prostaglandin J compounds began in 2003, with a number of syntheses of $\Delta^{12}$-PGJ$_2$ (1) and 15d-PGJ$_2$ (2) reported through various approaches. [Bickley, J. F.; Jadhav, V.; Roberts, S. M.; Santoro, M. G.; Steiner, A.; Sutton, P. W. Synthesis of Optically Active Prostaglandin J$_2$ and 15-Deoxy-$\Delta^{12,14}$ Prostaglandin J$_2$. *Synlett* 2003, 1170-1174. Brummond, K. M.; Sill, P. C.; Chen, H. The First Total Synthesis of 15-Deoxy-$\Delta^{12,14}$-Prostaglandin J$_2$ and the Unambiguous Assignment of the C14 Stereochemistry. *Org. Lett.* 2004, 6, 149-152. Acharya, H. P.; Kobayashi, Y. Total Synthesis of $\Delta^{12}$-PGJ$_2$, 15-Deoxy-$\Delta^{12,14}$-PGJ$_2$, and Related Compounds. *Tetrahedron*

Lett. 2004, 45, 1199-1202. Acharya, H. P.; Kobayashi, Y. Highly Efficient Total Synthesis of $\Delta^{12}$-PGJ$_2$, 15-Deoxy-$\Delta^{12,14}$-PGJ$_2$, and Their Analogues. *Tetrahedron* 2006, 62, 3329-3343. Kim, N.-J.; Moon, H.; Park. T.; Yun, H.; Jung, J.-W.; Chang, D.-J.; Kim, D.-D.; Suh, Y.-G. Concise and Enantioselective Total Synthesis of 15-Deoxy-$\Delta^{12,14}$-Prostaglandin J$_2$ *J. Org. Chem.* 2010, 75, 7458-7460. Egger, J.; Fischer, S.; Bretscher, P.; Freigang, S.; Kopf, M.; Carreira, E. M. Total Synthesis of Prostaglandin 15d-PGJ$_2$ and Investigation of Its Effect on the Secretion of IL-6 and IL-12. *Org. Lett.* 2015, 17, 4340-4343.]

Elegant contributions to the total synthesis of $\Delta^{12}$-PGJ$_3$. (3) were reported by Nicolaou and co-workers and more recently by the Aggarwal group. [Nicolaou, K. C.; Heretsch, P.; El Marrouni, A.; Hale, C. R. H.; Pulukuri, K. K.; Kudva, A. K.; Narayan, V.; Prabhu, K. S. Total Synthesis of $\Delta^{12}$-Prostaglandin J, a Highly Potent and Selective Antileukemic Agent. *Angew. Chem. Int. Ed.* 2014, 53, 10443-10447. Nicolaou, K. C.; Pulukuri, K. K.; Yu, R.; Rigol, S.; Heretsch, P.; Grove, C. I.; Hale, C. R. H.; El Marrouni, A. Total Synthesis of $\Delta^{12}$ Prostaglandin J$_3$; Evolution of Synthetic Strategies to a Streamlined Process. *Chem.-Eur. J.* 2016, 22, 8559-8570. Petšs, A.; Gandhamsetty, N.; Smith, J. R.; Mailhol, D.; Silvi, M.; Watson, A. J. A.; Perez-Powell, I.; Prévost, S.; Schützenmeister, N.; Moore, P. R.; Aggarwal V. K. Reoptimization of the Organocatalyzed Double Aldol Domino Process to a Key Enal Intermediate and Its Application to the Total Synthesis of $\Delta^{12}$-Prostaglandin J$_3$ *Chem.-Eur. J.* 2018, 24, 9542-9545.]

A number of $\Delta^{12}$-PGJ$_3$ analogues were also accessible via a streamlined synthesis developed by Nicolaou and co-workers to enable a comprehensive structural-activity relationship (SAR) study of their anti-cancer activities. [Nicolaou, K. C.; Pulukuri, K. K.; Rigol, S.; Heretsch, P.; Yu, R.; Grove, C. I.; Hale, C. R. H.; ElMarrouni, A.; Fetz, V.; Bronstrup, M.; Aujay M.; Sandoval J.; Gavrilyuk J. Synthesis and Biological Investigation of $\Delta^{12}$-Prostaglandin J$_3$ ($\Delta^{12}$-PGJ$_3$) Analogues and Related Compounds. *J. Am. Chem. Soc.* 2016, 138, 6550-6560.]

DETAILED DESCRIPTION

Terminology and Definitions

Unless otherwise indicated, the invention is not limited to specific reactants, reaction conditions, or the like, as such may vary. It is also to be understood that the terminology used herein is for the purpose of describing particular embodiments and is not to be interpreted as being limiting.

As used in the specification and the appended claims, the singular forms "a," "an," and "the" include plural referents unless the context clearly dictates otherwise. Thus, for example, reference to "a substituent" encompasses a single substituent as well as two or more substituents, and the like.

As used in the specification and the appended claims, the terms "for example". "for instance", "such as" or "including" are meant to introduce examples that further clarify more general subject matter. Unless otherwise specified, these examples are provided only as an aid for understanding the invention and are not meant to be limiting in any fashion.

In this specification and in the claims that follow, reference will be made to a number of terms, which shall be defined to have the meanings as described herein.

The term "alkyl" as used herein, refers to a linear, branched, or cyclic saturated hydrocarbon group typically although not necessarily containing 1 to 24 carbon atoms, preferably 1 to 12 carbon atoms, such as methyl (Me), ethyl (Et), n-propyl (Pr or n-Pr), isopropyl (i-Pr), n-butyl (Bu or n-Bu), isobutyl (i-Bu), t-butyl (t-Bu), octyl (Oct), decyl, and the like, as well as cycloalkyl groups such as cyclopentyl (Cp), cyclohexyl (Cy) and the like. Generally, although again not necessarily, alkyl groups herein contain 1 to about 8 carbon atoms. The term "lower alkyl" refers to an alkyl group of 1 to 6 carbon atoms, and the specific term "cycloalkyl" refers to a cyclic alkyl group, typically having 3 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to 24 carbon atoms containing at least one double bond, such as ethenyl, n-propenyl, iso-propenyl, n-butenyl, iso-butenyl, octenyl, decenyl, tetradecenyl, hexadecenyl, and the like. Preferred alkenyl groups herein contain 2 to 12 carbon atoms. The term "lower alkenyl" refers to an alkenyl group of 2 to 6 carbon atoms, and the specific term "cycloalkenyl" refers to a cyclic alkenyl group, preferably having 3 to g carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to 24 carbon atoms containing at least one triple bond, such as ethynyl, n-propynyl, and the like. Preferred alkynyl groups herein contain 2 to 12 carbon atoms. The term "lower alkynyl" refers to an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkynylene" as used herein refers to a difunctional alkynyl group, where "alkynyl" is as defined above.

The term "alkoxy" as used herein refers to an alkyl group bound through a single, terminal ether linkage; that is, an "alkoxy" group may be represented as —O-alkyl where alkyl is as defined above. A "lower alkoxy" group refers to an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 6 to 10 carbon atoms. Exemplary aryl groups contain one aromatic ring or two fused or linked aromatic rings, e.g., phenyl (Ph), naphthyl, biphenyl, diphenylether, diphenylamine, benzophenone, phenanthryl and the like. "Substituted aryl" refers to an aryl moiety substituted with one or more substituent groups, and the terms "heteroatom containing aryl" and "heteroaryl" refer to aryl substituents in which at least one carbon atom is replaced with a heteroatom, as will be described in further detail herein.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 6 to 10 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, without limitation, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The term "acyl" refers to substituents having the formula —(CO)-alkyl, —(CO)-aryl, —(CO)-aralkyl, —(CO)-alkaryl, —(CO)-alkenyl, or —(CO)-alkynyl, and the term "acyloxy" refers to substituents having the formula —O(CO)-alkyl, —O(CO)-aryl, —O(CO)-aralkyl, —O(CO)-alkaryl, —O(CO)-alkenyl, or —(CO)-alkynyl wherein "alkyl," "aryl", "aralkyl", "alkaryl", "alkenyl", and "alkynyl" are as defined above. The acetoxy group (—O(CO)CH$_3$, often abbreviated as —OAc) is a common example of an acyloxy group.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The term "polycyclic ring" refers to alicyclic or aromatic groups that may or may not be substituted and/or heteroatom containing, and that have at least two closed rings tethered, fused, linked via a single bond or bridged. Polycyclic rings include without limitation naphthyl, biphenyl, phenanthryl and the like.

The term "spiro compound" refers to a chemical compound, that presents a twisted structure of two or more rings (a ring system), in which 2 or 3 rings are linked together by one common atom, The terms "halo" and "halogen" and "halide" are used in the conventional sense to refer to a fluorine (F), chlorine (Cl), bromine (Br), or iodine (I) substituent.

The terms "cis"/"Z" and "trans"/"E" as used herein, are used interchangeably and refer to the geometry of the double bonds.

"Hydrocarbyl" refers to univalent hydrocarbyl radicals containing 1 to 24 carbon atoms, most preferably 1 to 12 carbon atoms, including linear, branched, cyclic, saturated and unsaturated species, such as alkyl groups, alkenyl groups, alkynyl groups, aryl groups, and the like. The term "lower hydrocarbyl" refers to a hydrocarbyl group of 1 to 6 carbon atoms, preferably 1 to 4 carbon atoms, and the term "hydrocarbylene" refers to a divalent hydrocarbyl moiety containing 1 to 24 carbon atoms, preferably 1 to 12 carbon atoms, including linear, branched, cyclic, saturated and unsaturated species. The term "lower hydrocarbylene" refers to a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and "heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect the term "aryl." Examples of heteroalkyl groups include without limitation alkoxyaryl, alkylsulfanyl-substituted alkyl, N-alkylated amino alkyl, and the like. Examples of heteroaryl substituents include without limitation pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups include without limitation pyrrolidino, morpholino, piperazino, piperidino, etc.

By "substituted" as in "substituted hydrocarbyl", "substituted alkyl", "substituted aryl", and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation groups such as halo, hydroxyl, sulfhydryl, $C_1$-$C_{24}$ alkoxy, $C_2$-$C_{24}$ alkenyloxy. $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_5$-$C_{24}$ alkyl)$_2$), mono-($C_1$-$C_{24}$ haloalkyl)-substituted carbamoyl (—(CO)—NH($C_1$-$C_{24}$ haloalkyl)), di-($C_1$-$C_{24}$ haloalkyl)-substituted carbamoyl (—(CO)—N($C_1$-$C_{24}$ haloalkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl), N—($C_5$-$C_{24}$ aryl)-substituted carbamoyl (—(CO)—N($C_1$-$C_{24}$ alkyl) ($C_5$-$C_{24}$ aryl), thiocarbamoyl (—(CS)—$NH_2$), mono-($C_1$-$C_{24}$ alkyl)-substituted thiocarbamoyl (—(CS)—NH($C_1$-$C_{24}$ alkyl)), di-($C_1$-$C_{24}$ alkyl)-substituted thiocarbamoyl (—(CS)—N($C_1$-$C_{24}$ alkyl)$_2$), mono-($C_5$-$C_{24}$ aryl)-substituted thiocarbamoyl (—(CS)—NH-aryl), di-($C_5$-$C_{24}$ aryl)-substituted thiocarbamoyl (—(CS)—N($C_5$-$C_{24}$ aryl)$_2$), di-N—($C_5$-$C_{24}$ alkyl), N—($C_5$-$C_{24}$ aryl)-substituted thiocarbamoyl (—(CS)—N($C_1$-$C_{24}$ alkyl)($C_5$-$C_{24}$ aryl), carbamido (—NH—(CO)—$NH_2$), cyano(—C≡N), cyanato (—O—C≡N), thiocyanato (—S—C≡N), isocyanate (—NCO), thioisocyanate (—NCS), formyl (—(CO)—H), thioformyl (—(CS)—H), amino (—$NH_2$), mono-($C_1$-$C_{24}$ alkyl)-substituted amino (—NH($C_1$-$C_{24}$ alkyl), di-($C_1$-$C_{24}$ alkyl)-substituted amino ((—N($C_1$-$C_4$ alkyl)$_2$), mono-($C_5$-$C_{24}$ aryl)-substituted amino (—NH($C_5$-$C_{24}$ aryl), di-($C_5$-$C_{24}$ aryl)-substituted amino (—N($C_5$-$C_{24}$ aryl)$_2$), $C_2$-$C_{24}$ alkylamido (—NH—(CO)-alkyl), $C_6$-$C_{24}$ arylamido (—NH—(CO)-aryl), imino (—CRNH where, R includes without limitation H, $C_1$-$C_2$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CRN(alky), where R includes without limitation H, $C_1$-$C_{24}$ alkyl, $C_5$-$C_{24}$ aryl, $C_6$-$C_{24}$ alkaryl, $C_6$-$C_{24}$ aralkyl, etc.), arylimino (—CRN(aryl), where R includes without limitation H, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_1$-$C_{24}$ monoalkylaminosulfonyl (—$SO_2$—N(H) alkyl), $C_1$-$C_{24}$ dialkylaminosulfonyl (—$SO_2$—N(alkyl)$_2$), $C_5$-$C_{24}$ arylsulfonyl (—$SO_2$-aryl), boryl (—$BH_2$), borono (—B(OH)$_2$), boronato (—B(OR)$_2$ where R includes without limitation alkyl or other hydrocarbyl), phosphono (—P(O)(OH)$_2$), phospho (—$PO_2$), phosphino (—$PH_2$), silyl (—$SiR_3$ wherein R is H or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl). $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

By "functionalized" as in "functionalized hydrocarbyl", "functionalized alkyl", "functionalized olefin", "functionalized cyclic olefin", and the like, is meant that in the hydrocarbyl, alkyl, olefin, cyclic olefin, or other moiety, at least one H atom bound to a carbon (or other) atom is replaced with one or more functional groups such as those described hereinabove. The term "functional group" is meant to include any functional species that is suitable for the uses described herein. In particular, as used herein, a functional group would necessarily possess the ability to react with or bond to corresponding functional groups on a substrate surface.

In addition, the aforementioned functional groups may, if a particular group permits, be further substituted with one or more additional functional groups or with one or more hydrocarbyl moieties such as those specifically enumerated above. Analogously, the above mentioned hydrocarbyl moieties may be further substituted with one or more functional groups or additional hydrocarbyl moieties such as those specifically mentioned above. Analogously, the above-mentioned hydrocarbyl moieties may be further substituted with one or more functional groups or additional hydrocarbyl moieties as noted above.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "terminal olefin" as used herein means an olefin wherein one of the olefinic carbons (i.e., the carbons of the carbon-carbon double bond) is substituted by at least one non-hydrogen substituent and the other olefinic carbon is unsubstituted.

The term "nil", as used herein, means absent or nonexistent.

The term "sulfhydryl" as used herein, represents a group of formula "—SH".

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)$R^x$, wherein $R^x$ can be alkyl, aryl, cycloalkyl, cycloalkenyl, heterocycle as defined above.

The term "ester" as used herein, represents an organic compound having a carbonyl group linked to a carbon atom such as —C(O)O$R^x$ wherein $R^x$ can be alkyl, aryl, cycloalkyl, cycloalkenyl, heterocycle as defined above.

The term "amine" as used herein, represents a group of formula "—N$R^x R^y$", wherein $R^x$ and R can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—$NO_2$".

The term "cyano" as used herein, represents a group of formula "—CN".

The term "amide" as used herein, represents a group of formula "C(O)N$R^x R^y$", wherein $R^x$ and $R^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Functional groups may be protected in cases where the functional group interferes with the metathesis catalyst, and any of the protecting groups commonly used in the art may be employed. Acceptable protecting groups may be found, for example, in Greene et al., Protective Groups in Organic Synthesis, 5th Ed. (New York: Wiley, 2014). Examples of protecting groups include acetals, cyclic acetals, boronate esters (boronates), cyclic boronate esters (cyclic boronates), carbonates, or the like. Examples of protecting groups include cyclic acetals or cyclic boronate esters.

SUMMARY

Olefin cross-metathesis is a convergent method for building C—C double bonds in natural product syntheses. [Cheng-Sánchez, I.; Sarabia, F. Recent Advances in Total Synthesis via Metathesis Reactions. *Synthesis* 2018, 50, 3749-3786. Fürstner, A. Metathesis in Total Synthesis. *Chem. Commun.* 2011, 47, 6505. Nicolaou, K. C.; Bulger, P. G.; Sarlah, D. Metathesis Reactions in Total Synthesis. *Angew. Chrem. Int. Ed.* 2005, 44, 4490-4527.] However, it has seldom been applied in the previous syntheses of Δ$^{12}$-PGJ family. Most importantly, conventional metathesis catalysts typically gave imperfect control of alkene geometry.

Previous syntheses relied on the semi-hydrogenation of alkynes or Wittig reactions, requiring multi-step functional group manipulation with concomitant waste generation. From a strategic perspective, chemoselectivity among multiple alkenes has also been another concern, especially in the later stages. Stereoselective and alkene-chemoselective metathesis catalysts are in demand to realize a convergent synthesis from simple alkene building blocks.

A series of cyclometallated ruthenium-based catalysts (e.g. Ru-1, Ru-2) as shown in FIG. 2, were recently developed by Grubbs and co-workers.

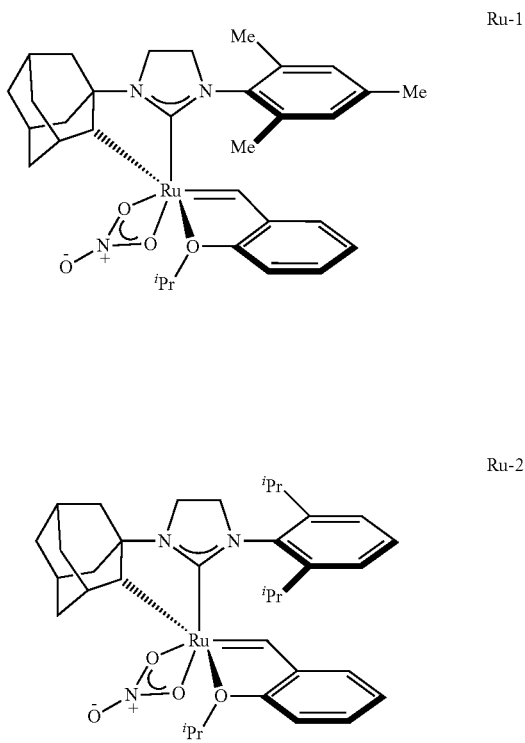

Figure 2. Z-selective metathesis catalysts

The ruthenium catalysts of FIG. 2 enabled Z-selective metathesis through a favored syn-metallocyclobutane intermediate (Scheme 1, Path A).

Scheme 1

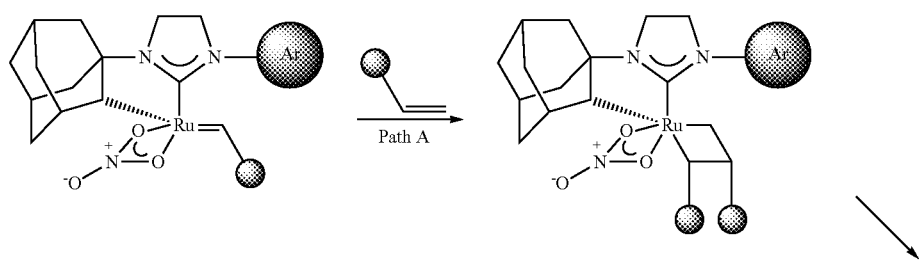

Model of Z-selectivity:

Model of Stereoretention:

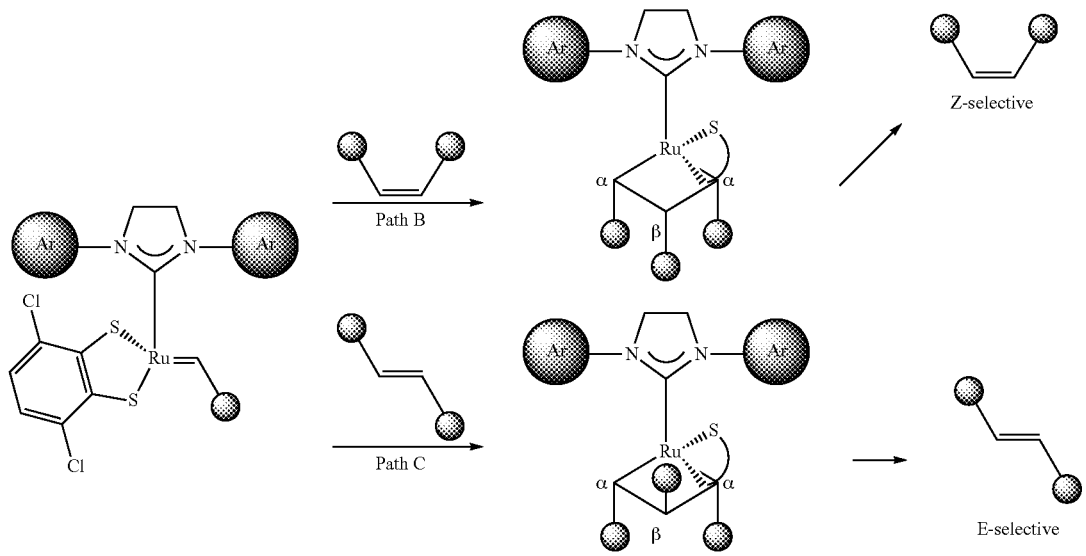

[Endo, K.; Grubbs, R. H. Chelated Ruthenium Catalysts for Z-Selective Olefin Metathesis. *J. Am. Chem. Soc.* 2011, 133, 8525-8527. Keitz, B. K.; Endo, K.; Patel, P. R.; Herbert, M. B.; Grubbs, R. H. Improved Ruthenium Catalysts for Z-Selective Olefin Metathesis. *J. Am. Chem. Soc.* 2012, 134, 693-699.]

More recently, catechodithiolate-based catalyst Ru-3 and its dithiolate variants were developed by Hoveyda group and showed high Z-selectivity in ring opening metathesis polymerizations, ring-opening cross-metathesis, and cross-metathesis with Z-olefins.

Figure 3. Stereoretentive metathesis catalysts

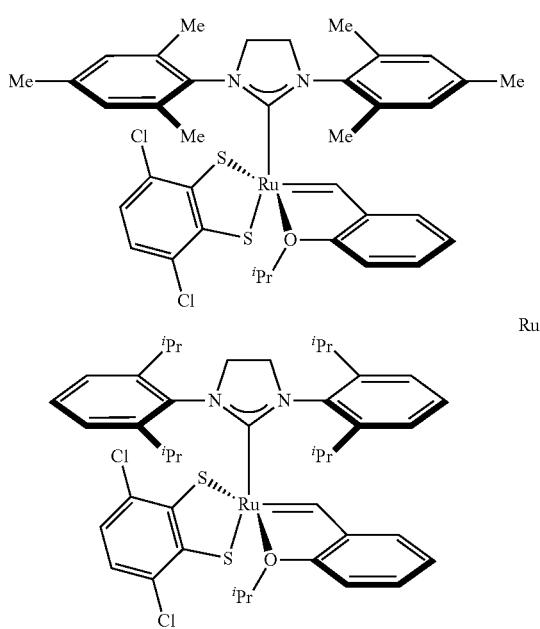

In fact, high kinetic E-selectivity in cross-metathesis with E-starting materials was also observed with Ru-3, the s-lPr analogue Ru-4, and other less bulky fast-initiating analogues developed by Materia Inc. and the Grubbs group, that defined these catalysts as stereoretentive. [Johns, A. M.; Ahmed, T. S.; Jackson, B. W.; Grubbs, R. H.; Pederson, R. L. High Trans Kinetic Selectivity in Ruthenium-Based Olefin Cross-Metathesis through Stereoretention. *Org. Lett.* 2016, 18, 772-775. Ahmed, T. S.; Grubbs, R. H. Fast-Initiating, Ruthenium-Based Catalysts for Improved Activity in Highly E-Selective Cross Metathesis. *J. Am. Chem. Soc.* 2017, 139, 1532-1537. Khan, R. K. M.; Torker, S.; Hoveyda, A. H. Readily Accessible and Easily Modifiable Ru-Based Catalysts for Efficient and Z-Selective Ring-Opening Metathesis Polymerization and Ring-Opening/Cross-Metathesis. *J. Am. Chem. Soc.* 2013, 135, 10258-10261. Hoveyda, A. H. Evolution of Catalytic Stereoselective Olefin Metathesis: From Ancillary Transformation to Purveyor of Stereochemical Identity. *J. Org. Chem.* 2014, 79, 4763-4792. Koh, M. J.; Khan, R. K. M.; Torker, S.; Hoveyda, A. H. Broadly Applicable Z- and Diastemoselective Ring-Opening/Cross-Metathesis Catalyzed by a Dithiolate Ru Complex. *Angew. Chem. Int. Ed.* 2014, 53, 1968-1972.]

The origin of the stereoretention was attributed to the formation of a side-bound metallacyclobutane intermediate, of which the α-substituents are forced down to minimize steric interactions with the bulky N-aryl groups of the NHC. As a result, when starting with Z-alkenes, the β-substituent points down to generate Z-alkene products (Scheme 1, Path B). When starting with E-alkenes, however, the β-substituent has to point up into the open space between two N-aryl groups, leading to the generation of E-alkene products, albeit with slower rates (Scheme 1, Path C).

Cross-metathesis between two terminal alkenes is not possible with stereoretentive metathesis catalysts however, because the intermediate methylidene species are unstable and lead to catalyst decomposition. [Koh, M. J.; Khan, R. K. M.; Torker, S.; Yu. M.; Mikus, M. S.; Hoveyda, A. H. High-Value Alcohols and Higher-Oxidation-State Compounds by Catalytic Z-Selective Cross-Metathesis. *Nature* 2015, 517, 181-186.]

A methylene capping strategy was recently reported as a remedy to this problem, enabling the cross-metathesis of two terminal alkenes. [Xu, C.; Shen, X.; Hoveyda, A. H. In Situ Methylene Capping: A General Strategy for Efficient Stereoretentive Catalytic Olefin Metathesis. The Concept, Methodological Implications, and Applications to Synthesis of Biologically Active Compounds. *J. Am. Chem. Soc.* 2017, 139, 10919-10928.] Despite the unique properties of these stereoretentive catalysts, to date, limited synthetic evaluation of these catalysts has been conducted. [Stereoretentive metathesis using Ru: Montgomery, T. P.; Ahmed, T. S.; Grubbs. R. H. Stereoretentive Olefin Metathesis: An Avenue to Kinetic Selectivity. *Angew. Chem. Int. Ed* 2017, 56, 11024-11036. Ahmed, T. S.; Grubbs, R. H. A Highly Efficient Synthesis of Z-Macrocycles P.; Grubbs. R. H. Using Macrocyclic Ring-Closing Metathesis. *Nature* 2017, 541, 380-385. Koh. M. J.; Nguyen, T. T.; Lam, J. K.; Torker, S.; Hyvl, J.; Schrock, R. R.; Hoveyda, A. H. Molybdenum Chloride Catalysts for Z-Selective Olefin Metathesis Reactions. *Nature* 2017, 542, 80-85.]

Herein, we present a total synthesis of the olefin-enriched $\Delta^{12}$-prostaglandin J natural products (1)-(4) of FIG. 1, by implementing a concise stereoretentive metathesis approach. This also sets a perfect test ground to evaluate the reactivity, chemoselectivity, and functional group compatibility of these newly developed metathesis catalysts.

Retrosynthetically, $\Delta^{12}$-PGJ$_3$ (3) for example, can be simplified into a truncated prostaglandin structure 22 by use of stereoretentive metathesis (Scheme 2).

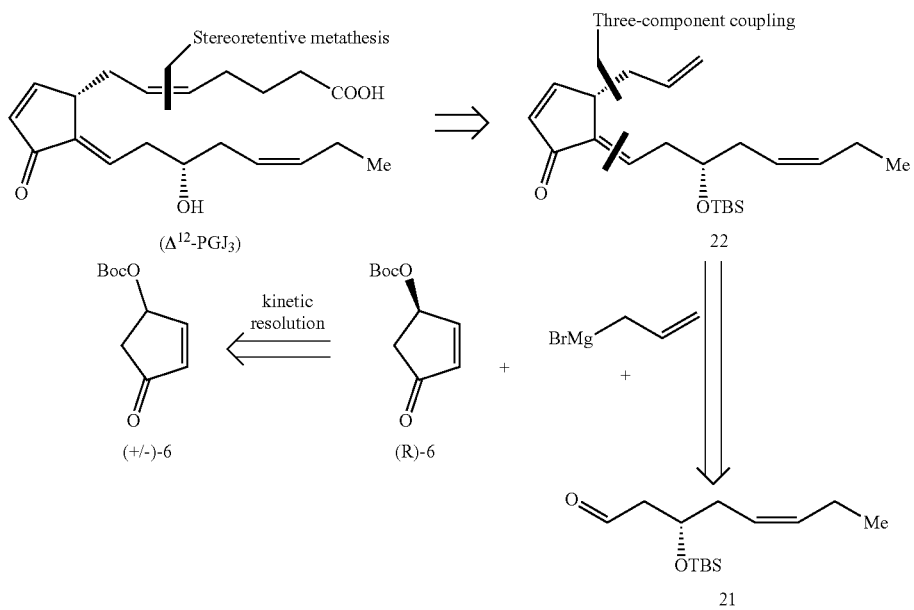

Scheme 2. Retrosynthetic Analysis of $\Delta^{12}$-PGJ$_3$ (3)

Stereoretention for the Synthesis of E-Macrocycles with Ruthenium-Based Olefin Metathesis Catalysts. *Chem. Sci.* 2018, 9, 3580-3583. Jung, K.; Kim, K.; Sung, J.-C.; Ahmed, T. S.; Hong, S. H.; Grubbs, R. H.; Choi, T.-L. Toward Perfect Regiocontrol for β-Selective Cyclopolymerization Using a Ru-Based Olefin Metathesis Catalyst. *Macromolecules* 2018, 51, 4564-4571. Stereoretentive metathesis using Mo, W: Couturier, J.-L.; Paillet, C.; Leconte, M.; Basset, J.-M.; Weiss, K. A Cyclometalated Aryloxy(Chloro) Neopentylidene-tungsten Complex: A Highly Active and Stereoselective Catalyst for the Metathesis of Cis- and Trans-2-Pentene. Norbornene, 1-Methyl-Norbornene, and Ethyl Oleate. *Angew. Chem. Int. Ed* 1992, 31, 628-631. Lam, J. K.; Zhu, C.; Bukhryakov, V.; Müller, P.; Hoveyda, A.; Schrock, R. R. Synthesis and Evaluation of Molybdenum and Tungsten Monoaryloxide Halide Alkylidene Complexes for Z-Selective Cross-Metathesis of Cyclooctene and Z-1,2-Dichloroethylene. *J. Am. Chem. Soc.* 2016, 138, 15774-15783. Nguyen, T. T.; Koh, M. J.; Shen, X.; Romiti, F.; Schrock, R. R.; Hoveyda, A. H. Kinetically Controlled E-Selective Catalytic Olefin Metathesis. *Science* 2016, 352, 569-575. Shen, X.; Nguyen. T. T.; Koh, M. J.; Xu, D.; Speed, A. W. H.; Schrock. R. R.; Hoveyda, A. H. Kinetically E-Selective A three-component coupling strategy can be applied toward the synthesis of 22, using a relatively simple and commercially available allyl Grignard reagent, w-chain aldehyde 21, and a chiral cyclopentenone (R)-6. The O-Boc group of (R)-6 can be used as a traceless stereoinductive group to set the C8 stereocenter. [Noyori, R.; Suzuki, M. Prostaglandin Syntheses by Three-Component Coupling. *Angew. Chem. Int. Ed.* 1984, 23, 847-876. Arisetti, N.; Reiser, O. Traceless Stereoinduction for the Enantiopure Synthesis of Substituted-2-Cyclopentenones. *Org. Lett.* 2015, 17, 94-97.]

Following the retrosynthetic analysis of $\Delta^{12}$-PGJ$_3$ (3) we aimed to synthesize $\Delta^{12}$-PGJ$_2$ (1). Therefore, chiral cyclopentenone (R)-6 was prepared from furfuryl alcohol in a three-step process including a kinetic resolution method developed by Reiser and coworkers (Scheme 3). [Ulbrich, K.; Kreitmeier, P.; Vilaivan, T.; Reiser, O. Enantioselective Synthesis of 4-Heterosubstituted Cyclopentenones. *J. Org. Chem.* 2013, 78, 4202-4206.]

Scheme 3. Preparation of Chiral Cyclopentenone (R)-6

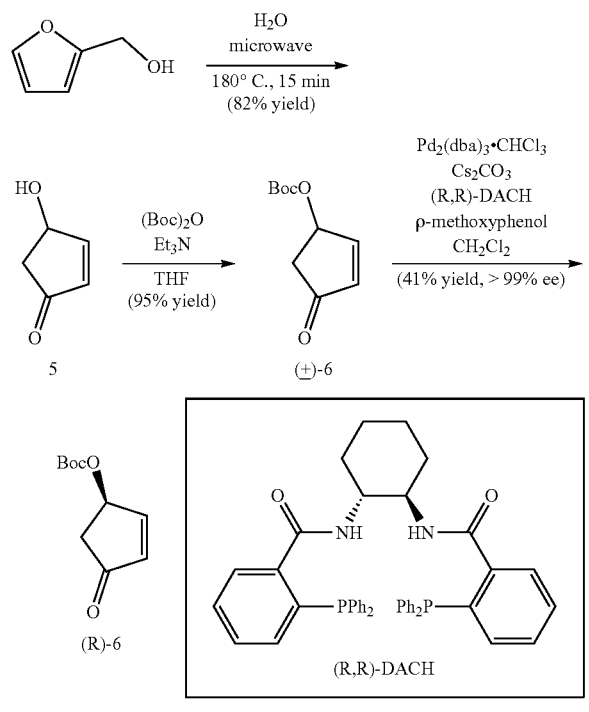

The ω-chain aldehyde 10 was prepared from hexanal 7 through asymmetric Keck allylation, [Yadav, J. S.; Suresh, B.; Srihari, P. Stereoselective Total Synthesis of the Marine Macrolide Sanctolide A: Total Synthesis of the Marine Macrolide Sanctolide A. *Eur. J. Org Chem.* 2015, 201, 5856-5863.] The TBS protection, and ozonolysis are also shown in (Scheme 4).

Scheme 4. Preparation of ω-Chain Aldehyde Chain

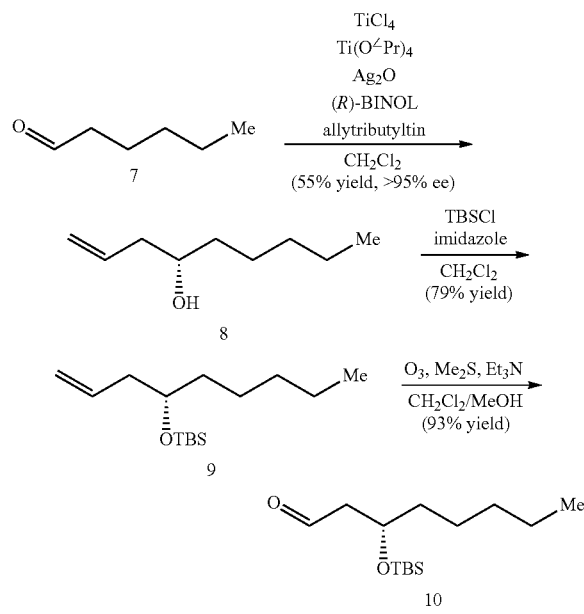

With all the starting materials for the three-component coupling in hand, CuBr·Me$_2$S and LiCl facilitated the diastereoselective conjugate addition of the allyl magnesium bromide. The enolate formed was trapped by the subsequently added m-chain aldehyde electrophile, and the O-Boc group was eliminated in the course of the aldol reaction to form the desired cyclopentenone.

Elimination with MsCl and DMAP favored E-product 11 as the major product in reasonable yield (45% over 2 steps, Scheme 5).

Scheme 5. Preparation of Product 11

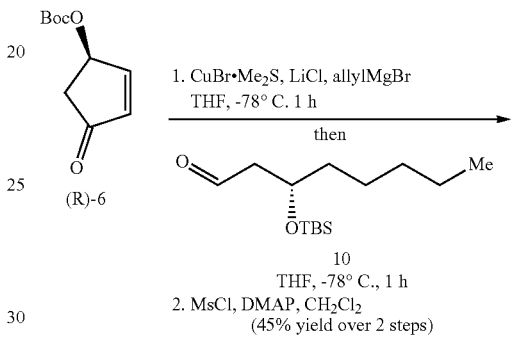

Stereoretentive metathesis was then evaluated on 11. Since 11 cannot react with another terminal alkene using stereoretentive metathesis catalysts, we considered a symmetric Z-alkene 13 as the coupling partner, which could also be made by homodimerization of readily available 12 through stereoretentive metathesis. With 1 mol % loading of Ru-4 as the catalyst, 98% conversion could be achieved by applying dynamic vacuum to remove the by-product, cis-3-hexene (bp 66-68° C.) from the reaction mixture. Next, 11 with an additional S mol % catalyst Ru-4 were added into the reaction mixture, and the alcohol product 14 could be isolated in 95% yield in high Z-selectivity (>99% Z). This result established the efficacy of an efficient one-pot, stereoretentive homodimerization/cross-metathesis strategy to build the CS Z-alkene.

Scheme 6. Preparation of Alcohol 14

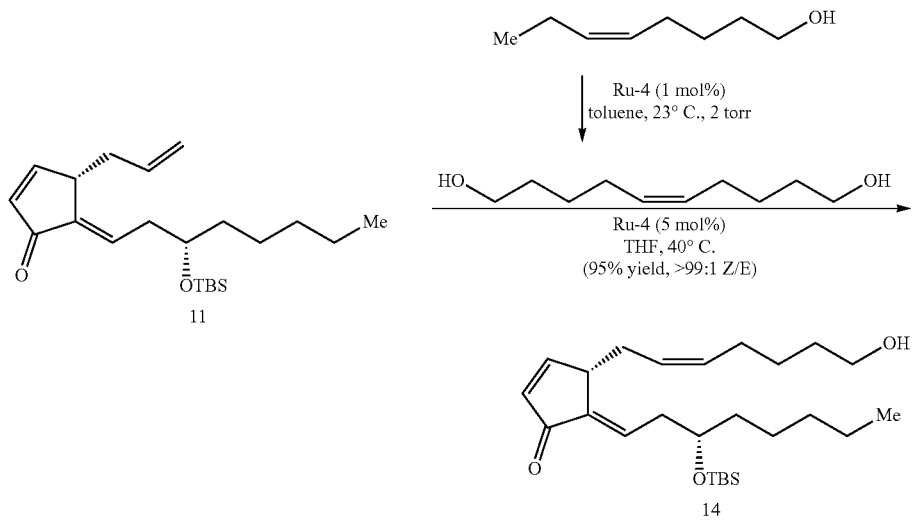

In contrast, synthesis of PGE2 and PGF2a required a large excess of gaseous butene and more complicated operations in the previously reported methylene capping strategy. [Xu, C.; Shen, X.; Hoveyda, A. H. In Situ Methylene Capping: A General Strategy for Efficient Stereoretentive Catalytic Olefin Metathesis. The Concept, Methodological Implications, and Applications to Synthesis of Biologically Active Compounds. *J. Am. Chem. Soc.* 2017, 139, 10919-10928.] Ley oxidation and deprotection of the TBS group of 14 in aqueous HF furnished the natural product $\Delta^{12}$-prostaglandin J$_2$ (1) in 89% yield over the last two steps.

Scheme 5. Preparation of Product 16

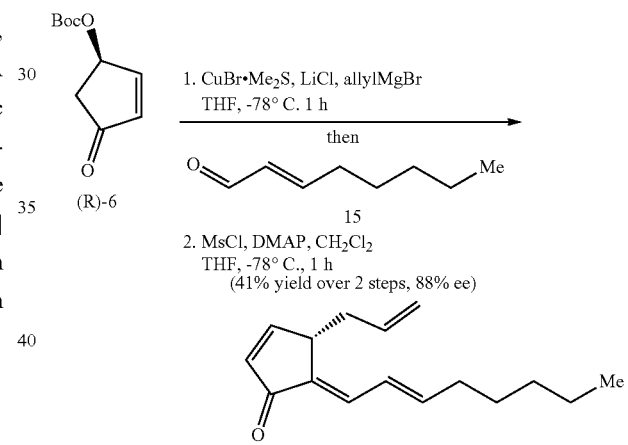

16 was then subjected to the standard one-pot stereoretentive homodimerization/cross-metathesis conditions, and alcohol 17 was obtained in excellent yield (93% yield, Scheme 9) with high 2-selectivity (>99% Z). The C14 E-alkene tolerated the reaction, consistent with the much slower reaction of E-alkenes with Ru-4 as seen previously. [Johns, A. M.; Ahmed, T. S.; Jackson, B. W.; Grubbs, R. H.; Pederson, R. L. High Trans Kinetic Selectivity in Ruthenium-Based Olefin Cross-Metathesis through Stereoretention. *Org. Lett.* 2016, 18, 772-775. Ahmed, T. S.; Grubbs, R. H. Fast-Initiating. Ruthenium-Based Catalysts for Improved Activity in Highly E-Selective Cross Metathesis. *J. Am. Chem. Soc.* 2017, 139, 1532-1537.] We also assessed the enantiopurity of intermediates 16 and 17. Three-component coupling product 16 proceeded with a small loss in enantiopurity (88% cc) from (R)-6 (>99% ee); but the metathesis product 17 was obtained without significant erosion of enantiopurity (87% ee).

Scheme 7. Synthesis of $\Delta^{12}$-Prostaglandin J$_2$ (1)

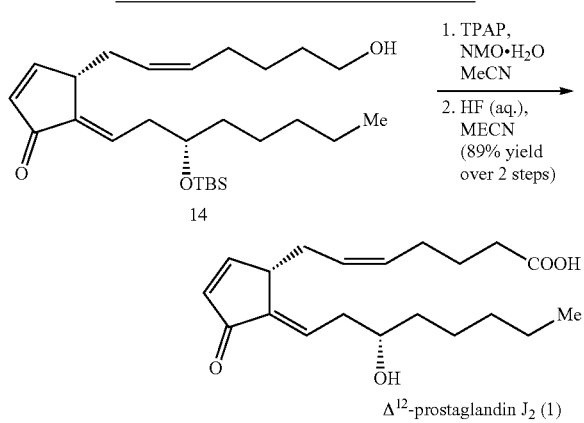

The same three-component coupling sequence was performed to obtain 16, and the enal functionality of aldehyde 15 was well tolerated in the aldol step, as shown in Scheme 8.

Scheme 9. Preparation of Alcohol 17

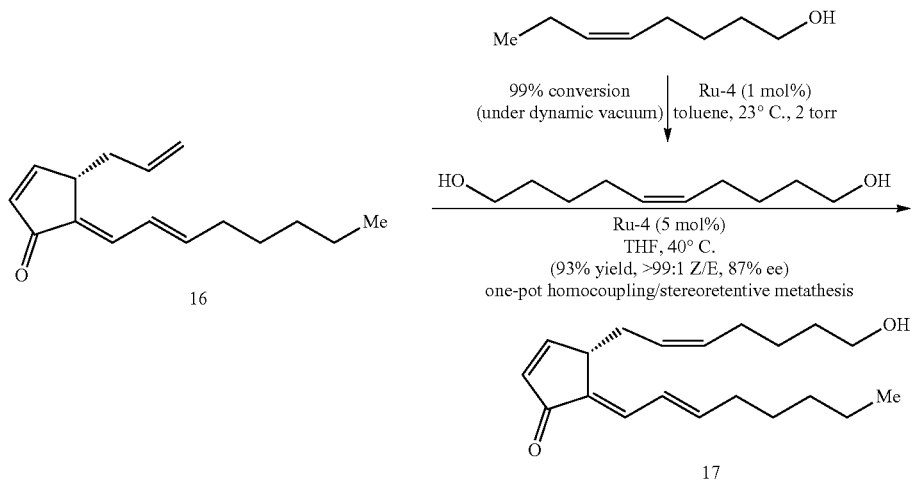

This result demonstrates that stereoretentive metathesis with catalyst Ru-4 also retained the stereochemistry of the C8 stereocenter. Ley oxidation of 17 again gave 15-deoxy-$\Delta^{12,14}$-prostaglandin $J_2$ (2) in 68% yield.

Scheme 10. Synthesis of $\Delta^{12,14}$-Prostaglandin $J_2$ (2)

Synthesis of $\Delta^{12}$-prostaglandin $J_3$ (3) began with the preparation of the ω-chain aldehyde 21. We envisioned the Z-alkene in 21 could also be generated from stereoretentive metathesis. First, we obtained chiral alcohol 18 through a reported chiral pool strategy with (R)-epichlorohydrin as the starting material (Scheme 11). [Bai, Y.; Shen, X.; Li, Y.; Dai, M. Total Synthesis of (−)-Spinosyn A via Carbonylative Macrolactonization. *J. Am. Chem. Soc.* 2016, 138, 10838-1084.]

Scheme 11. Preparation of ω-Chain Aldeheyde

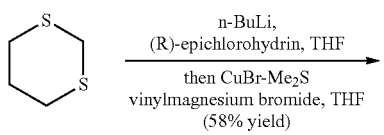

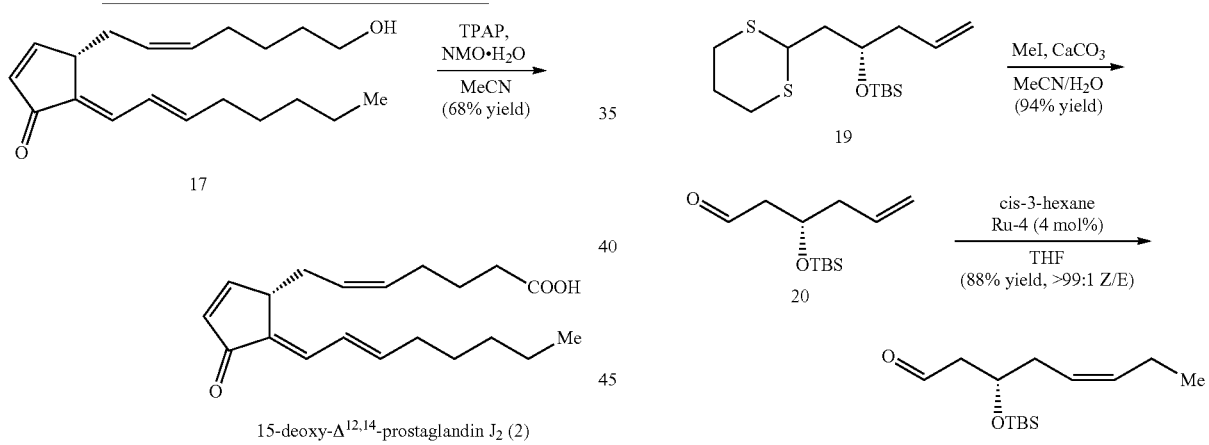

TBS protection of the alcohol 18 and subsequent removal of the 1,3-dithiol gave aldehyde 20. Stereoretentive metathesis of 20 with an excess amount of cis-3-hexene using catalyst Ru-4 (4 mol %) afforded ω-chain aldehyde 21 in good yield (88%) with high Z-selectivity (>99% Z). The short synthesis of aldehyde 21 proved that a broad range of functional groups, including aldehydes, can be tolerated without protecting group manipulations using stereoretentive catalysts. Then, product 22 was synthesized through the standard three-component coupling sequence from (R)-6 (Scheme 12).

Scheme 12. Preparation of Product 22

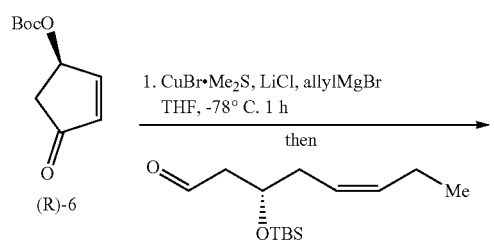

1. CuBr·Me₂S, LiCl, allylMgBr
   THF, -78° C. 1 h
   then

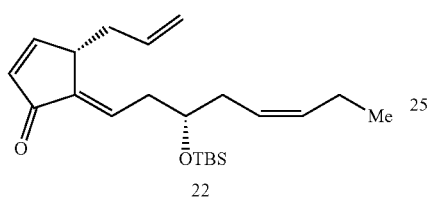

2. MsCl, DMAP, CH₂Cl₂
   THF, -78° C., 1 h
   (40% yield over 2 steps)

Alternatively, we chose to use cyclometallated catalyst Ru-2 to circumvent the crossover of alkene reactivity. Because tri-substituted metallacyclobutane intermediates are highly unfavorable with this cyclometallated catalyst, this pathway can be easily avoided FIG. 4.

FIG 4: Trisubstituted Metallacyclobutane Intermediate with Ru-2

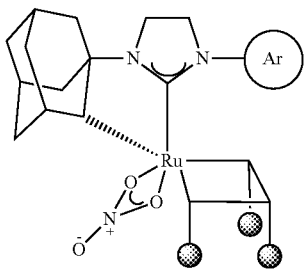

Scheme 14. Preparation of Alcohol 23 in the presence of Ru-2

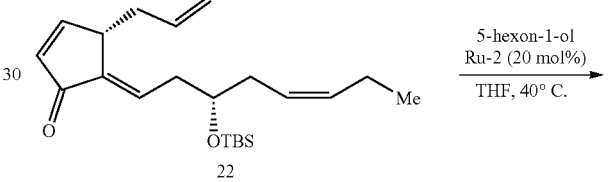

5-hexon-1-ol
Ru-2 (20 mol%)
THF, 40° C.

Surprisingly, fast ring closing metathesis (RCM) with Ru-4 yielded 24 as a byproduct (31% yield) bearing an unusual 9-membered ring and the desired alcohol product 23 was obtained in only 44% yield.

Scheme 13. Preparation of Alcohol 23 in the presence of Ru-4

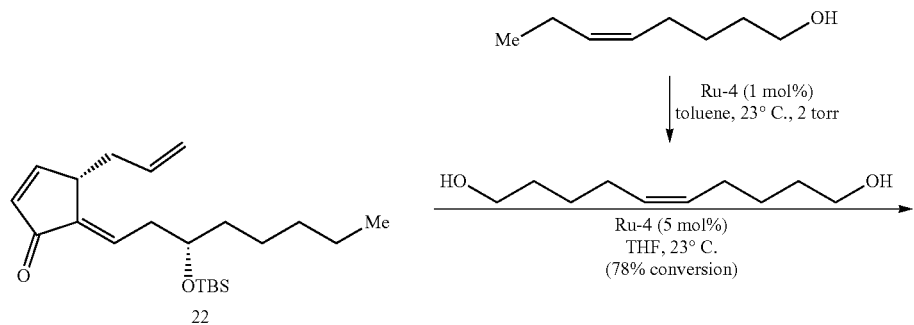

Ru-4 (1 mol%)
toluene, 23° C., 2 torr

Ru-4 (5 mol%)
THF, 23° C.
(78% conversion)

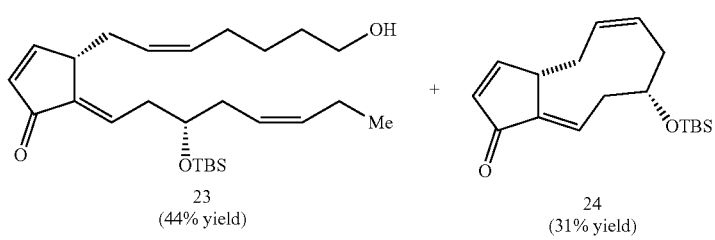

23
(44% yield)

24
(31% yield)

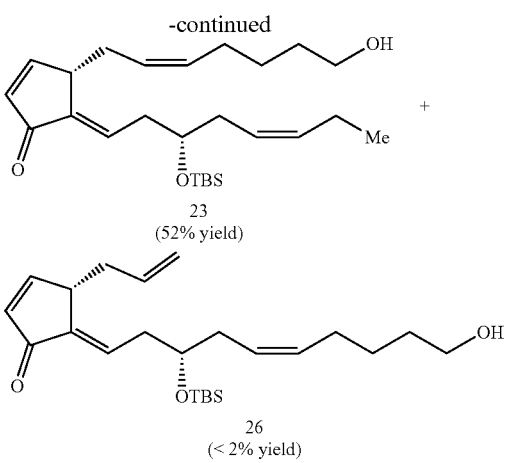

23 (52% yield)

26 (< 2% yield)

[Herbert, M. B.; Grubbs, R. H. Z-Selective Cross Metathesis with Ruthenium Catalysts: Synthetic Applications and Mechanistic Implications. *Angew. Chem. Int. Ed* 2015, 54, 5018-5024.] Chemoselective cross-metathesis of 5-hexen-1-ol (25) with the allyl group of 22 furnished the desired product 23 in good yield (52%) with a trace amount of by-product 26 (less than 2%, Scheme 14). The RCM product 24 was not observed under these conditions.

The side-reaction of $C_{17}$ internal Z-alkene could be attributed to ethylene produced or the residual ruthenium methylidene species in the solution. Then, Ley oxidation of 23 and deprotection of the TBS group with aqueous HF provided $\Delta^{12}$-prostaglandin $J_3$ (3) in 8 linear steps.

Scheme 15. Synthesis of $\Delta^{12}$-Prostaglandin $J_3$ (3)

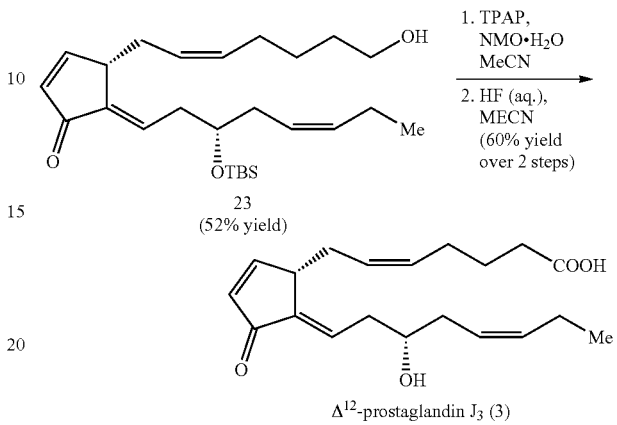

Finally, in the synthesis of 15d-PGJ$_3$ (4)(Scheme 16), crossover of metathesis reactivity between the allyl group and the C17 Z-alkene of 28 could also be expected. Standard stereoretentive metathesis conditions with Ru-4 provided desired product 29 in 36% yield and by-products 30 and 31.

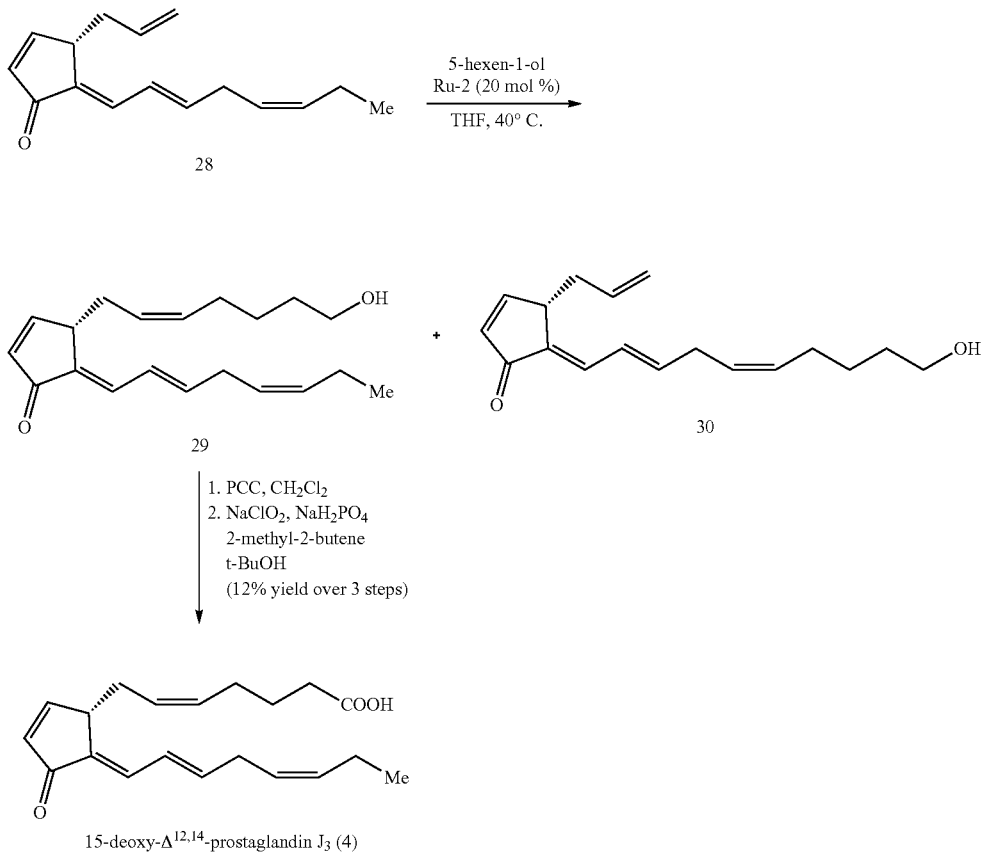

28 as well as by-products 29 and 30 were obtained using Ru-2 and no improvement of chemoselectivity was observed. Compared to $\Delta^{12}$-PGJ$_3$ (3) synthesis, where the steric bulk of the OTBS group may be beneficial to achieving good chemoselectivity, 28 has no such steric hindrance. However, no RCM of 28 was observed, possibly due to the ring strain of the RCM product. Though 30 could not be separated from 29, the mixture was subjected to pyridinium chlorochromate (PCC) oxidation and Pinnick oxidation conditions allowing us to isolate 15-deoxy-$\Delta^{12,14}$-prostaglandin J$_3$ (4) (12% yield from 28). Ley oxidation of a mixture of 29 and 30 was also performed but resulted in a significant amount of decomposition products.

In conclusion, we were able to achieve a concise and convergent synthesis of four $\Delta^{12}$-prostaglandin J natural products in shorter sequences (7-8 steps in the longest linear sequences) empowered by stereoretentive and stereoselective metathesis. Furthermore, the reactivity, chemoselectivity, and functional group compatibility of stereoretentive metathesis was evaluated. This study should inspire further practical applications of stereoselective metathesis, such as a facile one-pot stereoretentive homodimerization/cross-metathesis strategy to introduce Z-alkenes with excellent geometric control. The modularity and expediency of this chemistry opens the synthesis of other prostaglandins and analogues to enable SAR studies in cancer treatment. With the well-defined kinetically Z/E-selective catalysts that have been developed to overcome the inherent thermodynamic preference of alkene product geometry, olefin metathesis can play a pivotal role in the synthesis design.

Olefin Metathesis Catalysts

In one embodiment, the invention provides a stereoretentive ruthenium olefin metathesis catalyst represented by the structure of Formula (I),

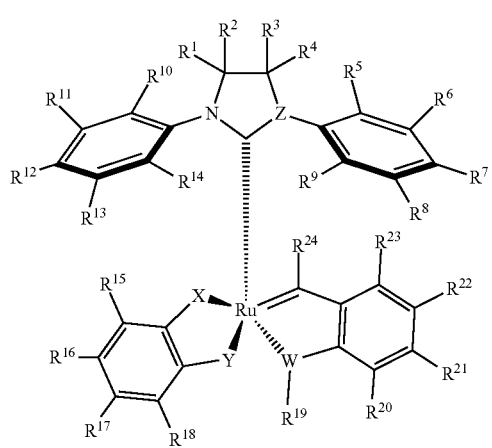

Formula (I)

wherein:
X is O or S;
Y is O or S;
Z is N or CR$^{32}$;
W is O, halogen, NR$^{33}$ or S;
R$^1$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^2$ can form a spiro compound or together with R$^3$ or together with R$^4$ can form a polycyclic ring;
R$^2$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^1$ can form a spire compound or together with R$^3$ or together with R$^4$ can form a polycyclic ring;
R$^3$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —R(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl or together with R$^2$ or together with R$^1$ can form a polycyclic ring or together with R$^4$ can form a spiro compound;
R$^4$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^3$ can form a spiro compound or together with R$^2$ or together with R$^1$ can form a polycyclic ring;
R$^5$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^6$ can form an optionally substituted polycyclic ring;
R$^6$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)R$^2$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^5$ or together with R$^7$ can form an optionally substituted polycyclic ring;
R$^7$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl optionally substituted C$_{3-8}$ cycloalkenyl, or together with R$^6$ or together with R$^8$ can form an optionally substituted polycyclic ring;
R$^8$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^7$ or together with R$^9$ can form an optionally substituted polycyclic ring;
R$^9$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^8$ can form an optionally substituted polycyclic ring;
R$^{10}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen. —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring;

$R^{17}$ is H, optionally substituted $C_{1-24}$ alkyl, halogen, —C(O)$R^{25}$, —OR$^{26}$, CN, —NR$^{27}$R$^{28}$, NO$_2$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{18}$ or together with $R^{16}$ can form an optionally substituted polycyclic ring;

$R^{18}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ can form an optionally substituted polycyclic ring;

$R^{19}$ is H, optionally substituted $C_{1-24}$ alkyl, —C(R$^{34}$)(R$^{35}$)COOR$^{36}$, —C(R$^{34}$)(R$^{35}$)C(O)H, —C(R$^{34}$)(R$^{35}$)C(O)R$^{37}$, —C(R$^{34}$)(R$^{35}$)CR$^{38}$(OR$^{39}$)(OR$^{40}$), —C(R$^{34}$)(R$^{35}$)C(O)NR$^{41}$R$^{42}$, —C(R$^{34}$)(R$^{35}$)C(O)NR$^{41}$OR$^{40}$, —C(O)R$^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{20}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$ optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring;

$R^{21}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$. —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{21}$ can form a polycyclic ring;

$R^{22}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring:

$R^{22}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$, aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{75}$ is OH, OR$^{30}$, NR$^{27}$R$^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, OR$^{26}$, —NR$^{27}$R$^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted. $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally, heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted C alkyl, optionally substituted $C_{3-8}$ cycloalkyl, optionally, heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally, heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

When certain groups, such as: $C_{1-24}$ alkyl, $C_{3-8}$ cycloalkyl, heterocycle, $C_{5-24}$ aryl, $C_{3-8}$ cycloalkenyl groups or the polycyclic rings, are optionally substituted, the substituents are selected from: halogen. —OH, —SH, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, —CO—($C_1$-$C_{24}$ alkyl), —CO— ($C_6$-$C_{24}$ aryl), —O—CO—($C_1$-$C_{24}$ alkyl), —O—CO—($C_6$-$C_{24}$ aryl), —(CO)—O—($C_1$-$C_{24}$ alkyl), —(CO)—O—($C_6$-$C_{24}$ aryl), (—O—(CO)—O—($C_1$-$C_{24}$ alkyl), —O—(CO)—O—($C_6$-$C_{24}$ aryl), (—COOH), (—(CO)—NH$_2$), (—(CO)—NH($C_1$-$C_{24}$ alkyl)), (CO)—N ($C_1$-$C_{24}$ alkyl)$_2$), —(CO)—NH—($C_6$-$C_{24}$ aryl), —(CO)—N($C_5$-$C_{24}$ aryl)$_2$), —(CO)—N($C_1$-$C_{24}$ alkyl)($C_5$-$C_{24}$ aryl), (—(CS)—NH$_2$), (—(CS)—NH($C_1$-$C_{24}$ alkyl)), (—(CS)—N ($C_1$-$C_{24}$ alkyl)$_2$), —(CS)—NH—($C_5$-$C_{24}$ aryl), (—(CS)—N ($C_5$-$C_{24}$ aryl)$_2$), di-N—($C_1$-$C_{24}$ (—(CS)—N($C_1$-$C_{24}$ alkyl) ($C_5$-$C_{24}$ aryl), (—NH—(CO)—NH$_2$), (—C≡N), (—O—C≡N), (—S—C≡N), (—NCO), (—NCS), (—(CO)—H), (—(CS)—H), (—NH$_2$), (—NH($C_1$-$C_{24}$ ((—N($C_1$-$C_{24}$ alkyl)$_2$), (—NH($C_5$-$C_{24}$ aryl), (—N($C_5$-$C_{24}$ aryl)$_2$), —NH—(CO)—($C_1$-$C_6$ alkyl), —NH—(CO)—($C_6$-$C_{24}$ aryl), —C($C_1$-$C_{24}$ alkyl)(NH), (—CHN($C_4$-$C_{24}$ alkyl), (—CHN ($C_6$-$C_{24}$ aryl), (—NO$_2$), (—NO), (—SO$_2$—OH), —S—($C_1$-$C_{24}$ alkyl), (—S—($C_5$-$C_{24}$ aryl), (—(SO)—($C_1$-$C_{24}$ alkyl), (—(SO)—($C_5$-$C_{24}$ aryl), SO$_2$—($C_1$-$C_{24}$ alkyl), (—SO$_2$—N (H)($C_1$-$C_{24}$ alkyl), (—SO$_2$—N($C_1$-$C_{24}$ alkyl)$_2$), (—SO$_2$—($C_5$-$C_{24}$ aryl), (—BH$_2$), B(OH)$_2$), (—B(O)($C_1$-$C_{24}$ alkyl)$_2$, (—P(O)(OH)$_2$), (PO$_2$), (—PH$_2$), —SiH$_3$, (—O-silyl), $C_1$-$C_{24}$ alkyl, $C_1$-$C_{12}$ alkyl, $C_1$-$C_6$ alkyl, $C_2$-$C_{24}$ alkenyl, $C_2$-$C_{12}$ alkenyl, $C_2$-$C_6$ alkenyl, $C_2$-$C_{24}$ alkynyl, $C_2$-$C_{12}$ alkynyl, $C_2$-$C_6$ alkynyl, $C_5$-$C_{24}$ aryl, $C_5$-$C_{14}$ aryl, $C_6$-$C_{24}$ alkaryl, $C_6$-$C_{16}$ alkaryl, $C_5$-$C_{24}$ aralkyl, and $C_5$-$C_{16}$ aralkyl, which are as defined herein.

In another embodiment, the invention provides a catalyst represented by Formula (I) wherein: X is S; Y is S; Z is N or $CR^{32}$; W is O, $NR^{33}$ or S; $R^1$ is H, optionally substituted $C_{1-12}$ alkyl, halogen; $R^2$ is H, optionally substituted $C_{1-12}$ alkyl, halogen; $R^3$ is H, optionally substituted $C_{1-12}$ alkyl, halogen; is H, optionally substituted $C_{1-12}$ alkyl, halogen; $R^5$ is H, optionally substituted $C_{1-12}$ alkyl, halogen; $R^6$ is H, optionally substituted $C_{1-12}$ alkyl, halogen; is H, optionally substituted $C_{1-12}$ alkyl, halogen; $R^8$ is H, optionally substituted $C_{1-12}$ alkyl, halogen; $R^9$ is H, optionally substituted $C_{1-12}$ alkyl, halogen; $R^{10}$ is H, optionally substituted $C_{1-12}$ alkyl, halogen; is H, optionally substituted $C_{1-12}$ alkyl, halogen; $R^{12}$ is H, optionally substituted $C_{1-12}$ alkyl, halogen; Ria is H, optionally substituted $C_{1-12}$ alkyl, halogen; $R^{14}$ is H, optionally substituted $C_{1-12}$ alkyl, halogen; $R^{15}$ is H, optionally substituted $C_{1-12}$ alkyl, halogen, optionally substituted heterocycle, optionally substituted $C_{3-8}$ cycloalkyl, optionally substituted $C_6$-10 aryl or optionally substituted $C_{3-8}$ cycloalkenyl; $R^{16}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl; $R^{17}$ is H, optionally substituted $C_{1-12}$ alkyl, halogen,—optionally substituted heterocycle, optionally substituted $C_{3-8}$ cycloalkyl, optionally substituted $C_{6-10}$ aryl or optionally substituted $C_{3-8}$ cycloalkenyl, or together with $R^{18}$ can form a polycyclic ring; $R^{18}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl, or together with $R^{17}$ can form a polycyclic ring; $R^{19}$ is H, optionally substituted $C_{1-12}$ alkyl, —C($R^{34}$)($R^{35}$)—COOR$^{36}$, —C($R^{34}$)($R^{35}$)—C(O)H, —C($R^{34}$)($R^{35}$)—C(O)R$^{37}$, —C($R^{34}$)($R^{35}$)—CR$^{38}$(OR$^{39}$)(OR$^{40}$), —C($R^{34}$)($R^{35}$)—C(O)—NR$^{41}$R$^{42}$, —C($R^{34}$)($R^{35}$)—C(O)—NR$^{41}$OR$^{40}$, —C(O)R$^{25}$, optionally substituted heterocycle, optionally substituted $C_{3-8}$ cycloalkyl, optionally substituted $C_{6-10}$ aryl, optionally substituted $C_{3-8}$ cycloalkenyl, or together with $R^{33}$ can form an optionally substituted heterocyclic ring; $R^{20}$ is H, optionally substituted $C_{1-12}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ can form a polycyclic ring; $R^{21}$ is H, optionally substituted $C_{1-12}$ alkyl, halogen, —NR$^{27}$R$^{28}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{20}$ or together with $R^{22}$ can form a polycyclic ring; $R^{22}$ is H, optionally substituted $C_{1-12}$ alkyl, halogen, —C(O)R$^{21}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ or together with $R^{23}$ can form a polycyclic ring; $R^2$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl or together with $R^2$ can form a polycyclic ring; $R^{24}$ is H; $R^{25}$ is OH, OR$^{30}$, NR$^{27}$R$^{28}$, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{26}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{27}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{28}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{29}$ is H, optionally substituted $C_{1-12}$ alkyl, OR$^{26}$, —NR$^{27}$R$^{28}$, optionally substituted heterocycle, optionally substituted $C_{3-8}$ cycloalkyl, optionally substituted $C_{6-10}$ aryl or optionally substituted $C_{3-8}$ cycloalkenyl; $R^{30}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{31}$ is H, optionally substituted $C_{1-12}$ alkyl, optionally substituted $C_{3-8}$ cycloakyl, optionally substituted heterocycle, optionally substituted $C_{6-10}$ aryl or optionally substituted $C_{3-8}$ cycloalkenyl; $R^{32}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{33}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl, or together with R can form an optionally substituted heterocyclic ring; $R^{34}$ is H, optionally substituted $C_{6-10}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{35}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{36}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{37}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{38}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{39}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{40}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{41}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{42}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; and x is 1 or 2.

In another embodiment, the invention provides a catalyst represented by Formula (I) wherein: X is S; Y is S; Z is N or CR$^{32}$; W is O or NR$^{32}$; $R^1$ is H, linear or branched $C_{1-6}$ alkyl, or halogen; $R^2$ is H linear or branched $C_{1-6}$ alkyl, or halogen; $R^3$ is H, linear or branched $C_{1-6}$ alkyl, or halogen; $R^4$ is H, linear or branched $C_{1-6}$ alkyl or halogen; $R^5$ is H, linear or branched $C_{1-6}$ alkyl; $R^6$ is H, linear or branched $C_{1-6}$ alkyl; $R^7$ is H, linear or branched $C_{1-6}$ alkyl; $R^8$ is H or $C_{1-6}$ alkyl; $R^9$ is H, linear or branched $C_{1-6}$ alkyl; $R^{10}$ is H, linear or branched $C_{1-6}$ alkyl; $R^{11}$ is H, linear or branched $C_{1-6}$ alkyl; $R^{12}$ is H, linear or branched $C_{1-6}$ alkyl; $R^{13}$ is H, linear or branched $C_{1-6}$ alkyl or together with $R^{14}$ forms a naphthyl ring; $R^{14}$ is H, linear or branched $C_{1-6}$ alkyl or together with $R^{13}$ forms a naphthyl ring; $R^{15}$ is H, phenyl, linear or branched $C_{1-6}$ alkyl, halogen or together with $R^{16}$ forms a naphthyl ring; $R^{16}$ is H, phenyl, linear or branched $C_{1-6}$ alkyl, halogen or together with $R^{15}$ or together with $R^{17}$ forms a naphthyl ring; $R^{17}$ is H, phenyl, linear or branched $C_{1-6}$ alkyl, halogen or together with $R^{16}$ or together with $R^{18}$ forms a naphthyl ring; $R^{18}$ is H, phenyl, linear or branched $C_{1-6}$ alkyl, halogen or together with $R^{16}$ or together with $R^{18}$ forms a naphthyl ring; $R^{19}$ is H, phenyl, $C_{1-6}$ alkyl, —C(R$^{34}$)(R$^{35}$) COOR$^{36}$, —C(R$^{34}$)(R$^{35}$) C(O)H, —C(R$^{34}$)(R$^{35}$) C(O)R$^{37}$, —C(R$^{34}$)(R$^{35}$)CR$^{38}$(OR$^{39}$)(OR$^{40}$), —C(R$^{34}$)(R$^{35}$) C(O) NR$^{41}$R$^{42}$, —C(R$^{34}$)(R$^{35}$) C(O) NR$^{41}$OR$^{40}$ or together with $R^{33}$ forms a five, six or seven membered heterocyclic ring; $R^{20}$ is H, linear or branched $C_{1-6}$ alkyl, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, cyclohexene or together with $R^{21}$ can form a polycycle; $R^{21}$ is H, phenyl, —NR$^{27}$R$^{28}$, linear or branched $C_{1-6}$ alkyl, halogen or together with $R^{20}$ or together with $R^{22}$ can form a polycycle; $R^{22}$ is H, linear or branched $C_{1-6}$ alkyl, halogen, —C(O)R$^{25}$, —OR$^{26}$, CN, —NR$^{28}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, cyclohexene or together with $R^{21}$ or together with $R^{23}$ can form a polycycle; $R^{23}$ is H, phenyl, linear or branched $C_{1-6}$ alkyl or together with $R^{22}$ can form a polycycle; $R^{24}$ is H, linear or branched $C_{1-6}$ alkyl; $R^{25}$ is OH, OR$^{30}$, NR$^{27}$R$^{28}$, linear or branched $C_{1-6}$ alkyl; $R^{26}$ is H, linear or branched $C_{1-6}$ alkyl; $R^{27}$ is H, linear or branched $C_{1-6}$ alkyl; $R^{28}$ is H, linear or branched $C_{1-6}$ alkyl; $R^{29}$ is H, linear or branched $C_{1-6}$ alkyl, —NR$^{27}$R$^{28}$; $R^{30}$ is optionally substituted $C_{1-6}$ alkyl, optionally substituted $C_{3-8}$ cycloalkyl, optionally substituted heterocycle, optionally substituted phenyl or optionally substituted $C_{3-8}$ cycloalkenyl; $R^{31}$ is H, linear or branched $C_{1-6}$ alkyl; $R^{32}$ is H, linear or branched $C_{1-6}$ alkyl; $R^{33}$ is H, linear or branched $C_{1-6}$ alkyl, or together with $R^{19}$ forms a five, six or seven membered heterocyclic ring; $R^{34}$ is H, or linear or branched $C_{1-6}$ alkyl; $R^{35}$ is H, or linear or branched $C_{1-6}$ alkyl; $R^{36}$ is H, linear or branched $C_{1-6}$ alkyl; $R^{37}$ is linear or branched $C_{1-6}$ alkyl; $R^{38}$ is H or linear or branched $C_{1-6}$ alkyl; $R^{39}$ is H, linear or branched $C_{1-6}$ alkyl; $R^{40}$ is H, linear or branched $C_{1-6}$ alkyl; $R^{41}$ is H, linear or branched $C_{1-6}$ alkyl; $R^{42}$ is H, linear or branched $C_{1-6}$ alkyl; and x is 1 or 2.

In one embodiment, the invention provides a catalyst represented by Formula (I) wherein: X is S; Y is S; Z is N or $CR^{32}$; W is O, $NR^{33}$ or S; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^5$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{10}$ is H, F, Cl, Br, I, Me, Et, i-Pr, n-Pr, n-Bu, t-Bu, or s-Bu; $R^{11}$ is H, Me, F, Cl, Br, I, Et, i-Pr, n-Pr, n-Bu, t-Bu, or s-Bu; $R^{12}$ is H, F, Cl, Br, I, Me, Et, i-Pr, n-Pr, n-Bu, t-Bu, or s-Bu; $R^{13}$ is H, Me, F, Cl, Br, I, Et, n-Pr, i-Pr, n-Bu, t-Bu or s-Bu; $R^{14}$ is F, Cl, Br, I, Me, lit, i-Pr, n-Pr, n-Bu, t-Bu, s-Bu or H; $R^{15}$ is H, Me, Et, i-Pr, n-Pr, n-Bu, t-Bu, s-Bu, F, Br, I, Cl, or together with $R^{16}$ forms a naphthyl or a phenanthryl ring; $R^{16}$ is H, F, Cl, Br, I, or together with $R^{15}$ forms a naphthyl or a phenanthryl ring; $R^{17}$ is H, F, Cl, Br, I, or together with $R^{18}$ forms a naphthyl, or a phenanthryl ring; $R^{18}$ is H, Cl, F, Br, I, 3,5-dichloro-phenyl, phenyl, Me, Et, i-Pr, n-Pr, n-Bu, t-Bu, s-Bu or together with $R^{17}$ forms a naphthyl, or a phenanthryl; R is H, phenyl, $C_{1-6}$ alkyl, $-C(R^{34})(R^{35}) COOR^{36}$, $-C(R^{34})(R^{35}) C(O)H$, $-C(R^{34})(R^{35}) C(O)R^{37}$, $-C(R^{34})(R^{35}) CR^{38}(OR^{39})(OR^{40})$, $C(R^{34})(R^{35})$, $-C(R^{34})(R^{35}) C(O) NR^{41}R^{42}$, $-C(R^{34})(R^{35}) C(O) NR^{41}OR^{40}$; $R^{20}$ is H, F, Cl, Br, I, Me, Et, i-Pr, n-Pr, n-Bu, t-Bu, s-Bu, $-C(O)R^{25}$, $-OR^{26}$, CN, $-NR^{27}R^{28}$, $NO_2$, $-CF_3$, $-S(O)_x R^{29}$, $-P(O)(OH)_2$, $-OP(O)(OH)$, $-SR^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, $-NR^{27}R^{28}$F, Cl, Br, or I; $R^{22}$ is H, Me, Et, i-Pr, halogen. $-C(O)R^{25}$, $-OR^{26}$, CN, $-NR^{27}R^{28}$, $NO_2$, $-CF_3$, $-S(O)R^{29}$, $-P(O)(OH)_2$, $-OP(O)(OH)_2$, $-SR^{31}$, pyridine, piperidine, imidazole, indolizine, indazole, cyclohexyl, phenyl, naphthalene, cyclohexene F, Cl, Br, or I; $R^{22}$ is H, $-C(O)R^{25}$, $-OR^{26}$, CN, $-NR^{27}R^{28}$, $NO_2$, $-CF_3$, $-S(O)_x R^{29}$, $-P(O)(OH)_2$, $-OP(O)(OH)_2$, or $-SR^{31}$; $R^{23}$ is H, F, Cl, Br, I, phenyl, Me, Et, i-Pr, n-Pr, n-Bu, t-Bu, or s-Bu; $R^{24}$ is H; $R^2$ is H, or Me; $R^{25}$ is OH, $OR^{30}$, $NR^{27}R^{28}$, Me, Et, or i-Pr; $R^{26}$ is H, Me, Et, i-Pr, n-Pr, n-Bu, or s-Bu; $R^{27}$ is H. Me, Et, or i-Pr; $R^{28}$ is H. Me, Et, i-Pr, n-Pr, n-Bu, t-Bu, or s-Bu; $R^{29}$ is H, Me, Et, i-Pr, n-Pr, n-Bu, t-Bu, s-Bu, or $-NR^{27}R^{28}$; $R^{30}$ is Me, Et, i-Pr, n-Pr, n-Bu, or s-Bu; $R^{31}$ is H, Me, Et, i-Pr, n-Pr, n-Bu, t-Bu, or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, E, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; and x is 1 or 2.

In one embodiment, the invention provides a catalyst represented by Formula (I) wherein: X is S; Y is S; Z is N; W is O; $R^1$ is Me or H; $R^2$ is Me or H; $R^3$ is H; $R^4$ is H; $R^5$ is H, F, Me, t-Bu or i-Pr; $R^6$ is H or t-Bu; $R^7$ is H, F or Me; $R^8$ is H, F or t-Bu; $R^9$ is H, F, Me, t-Bu or i-Pr; $R^{10}$ is H, F, Me, t-Bu or i-Pr; $R^{11}$ is H or t-Bu; $R^{12}$ is H, F or Me; $R^{13}$ is H, F or t-Bu; $R^{14}$ is F, Me, i-Pr, t-Bu or H; $R^{15}$ is H, Me, F. Br, I, Cl, or together with $R^{16}$ forms a naphthyl; $R^{16}$ is H, or together with $R^{15}$ forms a naphthyl; $R^{17}$ is H or together with $R^{18}$ forms a naphthyl, or a phenanthryl ring; $R^{18}$ is Cl, F, Br, I, 3,5-dichloro-phenyl, phenyl, t-Bu or together with $R^{17}$ forms a naphthyl, or a phenanthryl ring; $R^{19}$ is i-Pr; $R^{20}$ is H or phenyl; $R^{21}$ is H; $R^{22}$ is H, $-C(O)R^{25}$, $-OR^{26}$, CN, $-NR^{27}R^{28}$, $NO_2$, $-CF_3$, $-S(O)_x R^{29}$, $-P(O)(OH)_2$, $-OP(O)(OH)_2$, $-SR^{31}$; $R^{23}$ is H; $R^{24}$ is H; $R^{25}$ is OH, $OR^{30}$, $NR^{27}R^{28}$, Me, Pt, or i-Pr; $R^{26}$ is H, Me, Et, i-Pr, n-Pr, n-Bu, t-Bu, or s-Bu; $R^{27}$ is H, Me, Et, i-Pr, n-Pr, n-Bu, t-Bu, or s-Bu; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Ba, $-NR^{27}R^{28}$; $R^{30}$ is Me, Et, i-Pr, n-Pr, n-Bu, t-Bu, or s-Bu; and $R^{31}$ is H, Me, Et, i-Pr, n-Pr, n-Bu, t-Bu, or s-Bu.

In one embodiment, the invention provides a catalyst represented by Formula (I) wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; Ra is phenyl; $R^{20}$ is H; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is phenyl; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is Me; $R^2$ is Me; $R^3$ is H; $R^4$ is H; $R^5$ is F; $R^6$ is H; $R^7$ is H or F; $R^8$ is H; $R^9$ is F; $R^{10}$ is F; $R^{11}$ is H; $R^{12}$ is H; $R^{13}$ is H; $R^{14}$ is F; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a catalyst represented by Formula (I) wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment the invention provides a compound wherein the moiety
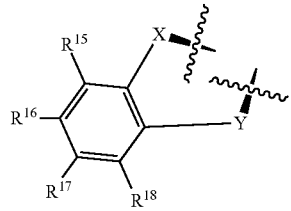
of Formula (I) is
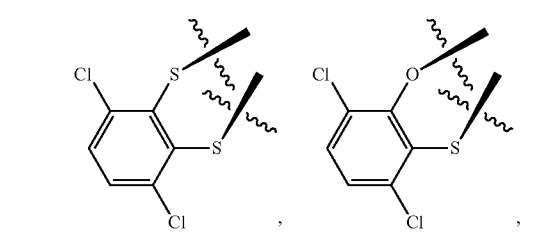
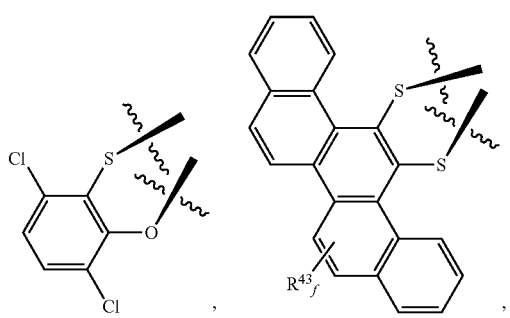
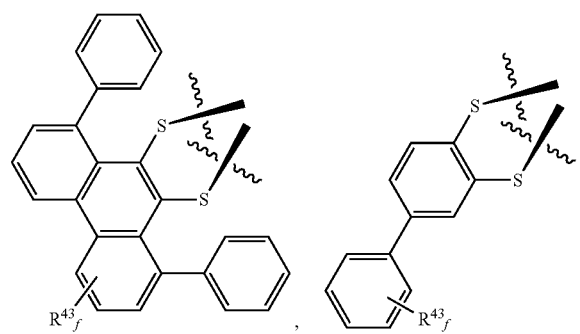
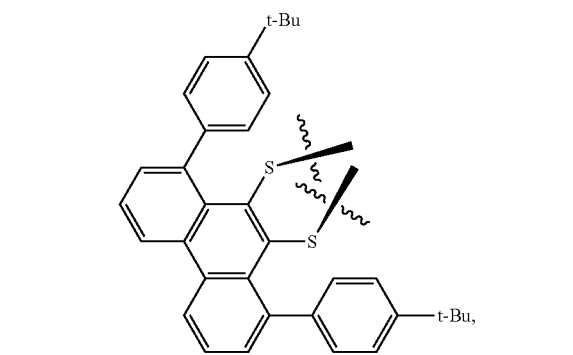
-continued
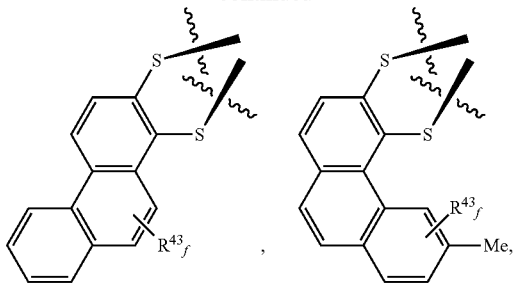
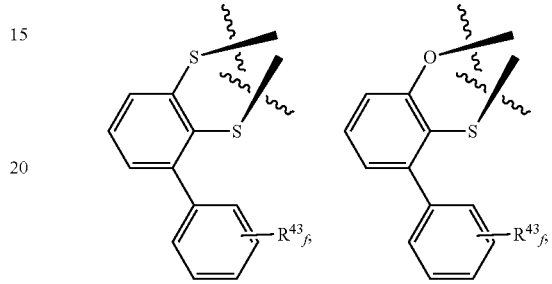
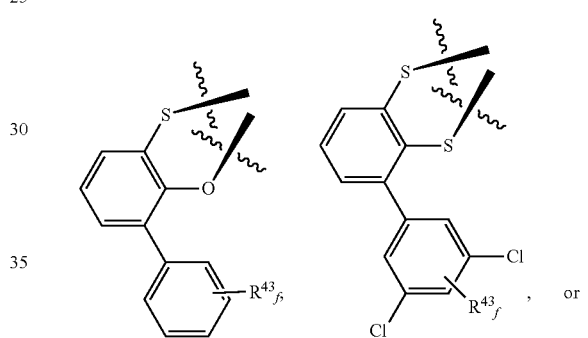
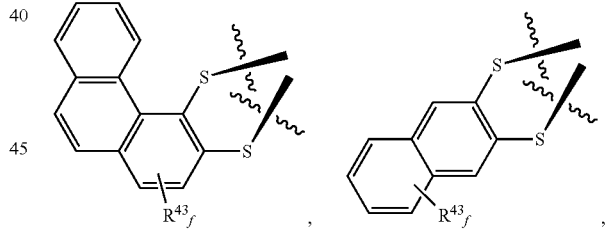
, or
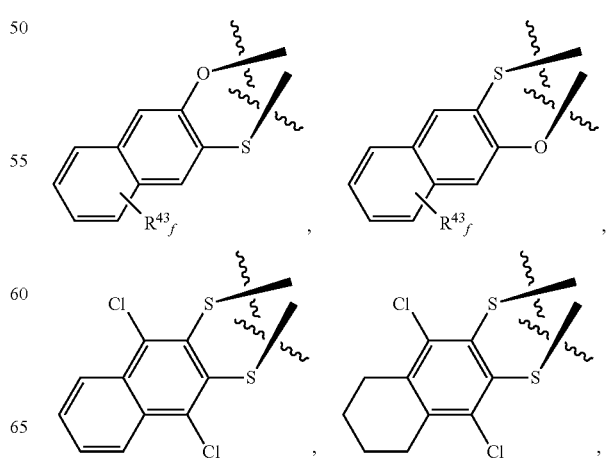
, -continued

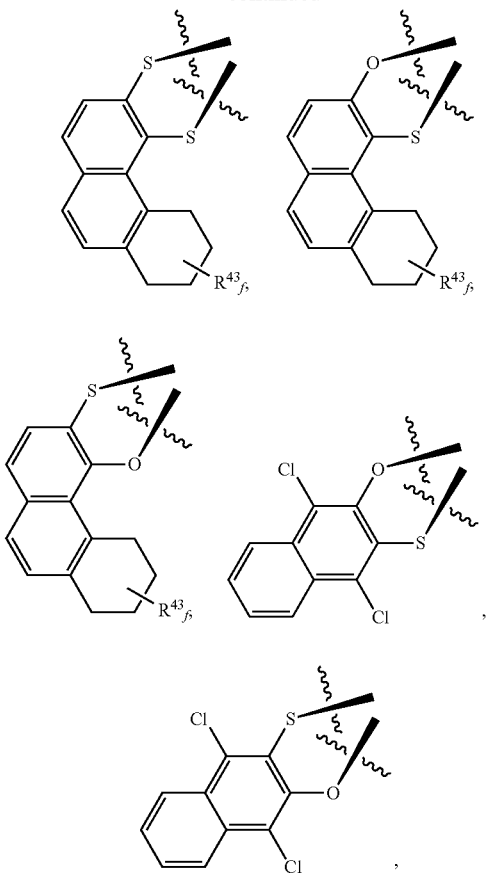

and wherein, $R^{43}$ is optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-4}$ cycloalkyl, optionally substituted $C_{5-24}$ aryl or optionally substituted $C_{3-8}$ cycloalkenyl, and "f" is 0, 1, 2, 3, or 4.

In one embodiment, the invention provides a compound wherein the moiety

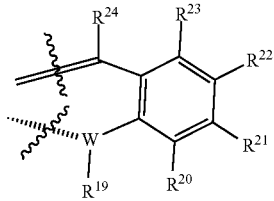

of Formula (I) is

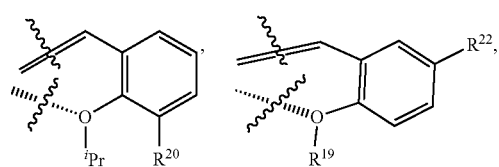

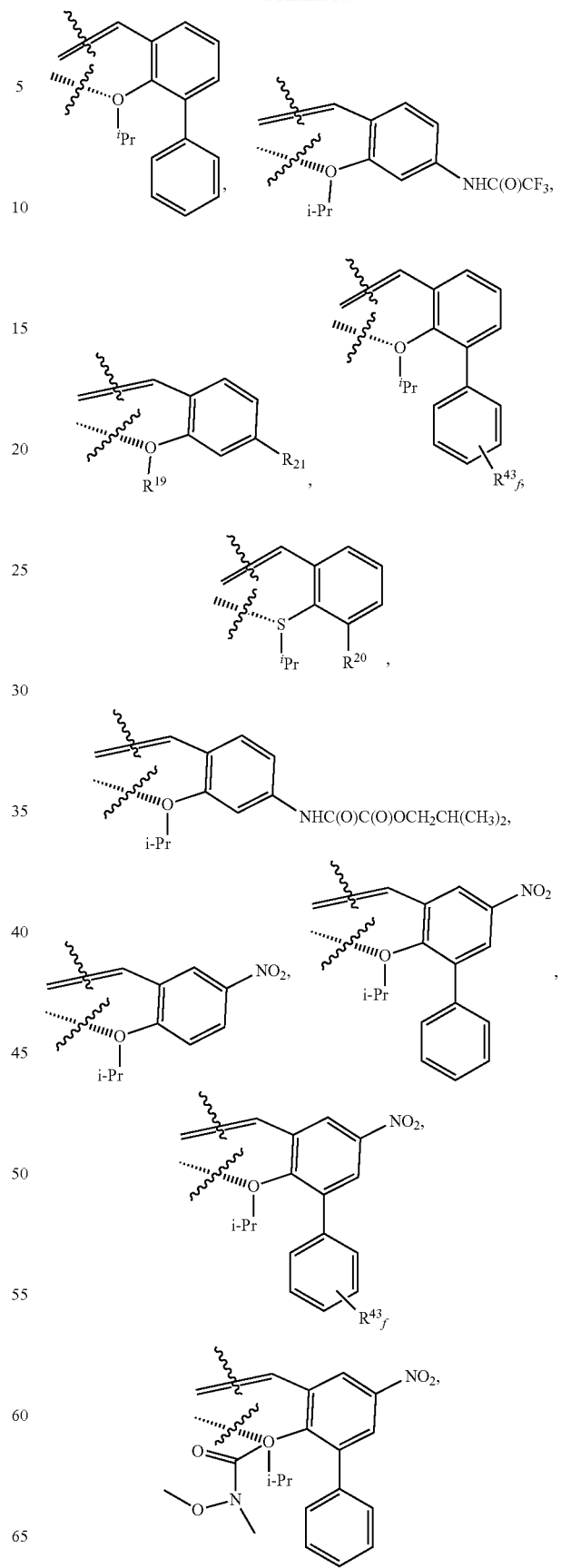

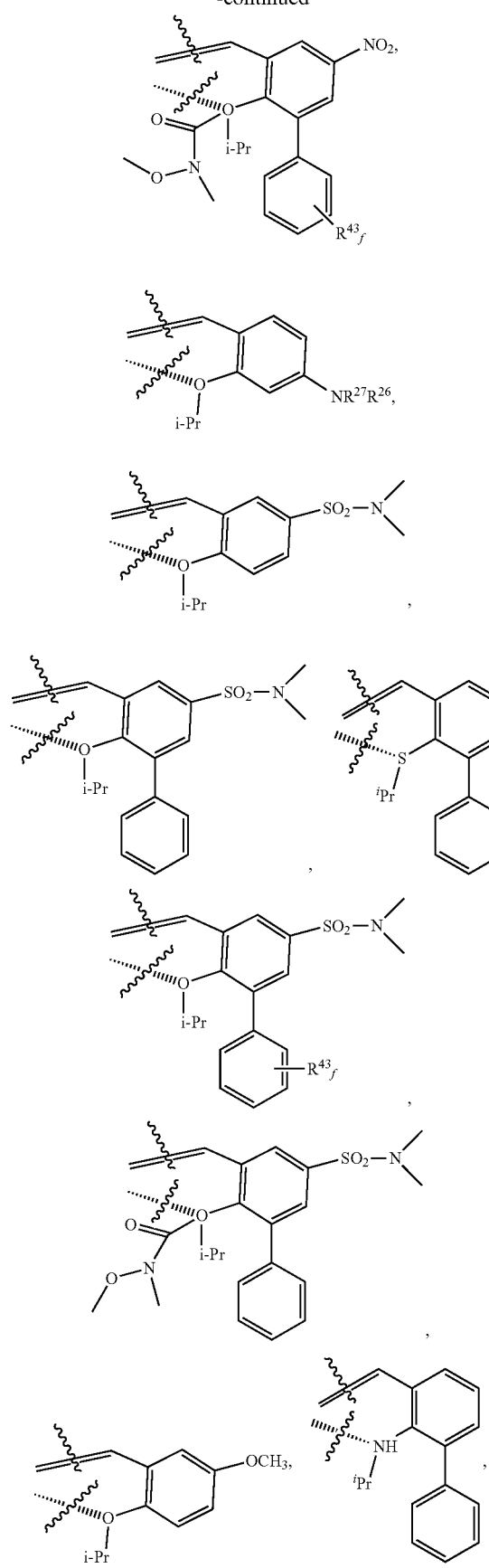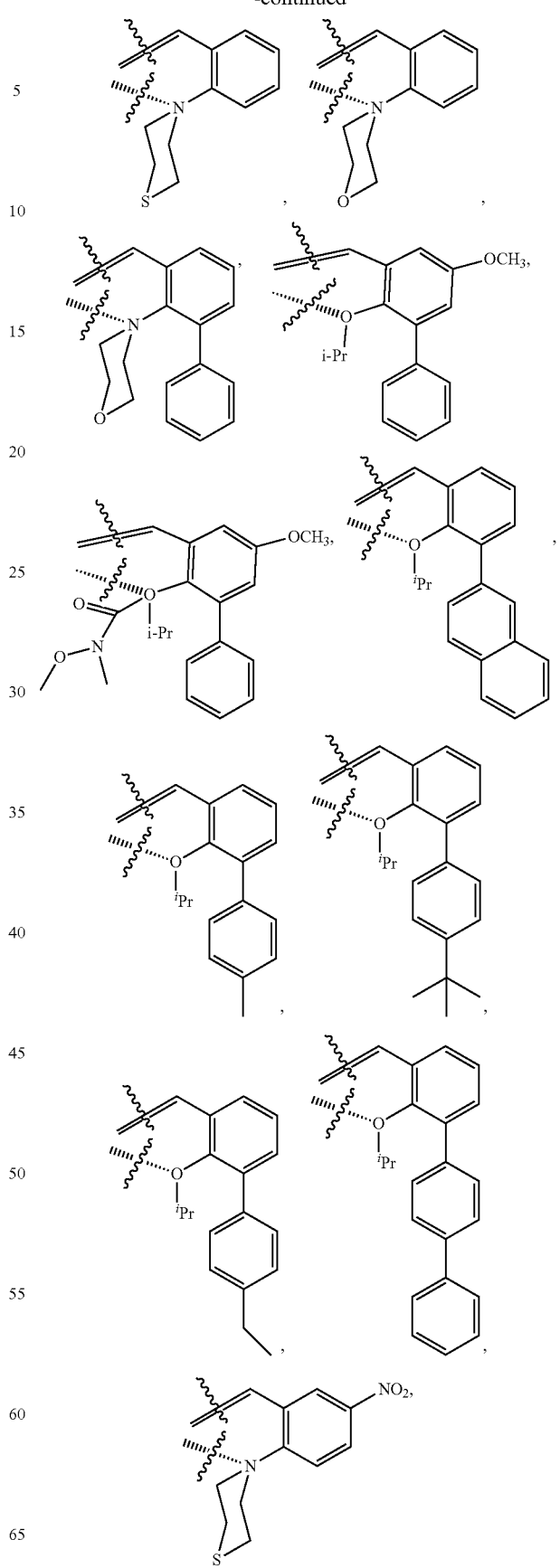

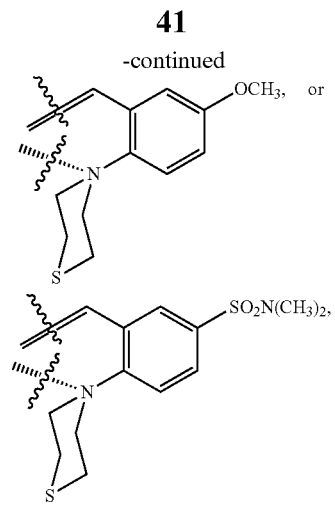
and wherein $R^{19}$, $R^{20}$, $R^{27}$, $R^{28}$, $R^{43}$ and "f" are as defined herein.
In one embodiment, the invention provides a compound wherein the moiety
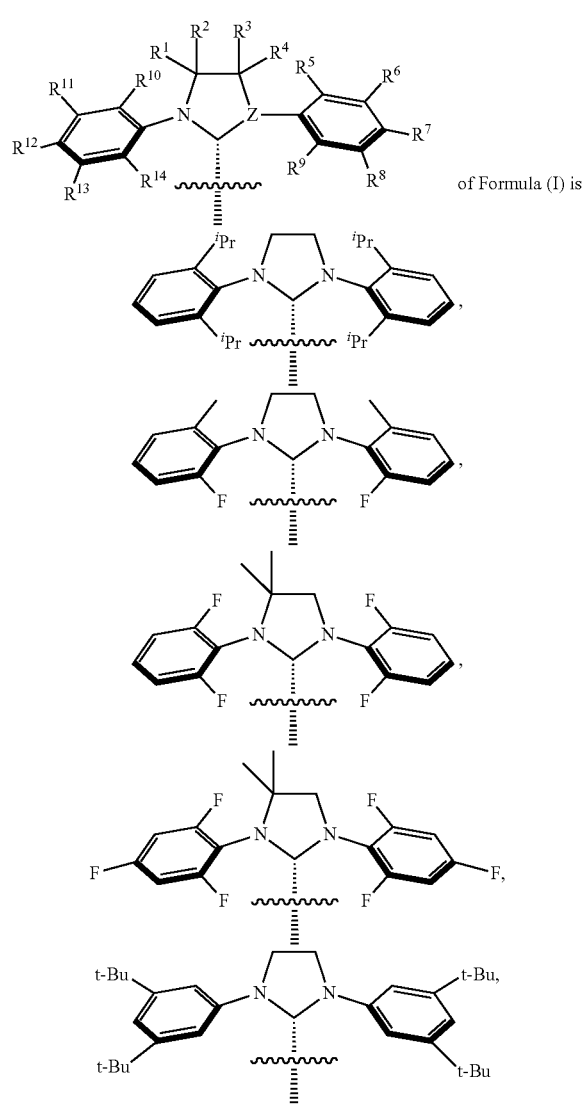
of Formula (I) is
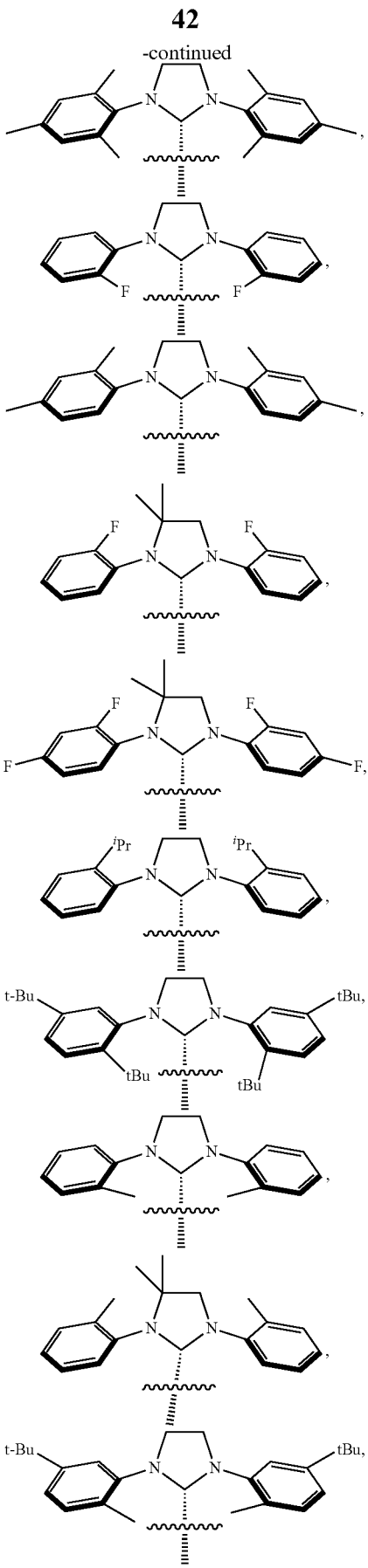

-continued
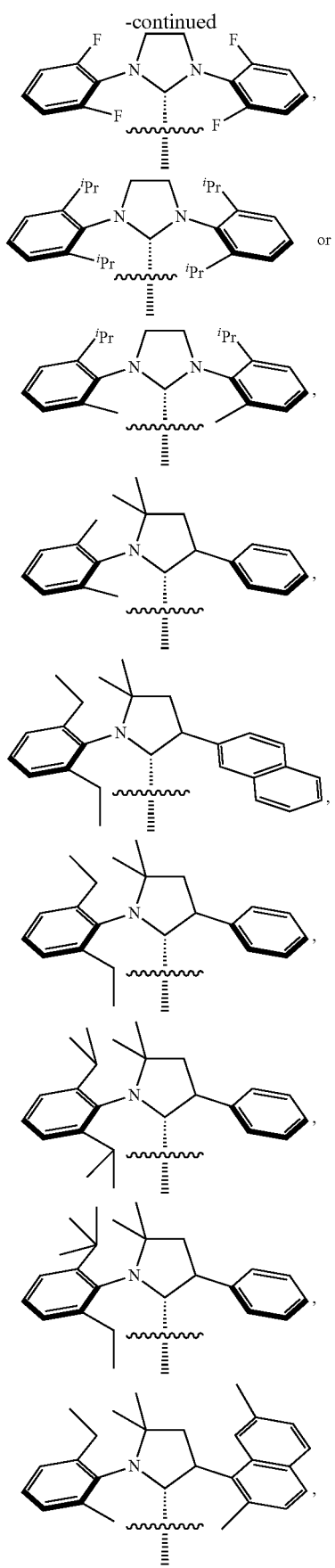
or
-continued
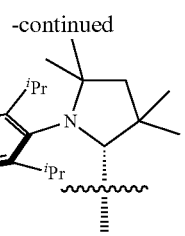
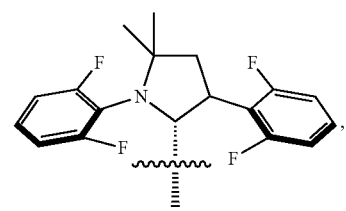
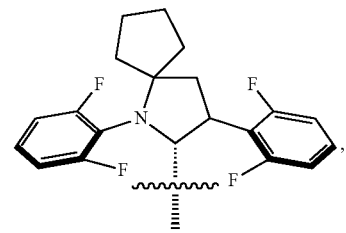
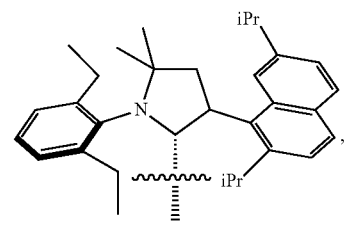
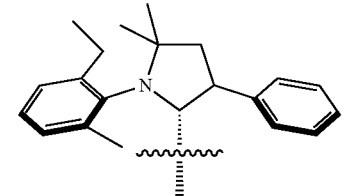
In one embodiment, the invention provides a compound of Formula (I) is selected from:
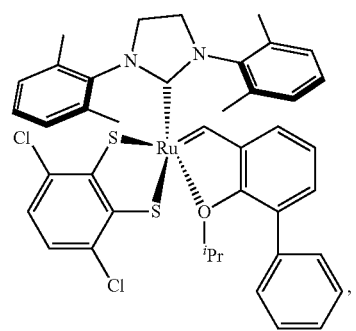

-continued
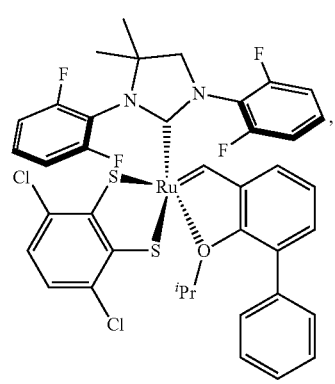
C857
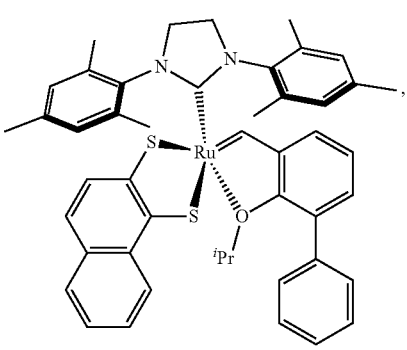
C823
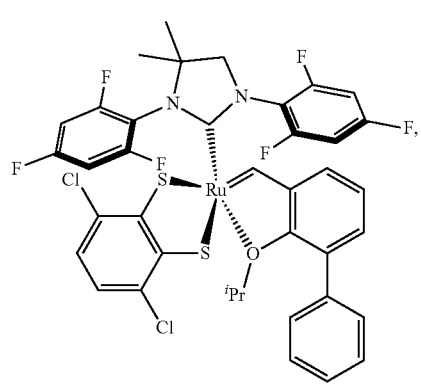
C894
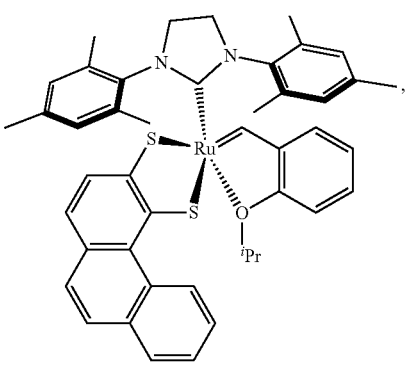
C797
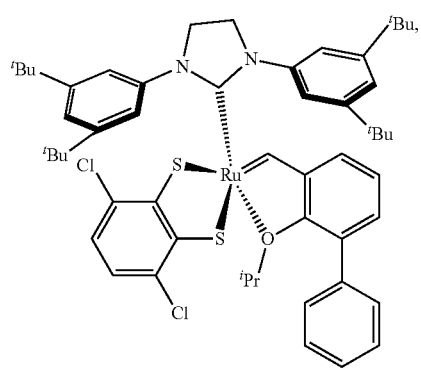
C881
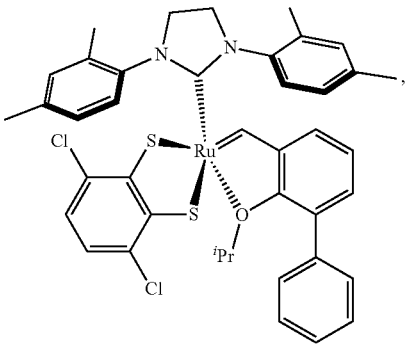
C813
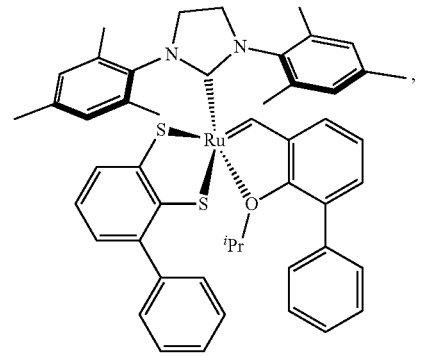
C849
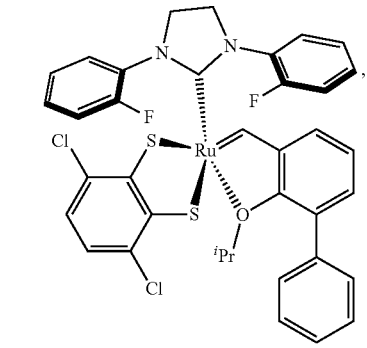
C793

C821
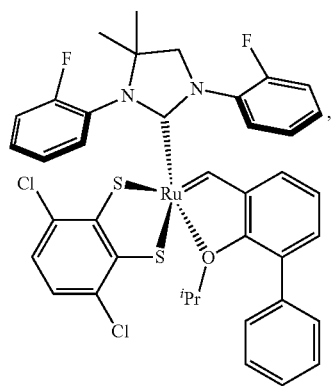
C782
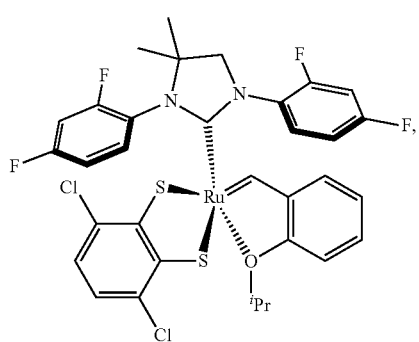
C841
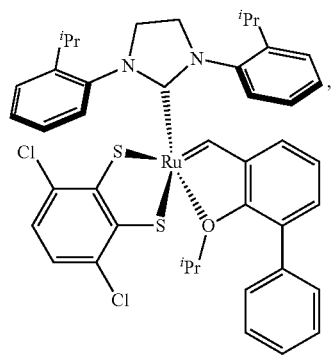
C982
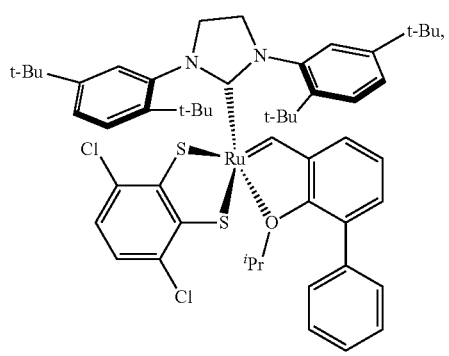
C785
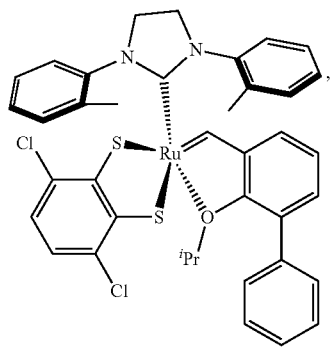
C814
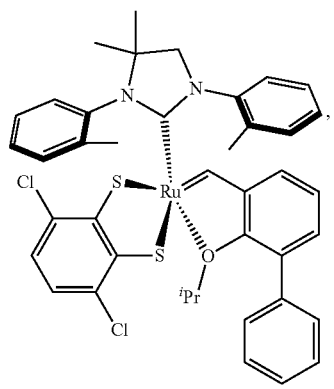
C814
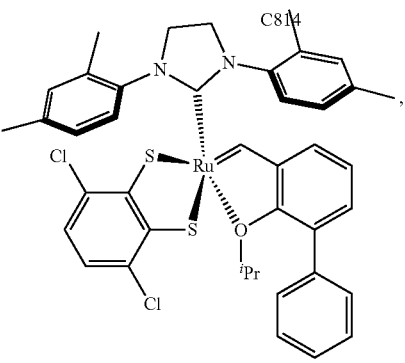
C786
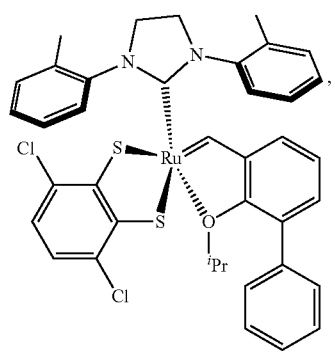

-continued
C842
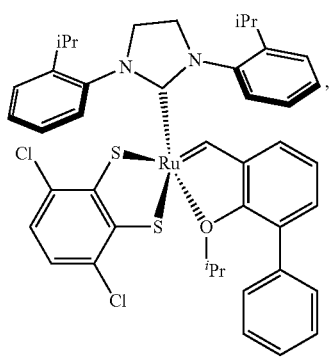
C753
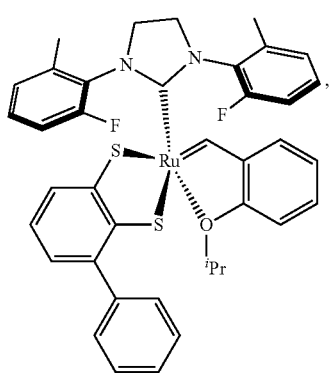
C727
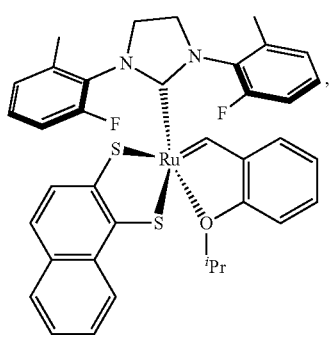
C821
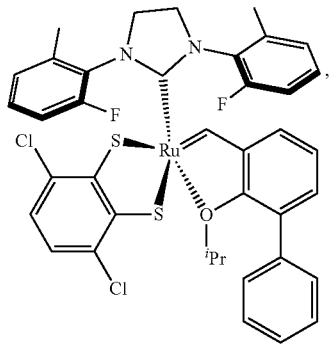
-continued
C864
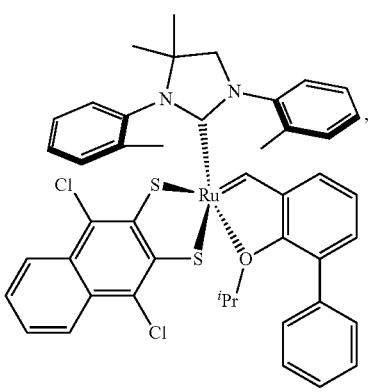
C777
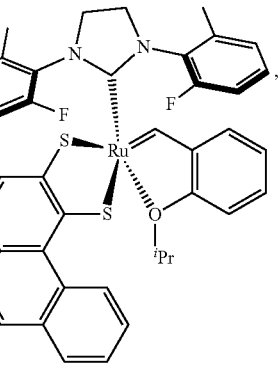
C789
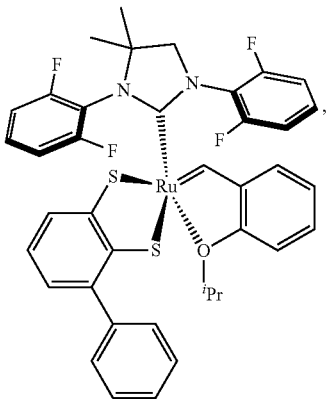
C892
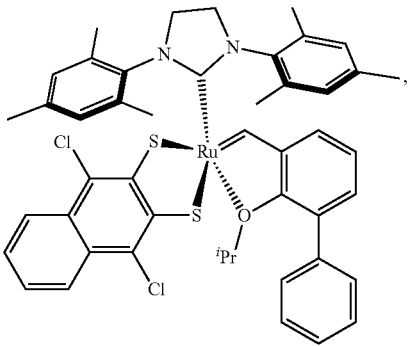

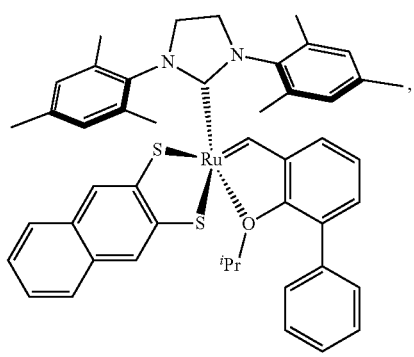
C823
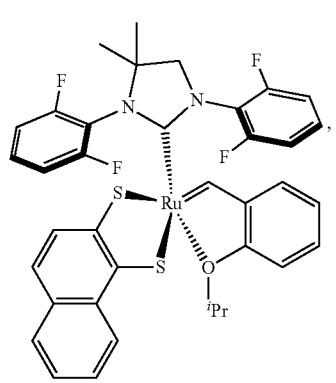
C763
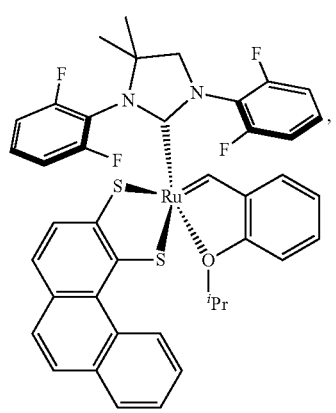
C813
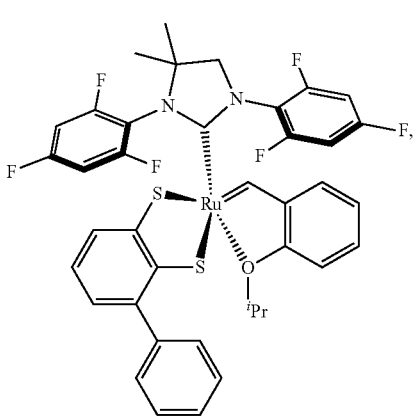
C825
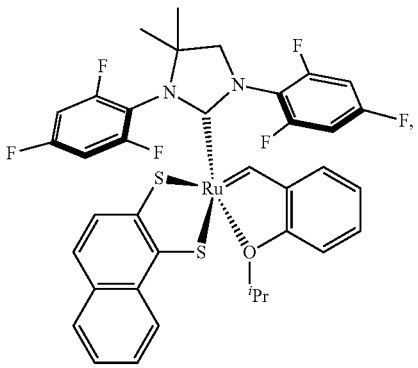
C799
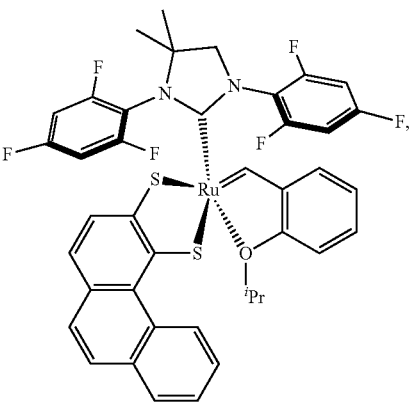
C849f
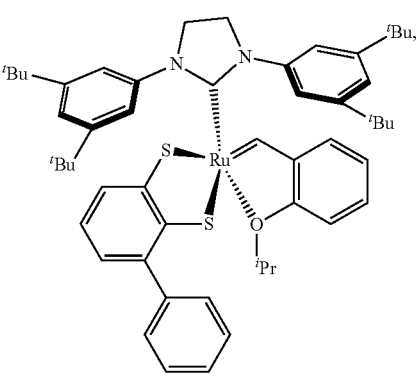
C912
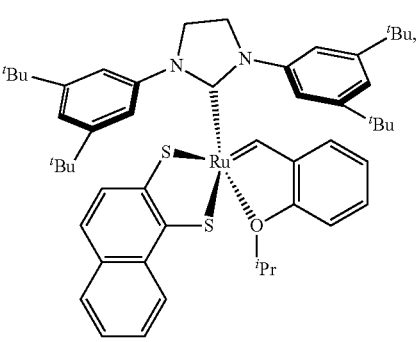
C886

C936
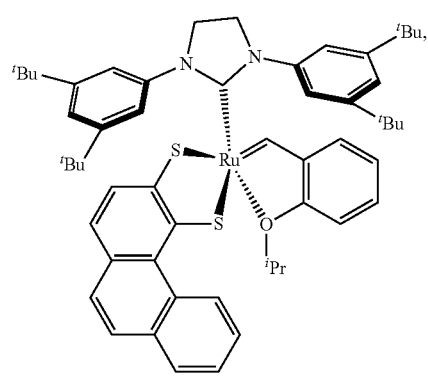
C857
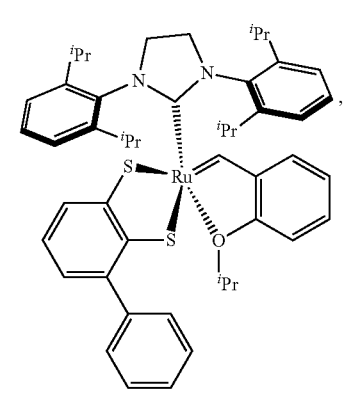
C831c
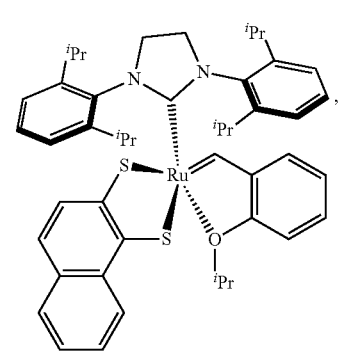
C881
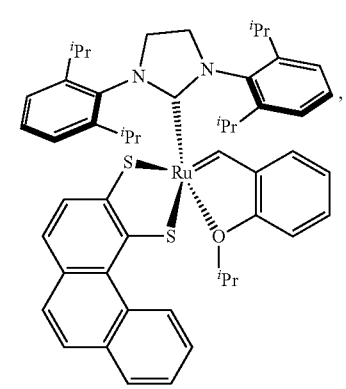
C789
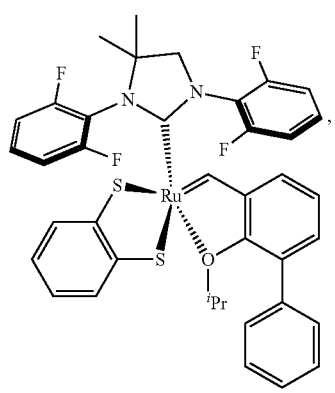
C820
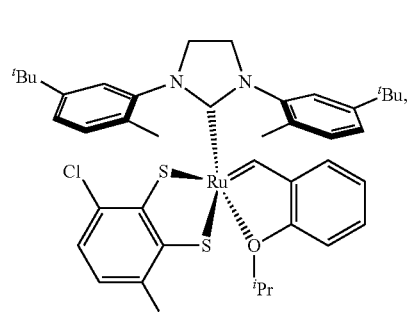
C896z
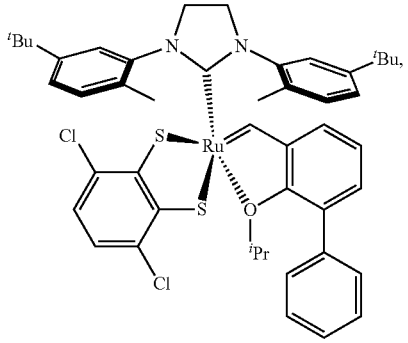
C827z
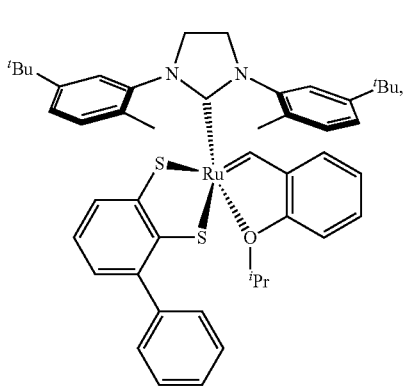

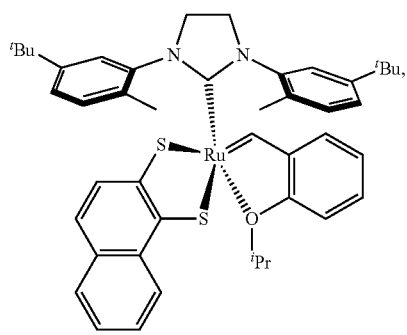
C801z
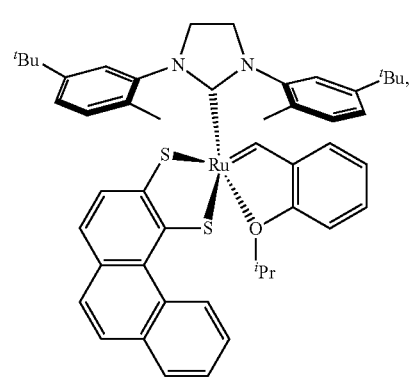
C853
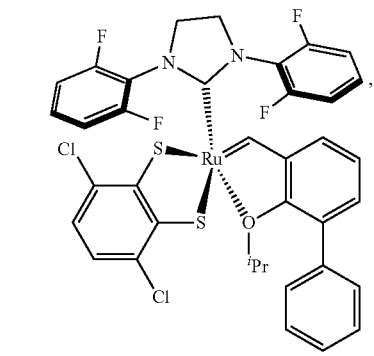
C830
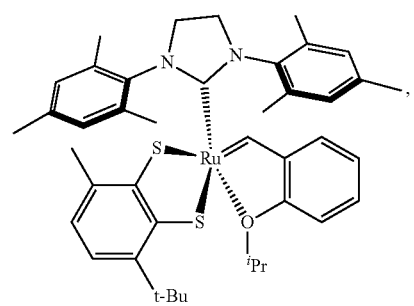
C767
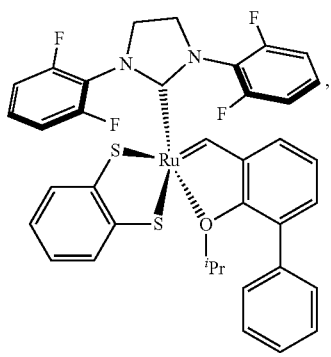
C761
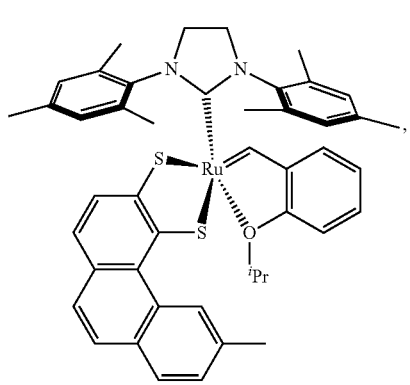
C811
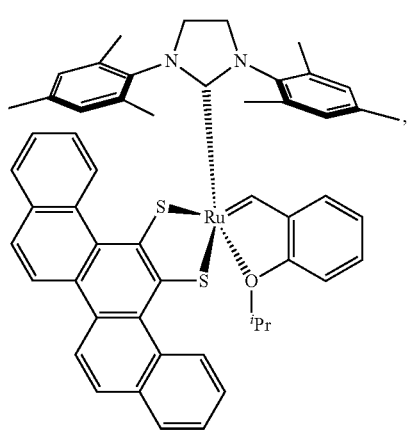
C897
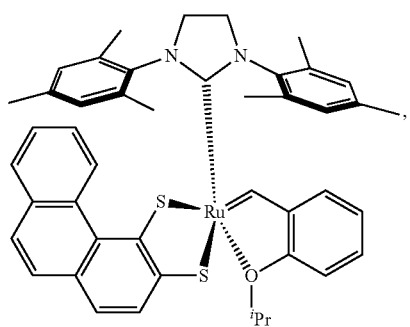
C797

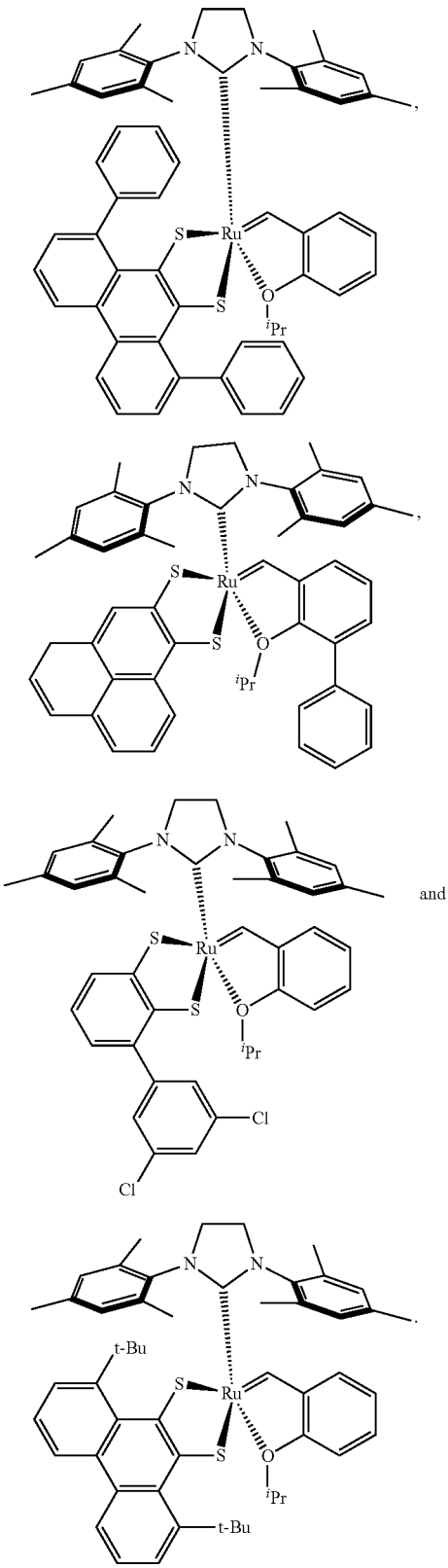

In one embodiment, the invention provides a Z-selective ruthenium olefin metathesis catalyst represented by the structure of Formula (V),

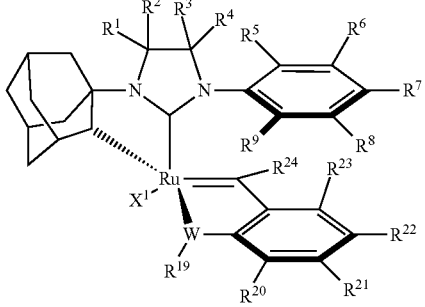

wherein,

W is O, halogen, $NR^{33}$ or S;

$X^1$ is hydrogen, halide, nitrate, optionally substituted $C_1$-$C_{20}$ alkyl, optionally substituted $C_5$-$C_{24}$ aryl, optionally substituted $C_1$-$C_{20}$ alkoxy, optionally substituted $C_1$-$C_{20}$ alkylcarboxylate, optionally substituted $C_5$-$C_{24}$ aryloxy, optionally substituted $C_2$-$C_{20}$ alkoxycarbonyl, optionally substituted $C_6$-$C_{24}$ aryloxycarbonyl, optionally substituted $C_6$-$C_{24}$ arylcarboxylate, optionally substituted $C_2$-$C_{24}$ acyl, optionally substituted $C_2$-$C_{24}$ acyloxy, optionally substituted $C_1$-$C_{20}$ alkylsulfonato, optionally substituted $C_5$-$C_{24}$ arylsulfonato, optionally substituted $C_1$-$C_{20}$ alkylsulfanyl, optionally substituted $C_5$-$C_{24}$ arylsulfanyl, optionally substituted $C_1$-$C_{20}$ alkylsulfinyl, or optionally substituted $C_5$-$C_{24}$ arylsulfinyl;

$R^1$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with R; or together with $R^4$ can form a polycyclic ring;

$R^2$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;

$R^3$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;

$R^4$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{1-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen. —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{25}$, —OR$^{26}$, CN, —NR$^{27}$R$^{28}$, NO$_2$, —CF$_3$. —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{19}$ is H, optionally substituted $C_{1-24}$ alkyl, —C($R^{34}$)($R^{35}$)COOR$^{36}$, —C($R^{34}$)($R^{35}$)C(O)H, —C($R^{34}$)($R^{35}$)C(O)R$^{37}$, —C($R^{34}$)($R^{35}$)CR$^{38}$(OR$^{39}$)(OR$^{40}$), —C($R^{34}$)($R^{35}$)C(O)NR$^{41}$R$^{42}$, —C($R^{34}$)($R^{35}$)C(O)NR$^{41}$OR$^{42}$, —C(O)R$^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{20}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring;

$R^{21}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, OR$^{30}$, NR$^{27}$R$^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is ii, optionally substituted $C_{1-24}$ alkyl, optionally substituted $C_{3-8}$ cycloalkyl, optionally substituted heterocycle, optionally substituted $C_{1-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, OR$^{26}$, —NR$^{27}$R$^{28}$, optionally substituted heterocycle, optionally substituted $C_{3-4}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$, cycloalkenyl, or together with R can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{36}$ is H, optionally substituted $C_{24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{38}$ is H, optionally substituted $C_{1-12}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-12}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

x is 1 or 2; and wherein the adamantyl can be optionally substituted by one or more $C_{1-6}$ alkyl groups.

In one embodiment, the invention provides a stereoretentive ruthenium olefin metathesis catalyst represented by the structure of Formula (V), wherein: W is O; $X^1$ is benzoate, pivalate, $C_1$-$C_6$ acyl, $C_2$-$C_6$ alkoxycarbonyl, $C_1$-$C_6$ alkyl, phenoxy, $C_1$-$C_6$ alkoxy, $C_1$-$C_6$ alkylsulfanyl, aryl, or $C_1$-$C_6$ alkylsulfonyl; $R^1$ is H, optionally substituted $C_{1-12}$ alkyl, halogen; $R^2$ is H, optionally substituted $C_{1-12}$ alkyl, halogen; $R^3$ is H, optionally substituted $C_{1-12}$ alkyl, halogen; $R^4$ is H, optionally substituted $C_{1-12}$ alkyl, halogen; $R^5$ is H, optionally substituted $C_{1-12}$ alkyl, halogen; $R^6$ is H, optionally substituted $C_{1-12}$ alkyl, halogen; $R^7$ is H, optionally substituted $C_{1-12}$ alkyl, halogen; $R^8$ is H, optionally substituted $C_{1-12}$ alkyl, halogen; $R^9$ is H, optionally substituted $C_{1-12}$ alkyl, halogen; $R^{19}$ is H, optionally substituted $C_{1-12}$ alkyl, —C($R^{34}$)($R^{35}$)—COOR$^{36}$, —C($R^{34}$)($R^{35}$)—C(O)H, —C($R^{34}$)($R^{35}$)—C(O)R$^{37}$, —C($R^{34}$)($R^{35}$)—CR$^{38}$(OR$^{39}$)(OR$^{40}$), —C($R^{34}$)($R^{35}$)—C(O)—NR$^{41}$R$^{42}$, —C($R^{34}$)($R^{35}$)—C(O)—NR$^{41}$OR$^{40}$, —C(O)R$^{25}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{33}$ can form an optionally substituted heterocyclic ring; $R^{20}$ is H, optionally substituted $C_{1-12}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ can form a polycyclic ring; $R^{21}$ is H, optionally substituted $C_{1-12}$ alkyl, halogen, —NR$^{27}$R$^{28}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{20}$ or together with $R^{22}$ can form a polycyclic ring; $R^{22}$ is H, optionally substituted $C_{1-12}$ alkyl, halogen, —C(O)R$^{25}$—, OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted $C_{3-8}$ cycloalkyl, optionally substituted $C_{6-10}$ aryl, optionally substituted $C_{3-8}$ cycloalkenyl or together with $R^{21}$ or together with $R^{23}$ can form a polycyclic ring; $R^{23}$ is H, optionally substituted $C_{1-12}$ alkyl, halogen, optionally substituted heterocycle, optionally substituted $C_{3-8}$ cycloalkyl, optionally substituted $C_{6-10}$ aryl or optionally substituted $C_{3-8}$ cycloalkenyl or together with $R^{22}$ can form a polycyclic ring; $R^{24}$ is H; $R^{25}$ is OH, OR$^{30}$, NR$^{27}$R$^{28}$, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{26}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{27}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{28}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{29}$ is H, optionally substituted $C_{1-12}$ alkyl, OR, —NR$^{27}$R$^{28}$, optionally substituted heterocycle, optionally substituted $C_{3-8}$ cycloalkyl, optionally substituted $C_{6-10}$ aryl or optionally substituted $C_{3-8}$ cycloalkenyl; $R^{30}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{31}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{32}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{33}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl, or together with $R^{19}$ can form an optionally substituted heterocyclic ring; $R^{34}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-4}$ cycloalkenyl; $R^{35}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{36}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{37}$ is optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{38}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{39}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{40}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{41}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; $R^{42}$ is H, optionally substituted $C_{1-12}$ alkyl, optionally substituted $C_{3-8}$ cycloalkyl, optionally substituted heterocycle, optionally substituted $C_{6-10}$ aryl or optionally substituted $C_{3-8}$ cycloalkenyl; x is 1 or 2; and wherein the adamantyl can be optionally substituted by one or more $C_{1-6}$ alkyl groups.

In another embodiment, the invention provides a catalyst represented by Formula (V) wherein: W is O; $X^1$ is CF$_3$CO$_2$, CH$_3$CO$_2$, CH$_3$CH$_2$CO$_2$, CFH$_2$CO$_2$, (CH$_3$)$_3$CO$_2$, (CH$_3$)$_2$CHCO$_2$, (CF$_3$)$_2$(CH$_3$)CO$_2$, (CF$_3$)(CH$_3$)$_2$CO$_2$, benzoate, naphthylate, tosylate, mesylate, or trifluoromethanesulfonate; $R^1$ is H, linear or branched $C_{1-6}$ alkyl, or halogen; $R^2$ is H linear or branched $C_{1-6}$ alkyl, or halogen; $R^3$ is H, linear or branched $C_{1-6}$ alkyl, or halogen; $R^4$ is H, linear or branched $C_{1-6}$ alkyl or halogen; $R^5$ is H, linear or branched $C_{1-6}$ alkyl; $R^6$ is linear or branched $C_{1-6}$ alkyl; $R^7$ is H, linear or branched $C_{1-6}$ alkyl; $R^8$ is H or $C_{1-6}$ alkyl; $R^9$ is H, linear or branched $C_{1-6}$ alkyl; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)R$^{37}$, —C($R^{34}$)($R^{35}$) CR$^{38}$(OR$^{39}$)(OR$^{40}$), —C($R^{34}$)($R^{35}$) C(O) NR$^{41}$R$^{42}$, —C($R^{34}$)($R^{35}$) C(O) NR$^{41}$OR$^{40}$ or together with $R^{33}$ forms a five, six or seven membered heterocyclic ring; $R^{20}$ is H, linear or branched. $C_{1-6}$ alkyl, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, cyclohexene or together with $R^{21}$ can form a polycycle; $R^{21}$ is H, phenyl, —NR$^{27}$R$^{28}$, linear or branched $C_{1-6}$ alkyl, halogen or together with $R^{20}$ or together with $R^{22}$ can form a polycycle; $R^{22}$ is H, linear or branched $C_{1-6}$ alkyl, halogen, —C(O)R$^{25}$, —OR$^{26}$, CN, —NR$^{27}$R$^{28}$, NO$_2$, —CF$_3$, —S(O)$_x$ R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, cyclohexene or together with $R^{21}$ or together with $R^{23}$ can form a polycycle; $R^{23}$ is H, phenyl, linear or branched $C_{1-6}$ alkyl or together with $R^{22}$ can form a polycycle; $R^{24}$ is H, linear or branched $C_{1-6}$ alkyl; $R^{25}$ is OH, OR$^{30}$, NR$^{27}$R$^{28}$, linear or branched. $C_{1-6}$ alkyl; $R^{26}$ is H, linear or branched $C_{1-6}$ alkyl; $R^{27}$ is H, linear or branched $C_{1-6}$ alkyl; $R^{25}$ is H, linear or branched $C_{1-6}$ alkyl; $R^{29}$ is H, linear or branched $C_{3-6}$ alkyl, —NR$^{27}$R$^{28}$; $R^{30}$ is optionally substituted $C_{1-6}$ alkyl, optionally substituted $C_{3-8}$ cycloalkyl, optionally substituted heterocycle, optionally substituted phenyl or optionally substituted $C_{3-8}$ cycloalkenyl; $R^{31}$ is H, linear or branched $C_{1-6}$ alkyl; $R^{32}$ is H, linear or branched $C_{1-6}$ alkyl; $R^{33}$ is H, linear or branched $C_{1-6}$ alkyl, or together with $R^{19}$ forms a five, six or seven membered heterocyclic ring; $R^{34}$ is H, or linear or branched $C_{1-6}$ alkyl; $R^{35}$ is H, or linear or branched $C_{1-6}$ alkyl; $R^{35}$ is H, linear or branched $C_{1-6}$ alkyl; $R^{31}$ is linear or branched $C_{1-6}$ alkyl; $R^{38}$ is H or linear or branched $C_{1-6}$ alkyl; $R^{39}$ is H, linear or branched $C_{1-6}$ alkyl; $R^{40}$ is H, linear or branched $C_{1-6}$ alkyl; $R^{41}$ is H, linear or branched $C_{1-6}$ alkyl; $R^{42}$ is H, linear or branched $C_{1-6}$ alkyl; x is 1 or 2; and wherein the adamantyl can be optionally substituted by one or more $C_{1-6}$ alkyl groups.

In one embodiment, the invention provides a catalyst represented by Formula (V) wherein: W is O; $X^1$ is CF$_3$CO$_2$, CH$_3$CO$_2$, CH$_3$CH$_2$CO$_2$, CFH$_2$CO$_2$, (CH$_3$)$_3$CO$_2$, (CH$_3$)$_2$CHCO$_2$, (CF$_3$)$_2$(CH$_3$)CO$_2$, (CF$_3$)(CH$_3$)$_2$CO$_2$, benzoate, naphthylate, tosylate, mesylate, or trifluoromethanesulfonate; $R^1$ is Me, Et, i-Pr, n-Pr, n-Bu, t-Bu, s-Bu or H; $R^2$ is Me, Et, i-Pr, n-Pr, n-Bu, t-Bu, s-Bu or H; $R^3$ is H, Me, Et, i-Pr, n-Pr, n-Bu, t-Bu, or s-Bu; $R^4$ is H, Me, Et, i-Pr, n-Pr, n-Bu, t-Bu, or s-Bu; $R^4$ is H, F, Cl, Br, I, Me, Et, i-Pr, n-Pr, n-Bu, t-Bu, or s-Bu; $R^6$ is H, F, Cl, Br, I, Me, Et, i-Pr, n-Pr, n-Bu, t-Bu, or s-Bu; $R^7$ is H, F, Cl, Br, I, Me, Et, i-Pr, n-Pr, n-Bu, t-Bu, or s-Bu; $R^8$ is H, F, Cl, Br, I, Me, Et, i-Pr, n-Pr, n-Bu, t-Bu, or s-Bu; $R^9$ is H, F, Cl, Br, I, Me, Et, i-Pr, n-Pr, n-Bu, t-Bu, or s-Bu; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)R$^{37}$, —C($R^{34}$)($R^{35}$) CR$^{38}$(OR$^{39}$)(R$^{40}$), —C($R^{34}$)($R^{35}$) C(O) NR$^{41}$R$^{42}$, —C($R^{34}$)($R^{35}$) C(O) NR$^{41}$OR$^{40}$; $R^{20}$ is H, F, Cl, Br, I, Me, Et, i-Pr, n-Pr, n-Bu, t-Bu, s-Bu, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, pyridine, piperidine, imidazole, indolizine, indazole, optionally substituted $C_{3-8}$ cycloalkyl, phenyl, naphthalene, or cyclohexene; $R^{21}$ is H, phenyl, Me, Et, i-Pr, n-Pr, n-Bu, t-Bu, s-Bu, —NR$^{27}$R$^{28}$F, Cl, Br, or I; $R^{22}$ is H, —C(O)R$^{25}$, —OR$^{26}$, CN, —NR$^{27}$R$^{28}$, NO$_2$, —CF$_3$, —S(O)$_x$R$^{29}$, —P(O)(OH)$_2$. —OP(O)(OH)$_2$, or —SR$^{31}$; $R^{23}$ is H, F, Cl, Br, I, phenyl, Me, Et, i-Pr, n-Pr, n-Bu, t-Bu, or s-Bu; $R^{24}$ is H; $R^{24}$ is H or Me; $R^{25}$ is OH, OR, NR$^{27}$R$^{28}$, Me, Et, or i-Pr; $R^{26}$ is H, Me, Et, i-Pr, n-Pr, n-Bu, t-Bu, or s-Bu; $R^{27}$ is H. Me, Et. or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —NR$^{27}$R$^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu. or s-Bu; $R^{32}$ is Me, Et, n-Pr or H; $R^{33}$ is H, Me, Et, Me, Et, i-Pr, n-Pr, n-Bu, t-Bu, s-Bu, or together with $R^{19}$ forms a morpholino, a thio-morpholino, a pyrrolidino, a piperidino, or a piperazino ring; $R^{34}$ is H, Me, Et, i-Pr, n-Pr, n-Bu, t-Bu, or s-Bu; $R^{35}$ is H, or Me, Et, i-Pr, n-Pr, n-Bu, t-Bu, or s-Bu; $R^{36}$ is H, Me, Et, i-Pr, n-Pr, n-Bu, t-Bu, or s-Bu; $R^{37}$ is Me, Et, i-Pr, n-Pr, n-Bu, t-Bu, or s-Bu; $R^{38}$ is H or Me, Et, i-Pr, n-Pr, n-Bu, t-Bu, or s-Bu; $R^{39}$ is H, Me, Et, i-Pr, n-Pr, n-Bu, t-Bu, or s-Bu; $R^{40}$ is H, Me, Et, i-Pr, n-Pr, n-Bu, t-Bu, or s-Bu; $R^{41}$ is H, Me, Et, i-Pr, n-Pr, n-Bu, t-Bu, or s-Bu; $R^{42}$ is H, Me, Et, i-Pr, n-Pr, n-Bu, t-Bu, or s-Bu; x is 1 or 2; and wherein the adamantyl can be optionally substituted by one or more Me groups.

In one embodiment, the invention provides a catalyst represented by Formula (V) wherein: W is O; $X^1$ is nitrate; $R^1$ is H; $R^2$ is H; $R^3$ is H; $R^4$ is H; $R^5$ is H, F, Me, Et, or i-Pr; $R^6$ is H, F, Me, Et, or i-Pr; $R^7$ is H. F, Me, Et, or i-Pr; $R^8$ is H, F, Me, Et, or i-Pr; $R^9$ is H, F, Me, Et, or i-Pr; $R^{19}$ is H, phenyl, $C_{1-6}$ alkyl, —C($R^{34}$)($R^{35}$) COOR$^{36}$, —C($R^{34}$)($R^{35}$) C(O)H, —C($R^{34}$)($R^{35}$) C(O)R$^{37}$, —C($R^{34}$)($R^{35}$) CR$^{38}$(OR$^{39}$)(OR$^{40}$), —C($R^{34}$)($R^{35}$) C(O) NR$^{41}$R$^{42}$, —C($R^{34}$)($R^{35}$) C(O) NR$^{41}$OR$^{40}$; $R^{20}$ is H, F, Me, Et, or i-Pr, $R^{21}$ is H, F, Me, Et, or i-Pr, $R^{22}$ is H, —C(O)R$^{25}$, —OR$^{26}$, CN. —NR$^{27}$R$^{28}$, NO$_2$, —CF$_3$, —S(O)$_x$R$^{29}$, —P(O)OH)$_2$, —OP(O)(OH)$_2$, or —SR$^{31}$; $R^{23}$ is H, F, Me, Et, or i-Pr; $R^{24}$ is H; $R^{25}$ is OH, OR$^{30}$, NR$^{27}$R$^{28}$, Me, Et, or i-Pr; $R^{26}$ is H, Me, Et, i-Pr, n-Pr, n-Bu, t-Bu, or s-Bu; $R^{27}$ is H, Me, Et, or i-Pr; $R^{28}$ is H, Me, Et, i-Pr, n-Pr, n-Bu, t-Bu, or s-Bu; $R^{29}$ is H, Me, Et, i-Pr, n-Pr, n-Bu, t-Bu, s-Bu, or —NR$^{27}$R$^{28}$; $R^{30}$ is Me, Et, i-Pr, n-Pr, n-Bu, t-Bu, or s-Bu; $R^{31}$ is H, Me, Et, i-Pr, n-Pr, n-Bu, t-Bu. or s-Bu; $R^{32}$ is Me, Et, n-Pr or H; $R^{34}$ is H, F, Me, Et, or i-Pr; $R^{35}$ is H, F, Me, Et, or i-Pr; $R^{36}$ is H, F, Me, Et, or i-Pr; $R^{37}$ is Me, Et, i-Pr, n-Pr, n-Bu, t-Bu, or s-Bu; $R^{38}$ is H. F, Me, Et, or i-Pr; $R^{39}$ is H, F, Me, Et, or i-Pr; $R^{40}$ is H, F, Me, Et, or i-Pr; $R^{41}$ is H, F, Me, Et, or i-Pr, and $R^{42}$ is H, F, Me, Et, or i-Pr.

In one embodiment, the invention provides a catalyst represented by Formula (V) wherein: W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{23}$ is H; $R^{24}$ is H.

In one embodiment, the invention provides a catalyst represented by Formula (V) wherein: W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a compound of Formula (V) is selected from:

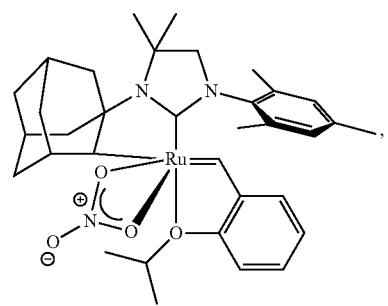

-continued

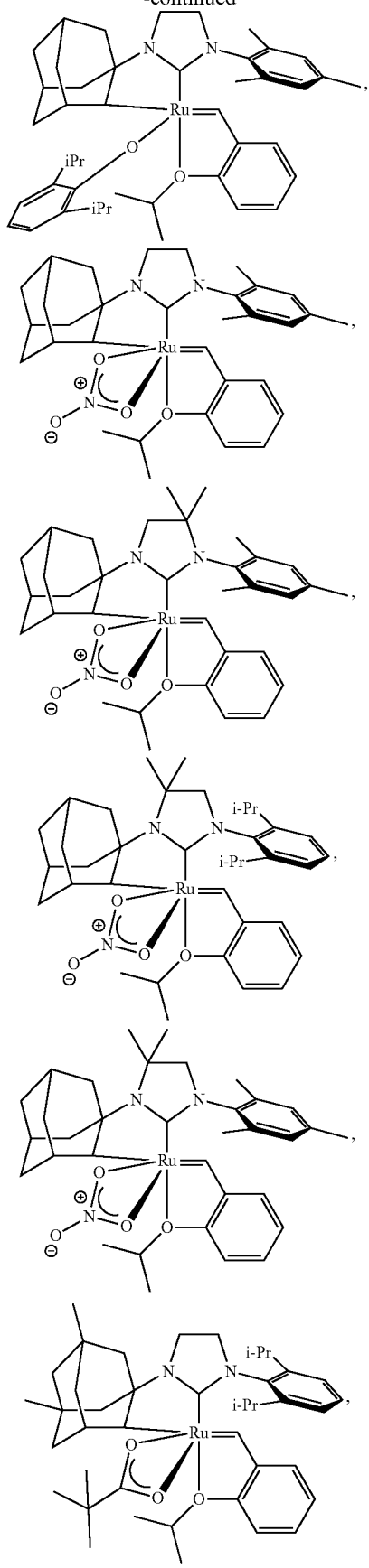

-continued

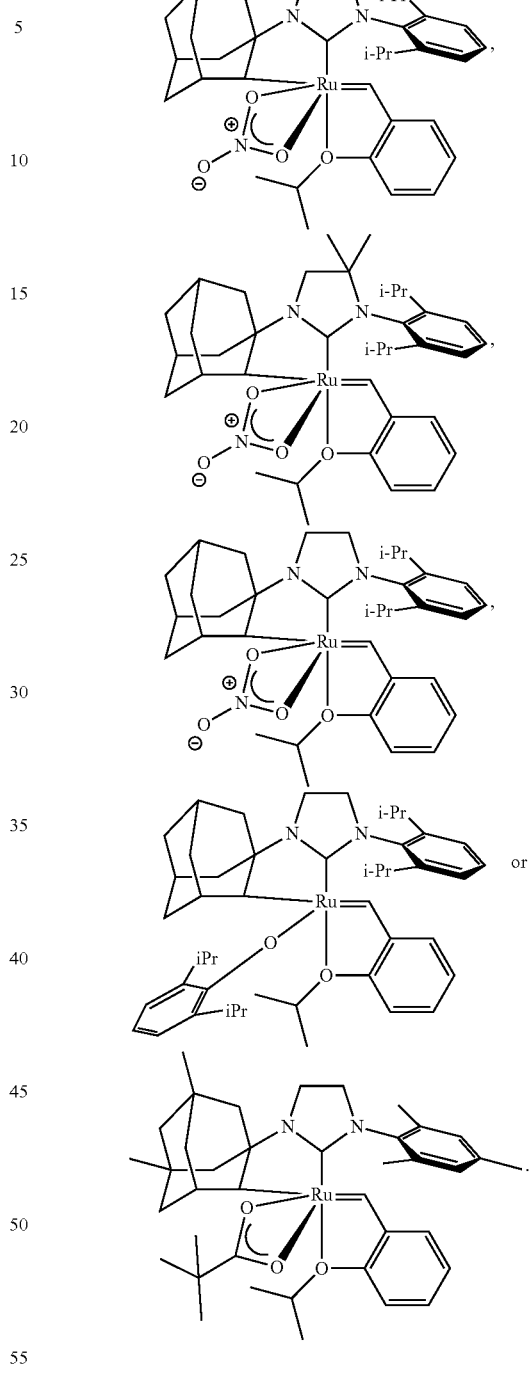

It will be appreciated that the amount of catalyst that is used (i.e., the "catalyst loading") in the reaction is dependent upon a variety of factors such as the identity of the reactants and the reaction conditions that are employed. It is therefore understood that catalyst loading may be optimally and independently chosen for each reaction. In general, however, the catalyst will be present in an amount that ranges from a low of about 0.1 ppm, 1 ppm, or 5 ppm, to a high of about 10 ppm, 15 ppm, 25 ppm, 50 ppm, 100 ppm, 200 ppm, 500 ppm, or 1000 ppm relative to the amount of an olefinic substrate.

The catalyst will generally be present in an amount that ranges from a low of about 0.00001 mol %, 0.0001 mol %, or 0.0005 mol %, to a high of about 0.001 mol %, 0.0015 mol %, 0.0025 mol %, 0.005 mol %, 0.01 mol %, 0.02 mol %, 0.05 mol %, or 0.1 mol % relative to the olefinic substrate.

When expressed as the molar ratio of olefin to catalyst, the catalyst (the "olefin to catalyst ratio"), loading will generally be present in an amount that ranges from a low of about 10,000,000:1, 1,000,000:1, 500,000:1 or 200,00:1, to a high of about 100,000:1 60,000:1, 50,000:1, 45,000:1, 40,000:1, 30,000:1, 20,000:1, 10,000:1, 5,000:1, or 1,000:1.

EMBODIMENTS

These and other aspects of the invention will be apparent to the skilled artisan in light of the following detailed description and examples.

The invention provides a method that produces a compound (i.e., a product, olefin product; e.g., cross-metathesis product) having at least one carbon-carbon double bond (e.g., a product internal olefin) in a Z/E selectivity ratio of 95/5, or 96/4, or 97/3, or 98/2, or 99/1. In some cases, 100% of the at least one carbon-carbon double bond produced in the cross-metathesis reaction has a Z-configuration.

In one embodiment, the invention provides a method for producing at least one Δ$^{12}$-Prostaglandin J product represented by Formula (IV),

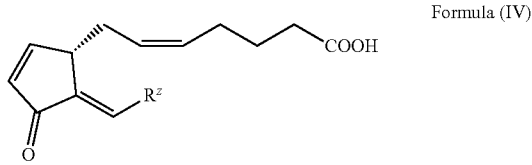

Formula (IV)

wherein: R$^z$ is selected from

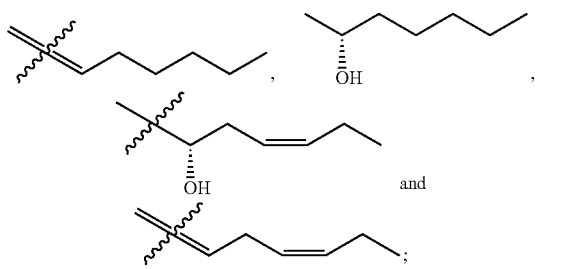

and wherein at least one carbon-carbon double bond has a Z/E-selectivity of 95/5, or 96/4, or 97/3, or 98/2, or 99/1, or >99/<1; comprising submitting an alcohol product of Formula (III)

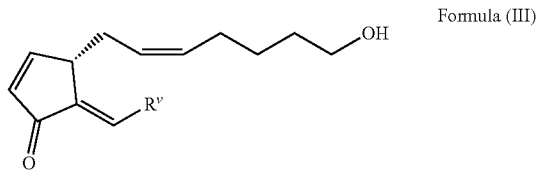

Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

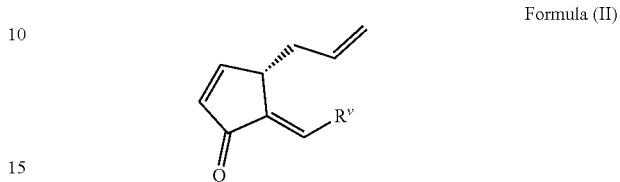

Formula (II)

and cis-octen-1-ol in the presence of a stereoretentive ruthenium olefin metathesis catalyst represented by Formula (I) or in the presence of a Z-selective ruthenium olefin metathesis catalyst represented by Formula (V); wherein R$^v$ is selected from

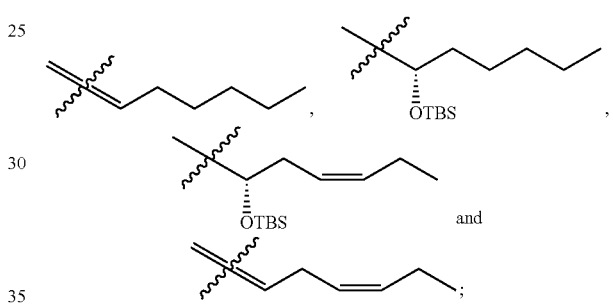

and wherein the stereoretentive ruthenium olefin metathesis catalyst represented by Formula (I) is

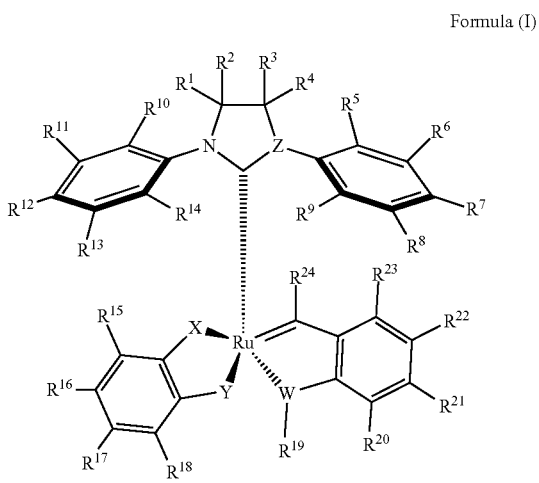

Formula (I)

X is O or S;
Y is O or S;
Z is N or CR$^{32}$;
W is O, halogen, NR$^{33}$ or S;
R$^1$ is H, optionally substituted C$_{1-24}$ alkyl, halogen, —C(O)R$^{25}$, —OR$^{16}$, CN, —NR$^{27}$R$^{28}$, NO$_2$, —CF$_3$, —S(O)$_x$R$^{29}$, —P(O)(OH)$_2$, —OP(O)(OH)$_2$. —SR$^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;

$R^2$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;

$R^3$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;

$R^4$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-12}$ alkyl, halogen, —C(O) $R^{25}$, —$OR^{26}$, CN, —$NR^{27}R^{28}$, $NO_2$. —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^7$ or together with $R^9$ can form an optionally substituted polycyclic ring;

$R^8$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{10}$ is H, optionally substituted $C_{1-24}$ alkyl, halogen, —C(O) $R^{25}$, —$OR^{26}$, CN, —$NR^{27}R^{28}$, $NO_2$, —$CF_3$, —S(O)R, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring;

$R^{17}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$, cycloalkenyl, or together with $R^{18}$ or together with $R^{16}$ can form an optionally substituted polycyclic ring;

$R^{18}$ is H, optionally substituted $C_{1-24}$ alkyl, halogen, —C(O) $R^{25}$, —$OR^{26}$, CN, —$NR^{27}R^{28}$, $NO_2$, —$CF_3$, —$S(O)_xR^{29}$, —$P(O)(OH)_2$, —$OP(O)(OH)_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{17}$ can form an optionally substituted polycyclic ring;

$R^{19}$ is H, optionally substituted $C_{1-24}$ alkyl, —$C(R^{34})(R^{35})$ $COOR^{36}$, —$C(R^{34})(R^{35})C(O)H$, —$C(R^{34})(R^{35})C(O)R^{37}$, —$C(R^{34})(R^{35})CR^{38}(OR^{39})(OR^{40})$, —$C(R^{34})(R^{35})C(O)$ $NR^{41}R^{42}$, —$C(R^{34})(R^{35})C(O)NR^{41}OR^{40}$, —$C(O)R^{25}$, optionally substituted heterocycle, optionally substituted $C_{3-8}$ cycloalkyl, optionally substituted $C_{5-24}$ aryl, optionally substituted C$_{3-8}$ cycloalkenyl, or together with R$^{33}$ can form an optionally substituted heterocyclic ring or is nil when W is halogen;

R$^{20}$ is H, optionally, substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{21}$ can form a polycyclic ring;

R$^{21}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{20}$ or together with R$^{22}$ can form a polycyclic ring;

R$^{22}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{21}$ or together with R$^{23}$ can form a polycyclic ring;

R$^{23}$ is H, optionally substituted C$_{1-24}$ alkyl, halogen, —C(O)R$^{25}$, —OR$^{26}$, NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{22}$ can form a polycyclic ring;

R$^{24}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl;

R$^{25}$ is OH, OR$^{30}$, NR$^{27}$R$^{28}$, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl, R$^{26}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{27}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{28}$ is H, optionally substituted C$_{1-12}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{29}$ is H, optionally substituted C$_{1-24}$ alkyl, OR$^{26}$, —NR$^{27}$R$^{28}$, optionally substituted heterocycle, optionally substituted C$_{3-8}$ cycloalkyl, optionally substituted C$_{5-24}$ aryl or optionally substituted C$_{3-8}$ cycloalkenyl;

R$^{30}$ is optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{31}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{32}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{33}$ is H, optionally substituted C$_{1-24}$ alkyl, optionally substituted C$_{3-8}$ cycloalkyl, optionally substituted heterocycle, optionally substituted C$_{5-24}$ aryl, optionally substituted C$_{3-8}$ cycloalkenyl, or together with R$^{19}$ can form an optionally substituted heterocyclic ring;

R$^{34}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{35}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{36}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl:

R$^{37}$ is optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{38}$ is H, optionally substituted C$_{1-12}$ alkyl, optionally substituted C$_{3-8}$ cycloalkyl, optionally substituted heterocycle, optionally substituted C$_{5-24}$ aryl or optionally substituted CM cycloalkenyl;

R$^{39}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{40}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{41}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{42}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

x is 1 or 2; and wherein the Z-selective ruthenium olefin metathesis catalyst represented by Formula (V) is

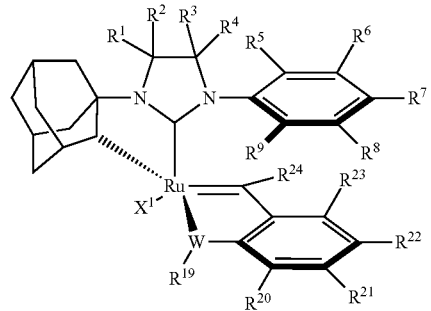

Formula (V)

wherein:
W is O, halogen, NR$^{33}$ or S;
X$^1$ is hydrogen, halide, nitrate, optionally substituted C$_1$-C$_{20}$ alkyl, optionally substituted C$_5$-C$_{24}$ aryl, optionally substituted $C_1$-$C_{20}$ alkoxy, optionally substituted $C_1$-$C_{20}$ alkylcarboxylate, optionally substituted $C_5$-$C_{24}$ aryloxy, optionally substituted $C_2$-$C_{20}$ alkoxycarbonyl, optionally substituted $C_6$-$C_{24}$ aryloxycarbonyl, optionally substituted $C_6$-$C_{24}$ arylcarboxylate, optionally substituted $C_2$-$C_{24}$ acyl, optionally substituted $C_2$-$C_{24}$ acyloxy, optionally substituted $C_1$-$C_{20}$ alkylsulfonato, optionally substituted $C_5$-$C_{24}$ arylsulfonato, optionally substituted $C_1$-$C_{20}$ alkylsulfanyl, optionally substituted $C_5$-$C_{24}$ arylsulfanyl, optionally substituted $C_1$-$C_{20}$ alkylsulfinyl, or optionally substituted $C_5$-$C_{24}$ arylsulfinyl;

$R^1$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;

$R^2$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^2$ can form a spiro compound or together with $R^3$ or together with $R^4$ can form a polycyclic ring;

$R^3$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;

$R^4$ is H, optionally substituted $C_{1-24}$ alkyl, halogen, —C(O)$R^2$—, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{1-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-4}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$—$SR^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring:

$R^8$ is H, optionally substituted $C_{1-24}$ alkyl, halogen, —C(O)$R^{25}$, —$OR^{26}$CN, $NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted. $C_{5-24}$ aryl, optionally substituted $C_{3-8}$ cycloalkenyl, or together with $R^8$ can form an optionally substituted polycyclic ring;

$R^{19}$ is H, optionally substituted $C_{1-24}$ alkyl; —C($R^{34}$)($R^{35}$)COO$R^{36}$, —C($R^{34}$)($R^{35}$)C(O)H, —C($R^{34}$)($R^{35}$)C(O)$R^{37}$, —C($R^{34}$)($R^{35}$)C$R^{38}$(O$R^{39}$)(O$R^{40}$), —C($R^{34}$)($R^{35}$)C(O)$NR^{41}R^{42}$, —C($R^{34}$)($R^{35}$)C(O)$NR^{41}OR^{40}$, —C(O)$R^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;

$R^{21}$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-6}$ cycloalkyl, optionally substituted $C_{5-24}$ aryl, optionally substituted $C_{3-8}$ cycloalkenyl or together with $R^{21}$ can form a polycyclic ring;

$R^{21}$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^2$ can form a polycyclic ring;

$R^{23}$ is H, optionally substituted $C_{1-2}$ alkyl, halogen, —C(O)$R^{25}$, —$OR^{26}$, CN, —$NR^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —$OR^{26}$, CN, —$NR^{27}R^{28}$, $NO_2$, —$CF_3$, —S(O)$_xR^{29}$, —(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, $OR^{30}$, $NR^{27}R^{28}$, optionally substituted $C_{1-24}$ alkyl, optionally substituted $C_3$ cycloalkyl, optionally substituted heterocycle, optionally substituted $C_{5-24}$ aryl or optionally substituted $C_{3-8}$ cycloalkenyl, $R^{26}$ is H, optionally substituted $C_{3-8}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, $OR^{26}$, $-NR^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-12}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-12}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$, cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl:

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

In one embodiment, the invention provides a method for producing at least one alcohol product represented by Formula (III)

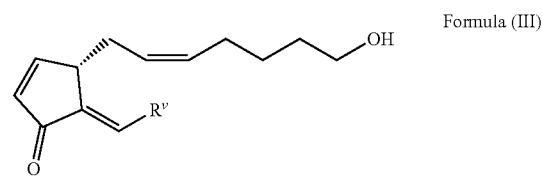

Formula (III)

wherein at least one carbon-carbon double bond has a Z/E-selectivity of 95/5, or 96/4, or 97/3, or 98/2, or 99/1, or >99/<1; comprising: subjecting a substrate represented by Formula (II)

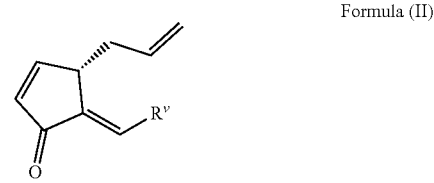

Formula (II)

together with cis-octen-1-ol in the presence of a stereoretentive ruthenium olefin metathesis catalyst represented by Formula (I) as defined herein or in the presence of a Z-selective ruthenium olefin metathesis catalyst represented by Formula (V) as defined herein; and wherein:

$R^v$ is selected from

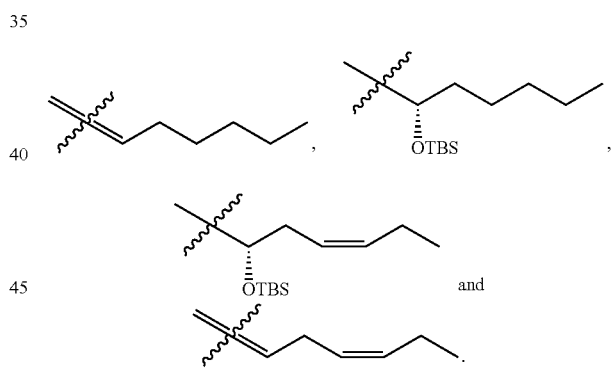

In one embodiment, the invention provides a method for producing at least one alcohol product represented by Formula (III)

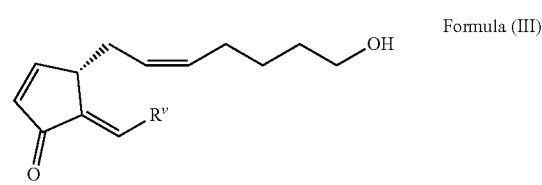

Formula (III)

wherein at least one carbon-carbon double bond has a Z/E-selectivity of 95/5, or 96/4, or 97/3, or 98/2, or 99/1, or >99/<; comprising subjecting a substrate represented by Formula (II)

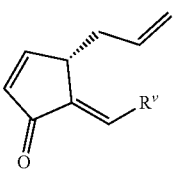
Formula (II)

wherein: R$^v$ is

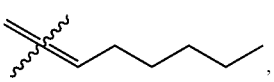 [SMILES: *=CCCCCC], with cis-5-octen-1-ol to a cross-metathesis reaction in the presence of a stereoretentive ruthenium olefin metathesis catalyst represented by Formula (I) as defined herein.

In one embodiment, the invention provides a method for producing at least one alcohol product represented by Formula (III)

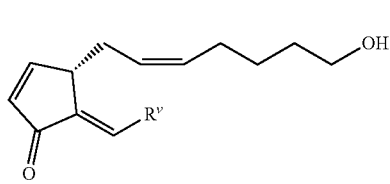
Formula (III)

wherein at least one carbon-carbon double bond has Z/E-selectivity of 95/5, or 96/4, or 97/3, or 98/2, or 99/1, or >99/<1; comprising, subjecting a substrate represented by Formula (II)

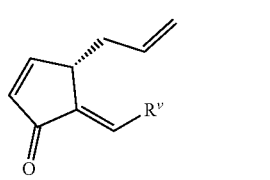
Formula (II)

wherein: R$^v$ is

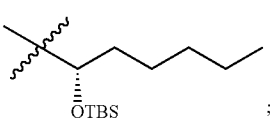 [SMILES: *[C@H](CCCCC)O[Si](C)(C)C(C)(C)C];

with cis-5-octen-1-ol to a cross-metathesis reaction in the presence of a stereoretentive ruthenium olefin metathesis catalyst represented by Formula (I) as defined herein.

In one embodiment, the invention provides a method for producing at least one $\Delta^{12}$-Prostaglandin J product represented by Formula (III)

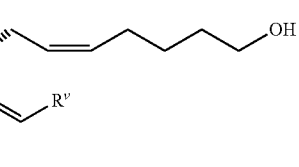
Formula (III)

wherein at least one carbon-carbon double bond has Z/E-selectivity of 95/5, or 96/4, or 97/3, or 98/2, or 99/1, or >99/<1; comprising, subjecting a substrate represented by Formula (II)

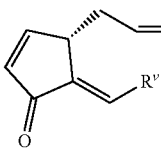
Formula (II)

wherein: R$^v$ is

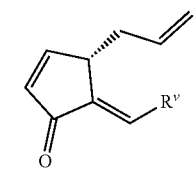, with cis-5-octen-1-ol to a cross-metathesis reaction in the presence of a stereoretentive ruthenium olefin metathesis catalyst represented by Formula (I) as defined herein.

In one embodiment, the invention provides a method for producing at least one alcohol product represented by Formula (III)

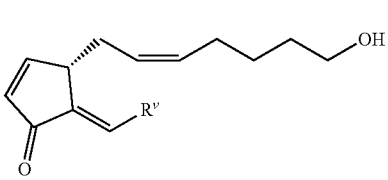
Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

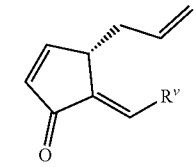
Formula (II)

wherein: R^v is

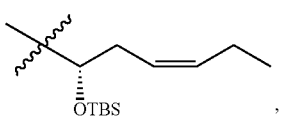

with cis-5-octen-1-ol to a cross-metathesis reaction in the presence of a stereoretentive ruthenium olefin metathesis catalyst represented by Formula (I) as defined herein.

In one embodiment, the invention provides a method for producing at least one alcohol product represented by Formula (III)

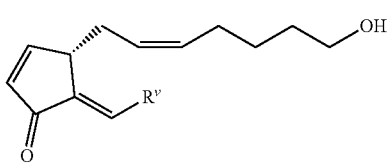

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

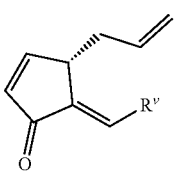

Formula (II)

wherein: R^v is

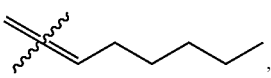 [SMILES: *=CCCCCC]

with cis-5-octen-1-ol to a cross-metathesis reaction in the presence of a Z-selective ruthenium olefin metathesis catalyst represented by Formula (V) as defined herein.

In one embodiment, the invention provides a method for producing at least one alcohol product represented by Formula (II)

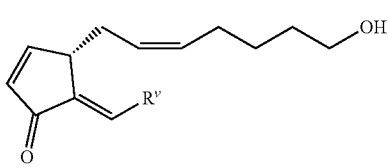

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

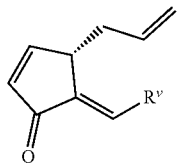

Formula (II)

wherein: R^v is

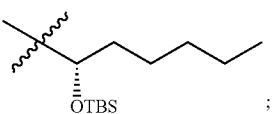 [SMILES: *[C@H](CCCCC)O[Si](C)(C)C(C)(C)C]

with cis-5-octen-1-ol to a cross-metathesis reaction in the presence of a Z-selective ruthenium olefin metathesis catalyst represented by Formula (V) as defined herein.

In one embodiment, the invention provides a method for producing at least one alcohol product represented by Formula (III)

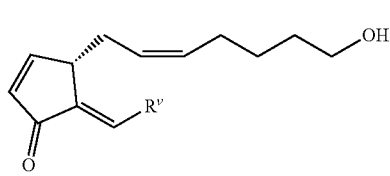

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

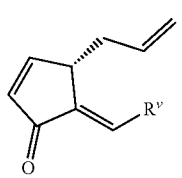

Formula (II)

wherein: R^v is

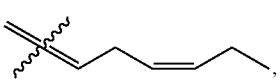 [SMILES: *=CC/C=C\CC]

with cis-5-octen-1-ol to a cross-metathesis reaction in the presence of a Z-selective ruthenium olefin metathesis catalyst represented by Formula (V) as defined herein.

In one embodiment, the invention provides a method for producing at least one alcohol product represented by Formula (III)

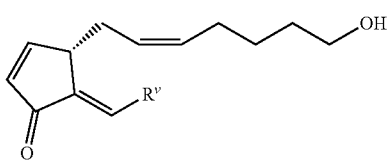
Formula (III)

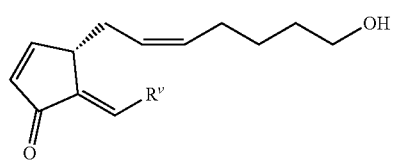
Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

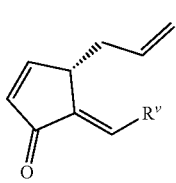
Formula (II)

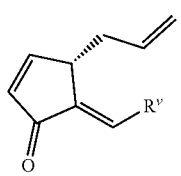
Formula (II)

wherein: R$^v$ is

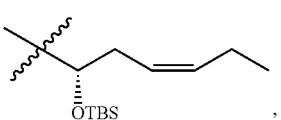 [SMILES: *[C@H](C/C=C\CC)O[Si](C)(C)C(C)(C)C]
, with cis-5-octen-1-ol to a cross-metathesis reaction in the presence of a Z-selective ruthenium olefin metathesis catalyst represented by Formula (V) as defined herein.

In one embodiment, the invention provides a method for producing at least one Δ$^{12}$-Prostaglandin J product represented by Formula (IV), and cis-octen-1-ol in the presence of a stereoretentive ruthenium olefin metathesis catalyst represented by Formula (I) as defined herein; and wherein R$^v$ is

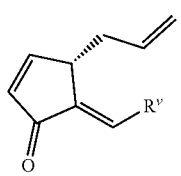
.

In one embodiment, the invention provides a method for producing at least one Δ$^{12}$-Prostaglandin J product represented by Formula (IV),

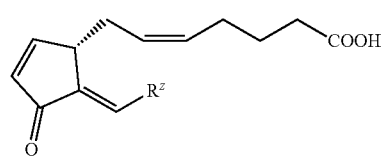
Formula (IV)

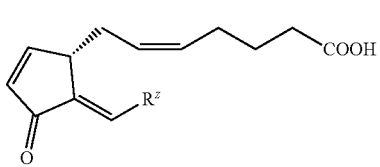
Formula (IV)

wherein: R$^z$ is wherein: R$^z$ is

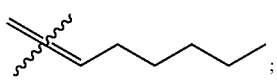 [SMILES: *=CCCCCC]
;

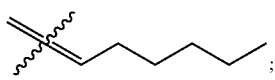 [SMILES: *=CCCCCC]
;

and wherein at least one carbon-carbon double bond has a Z/E-selectivity of 9515, or 96/4, or 97/3, or 98/2, or 99/1, or >99/<1; comprising submitting an alcohol product of Formula (III)

and wherein at least one carbon-carbon double bond has a Z/E-selectivity of 95/5, or 96/4, or 97/3, or 98/2, or 99/1, or >99/<1; comprising submitting an alcohol product of Formula (III)

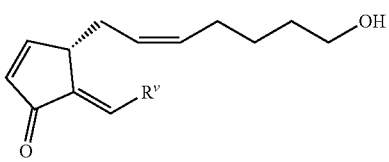

Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

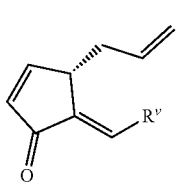

Formula (II)

and cis-octen-1-ol in the presence of a Z-selective ruthenium olefin metathesis catalyst represented by Formula (V) as defined herein; and wherein $R^v$ is

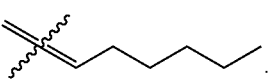 [SMILES: *=CCCCCC]

In one embodiment, the invention provides a method for producing at least one $\Delta^{12}$-Prostaglandin J product represented by Formula (IV),

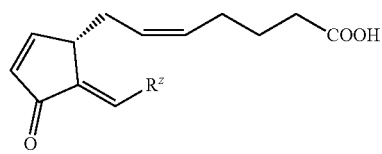

Formula (IV)

wherein: $R^z$ is

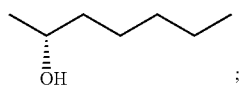

and wherein at east one carbon-carbon double bond has a Z/E-selectivity of 95/5, or 96/4, or 97/3, or 98/2, or 99/1, or >99/<1; by submitting an alcohol product of Formula (III)

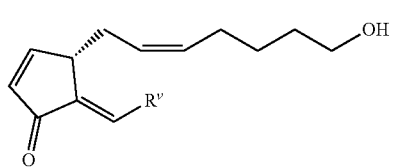

Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

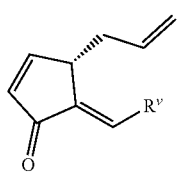

Formula (II)

and cis-octen-1-ol in the presence of a stereoretentive ruthenium olefin metathesis catalyst represented by Formula (I) as defined herein; and wherein $R^v$ is

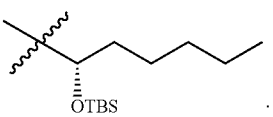 [SMILES: *[C@H](CCCCC)O[Si](C)(C)C(C)(C)C]

In one embodiment, the invention provides a method for producing at least one $\Delta^{12}$-Prostaglandin J product represented by Formula (IV),

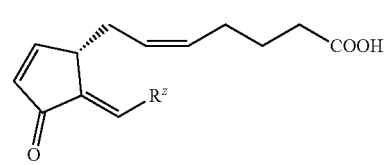

Formula (IV)

wherein: $R^v$ is

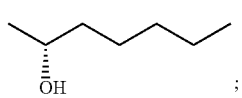

and wherein at least one carbon-carbon double bond has a Z/E-selectivity of 95/5, or 96/4, or 97/3, or 98/2, or 99/1, or >99/<1; comprising submitting an alcohol product of Formula (III)

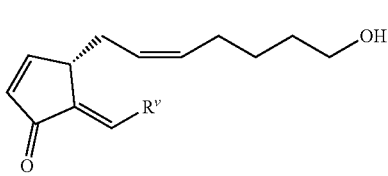
Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

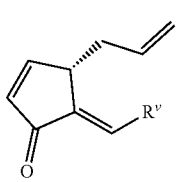
Formula (II)

and cis-octen-1-ol in the presence of a Z-selective ruthenium olefin metathesis catalyst represented by Formula (V) as defined herein; and wherein $R^v$ is selected from

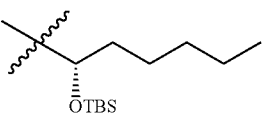

In one embodiment, the invention provides a method for producing at least one $\Delta^{12}$-Prostaglandin J product represented by Formula (IV),

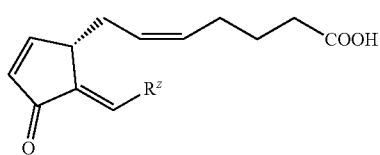
Formula (IV)

wherein: $R^z$ is

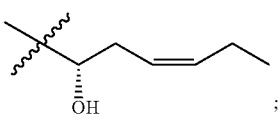 [SMILES: *[C@@H](O)C/C=C\CC]

and wherein at least one carbon-carbon double bond has a Z/E-selectivity of 95/5, or 96/4, or 97/3, or 98/2, or 99/1, or >99/<1; comprising, submitting an alcohol product of Formula (II)

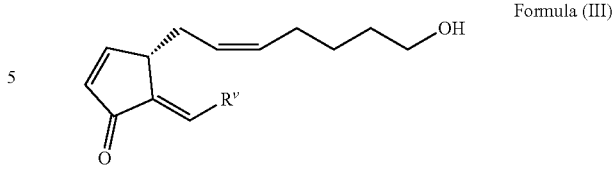
Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

Formula (II)

and cis-octen-1-ol in the presence of a stereoretentive ruthenium olefin metathesis catalyst represented by Formula (I) as defined herein; and wherein $R^v$ is

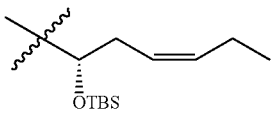

In one embodiment, the invention provides a method for producing at least one $\Delta^{12}$-Prostaglandin J product represented by Formula (IV),

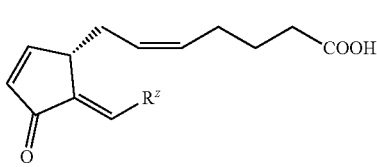
Formula (IV)

wherein: $R^z$ is

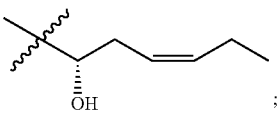 [SMILES: *[C@@H](O)C/C=C\CC]

and wherein at least one carbon-carbon double bond has a Z/E-selectivity of 95/5, or 96/4, or 97/3, or 98/2, or 99/1, or >99/<1; by submitting an alcohol product of Formula (III)

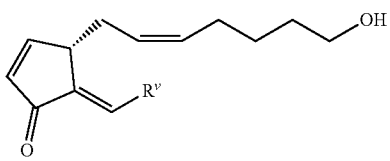
Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

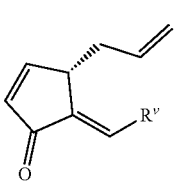
Formula (II)

and cis-octen-1-ol in the presence of a Z-selective ruthenium olefin metathesis catalyst represented by Formula (V) as defined herein; and wherein $R^v$ is selected from

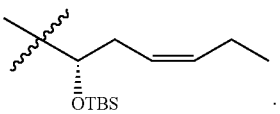 [SMILES: *[C@H](C/C=C\CC)O[Si](C)(C)C(C)(C)C]

In one embodiment, the invention provides a method for producing at least one $\Delta^{12}$-Prostaglandin J product represented b Formula (IV),

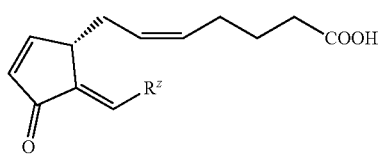
Formula (IV)

wherein: $R^z$ is

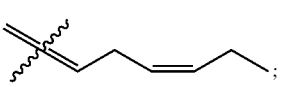 [SMILES: *=CC/C=C\CC]

and wherein at least one carbon-carbon double bond has a Z/E-selectivity of 95/5, or 96/4, or 97/3, or 9/2, or 99/1, or >99/<1; comprising, submitting an alcohol product of Formula (III)

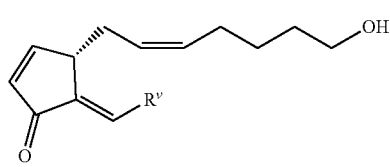
Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

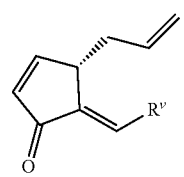
Formula (II)

and cis-octen-1-ol in the presence of a stereoretentive ruthenium olefin metathesis catalyst represented by Formula (I) as defined herein; and wherein $R^v$ is

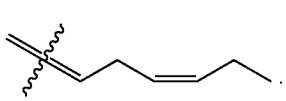

In one embodiment, the invention provides a method for producing at least one $\Delta^{12}$-Prostaglandin J product represented by Formula (IV), Formula (IV)

wherein: $R^z$ is

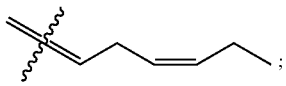 [SMILES: *=CC/C=C\CC]

and wherein at least one carbon-carbon double bond has a Z/E-selectivity of 95/5, or 96/4, or 97/3, or 9/2, or 99/1, or >99/<1; comprising, submitting an alcohol product of Formula (III)

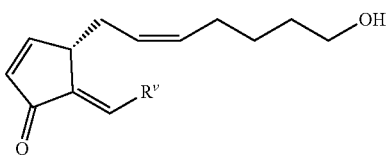

Formula (III)

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

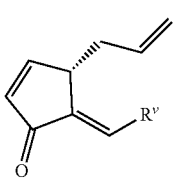

Formula (II)

and cis-octen-1-ol in the presence of a Z-selective ruthenium olefin metathesis catalyst represented Formula (V) as defined herein; and wherein $R^v$ is

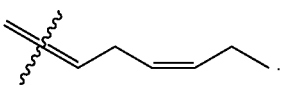 [SMILES: *=CC/C=C\CC]

In one embodiment, the invention provides a method for producing at least one alcohol product represented by Formula (III)

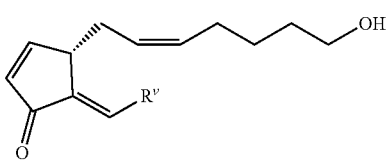

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

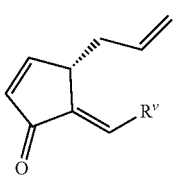

Formula (II)

wherein: $R^v$ is selected from

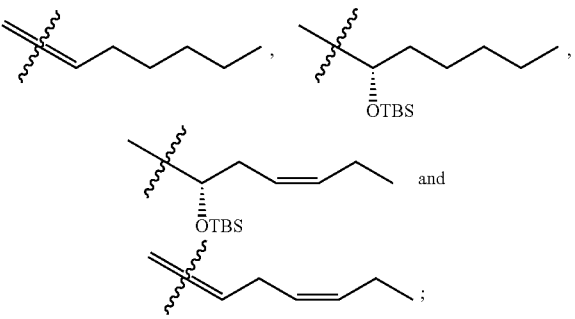

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

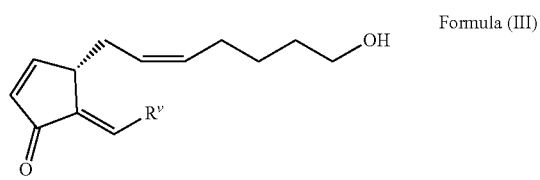

Formula (III)

wherein at least one carbon-carbon double bond has a WE-selectivity of 95/5, or 96/4, or 97/3, or 98/2, or 99/1, or >99/<1; comprising, subjecting a substrate represented by Formula (U)

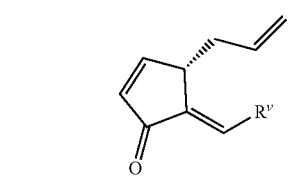

Formula (II)

wherein: $R^v$ is selected from

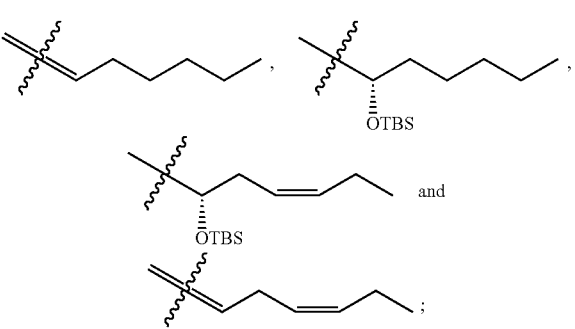

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H. $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr, $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

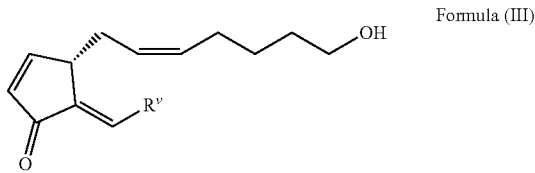

Formula (III)

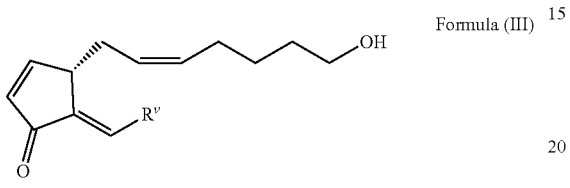

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

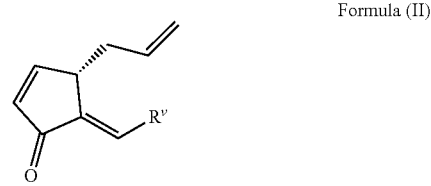

Formula (II)

wherein: $R^v$ is selected from

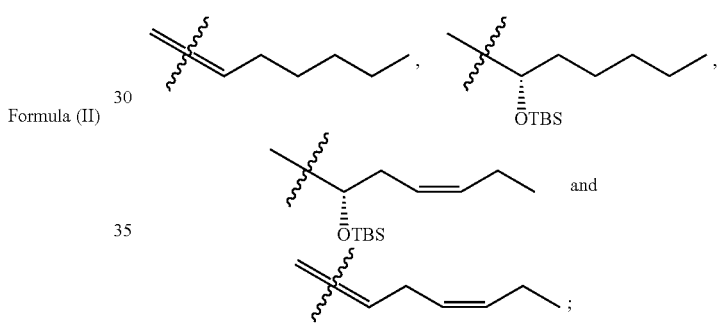

with cis-5-octen-1-ol to a cross-metathesis reaction in the presence of a Z-selective ruthenium olefin metathesis catalyst represented by Formula (V), wherein W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one $\Delta^{12}$-Prostaglandin J product represented by Formula (IV),

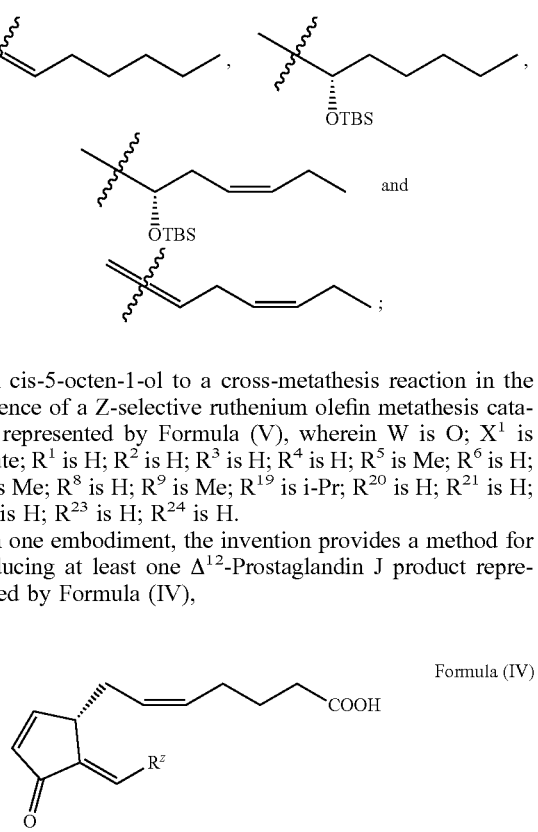

Formula (II)

wherein $R^v$ is selected from

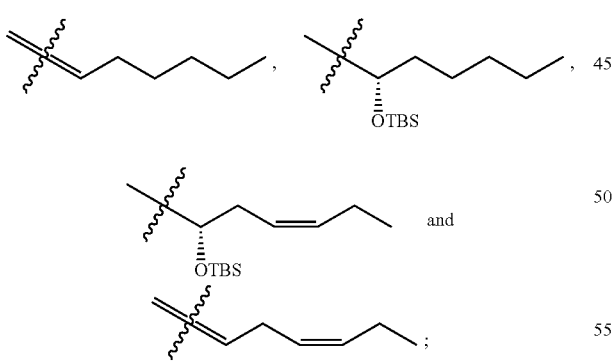

with cis-5-octen-1-ol to a cross-metathesis reaction in the presence of a Z-selective ruthenium olefin metathesis catalyst represented by Formula (V), wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (I)

Formula (IV)

wherein: $R^z$ is selected from

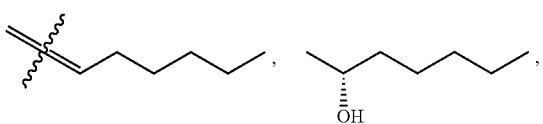

-continued

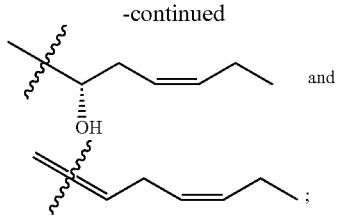 and

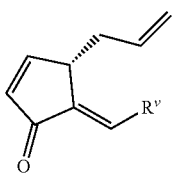;

wherein at least one carbon-carbon double bond has a Z/E-selectivity of 95/5, or 96/4, or 97/3, or 98/2, or 99/1, or >99/<1; by submitting an alcohol product of Formula (III), Formula (III)

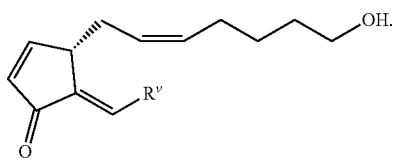

wherein R$^v$ is selected from

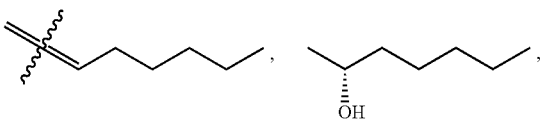

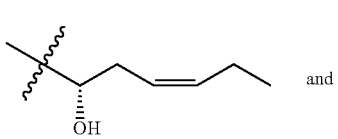;

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

Formula (II)

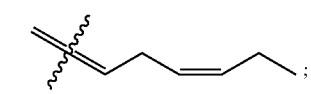

and cis-octen-1-ol in the presence of a stereoretentive ruthenium olefin metathesis catalyst represented by Formula (I); wherein X is S; Y is S; Z is N; W is O; R$^1$ is H; R$^2$ is H; R$^3$ is H; R$^4$ is H; R$^5$ is i-Pr; R$^6$ is H; R$^7$ is H; R$^8$ is H; R$^9$ is i-Pr; R$^{10}$ is i-Pr; R$^{11}$ is H; R$^{12}$ is H; R$^{13}$ is H; R$^{14}$ is i-Pr; R$^{15}$ is Cl; R$^{16}$ is H; R$^{17}$ is H; R$^{18}$ is Cl; R$^{19}$ is i-Pr; R$^{20}$ is H; R$^{21}$ is H; R$^{22}$ is H; R$^{23}$ is H; and R$^{24}$ is H.

In one embodiment, the invention provides a method for producing at least one Δ$^{12}$-Prostaglandin J product represented by Formula (IV), Formula (IV)

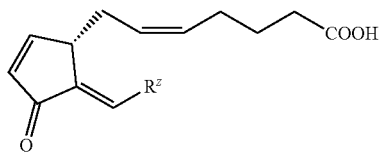

wherein: R$^z$ is selected from

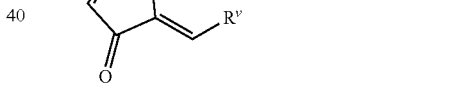

and wherein at least one carbon-carbon double bond has a Z/E-selectivity of 95/5, or 96/4, or 97/3, or 98/2, or 99/1, or >99/<1; by submitting an alcohol product of Formula (III), Formula (III)

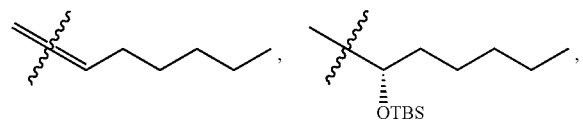

wherein R$^v$ is selected from

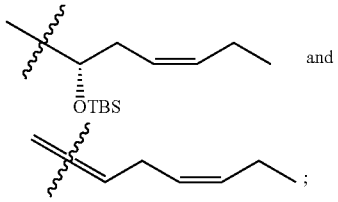

to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

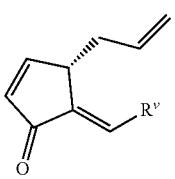

Formula (II)

and cis-octen-1-ol in the presence of a stereoretentive ruthenium olefin metathesis catalyst represented by Formula (I); wherein X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

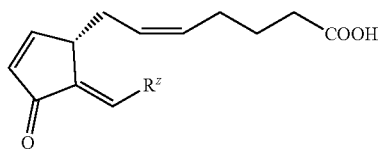

Formula (IV)

wherein: $R^z$ is selected from

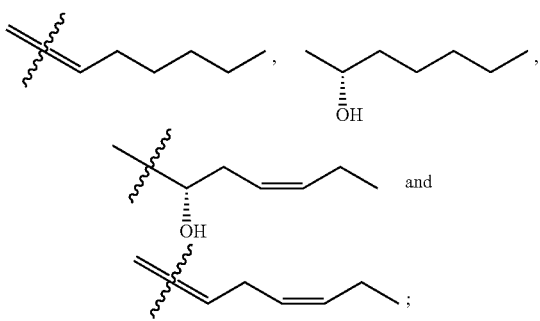

and wherein at least one carbon-carbon double bond has a Z/E-selectivity of 95/5, or 96/4, or 97/3, or 982, or 99/1, or >99/<1; by submitting an alcohol product of Formula (III),

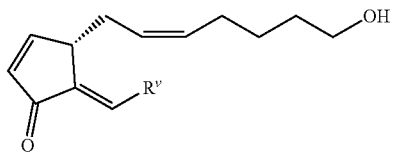

Formula (III)

wherein $R^v$ is selected from

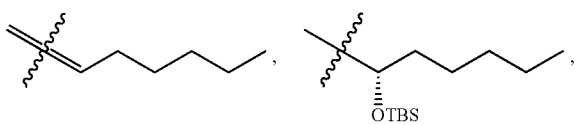

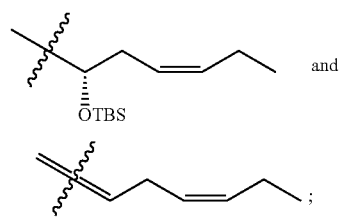

and to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

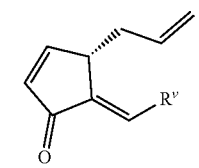

Formula (II)

and cis-octen-1-ol in the presence of a Z-selective ruthenium olefin metathesis catalyst represented by Formula (V); wherein W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one $\Delta^{12}$-Prostaglandin J product represented by Formula (IV),

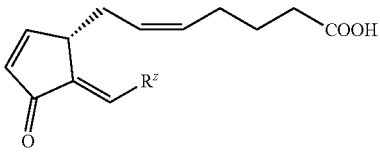

Formula (IV)

wherein: $R^z$ is selected from

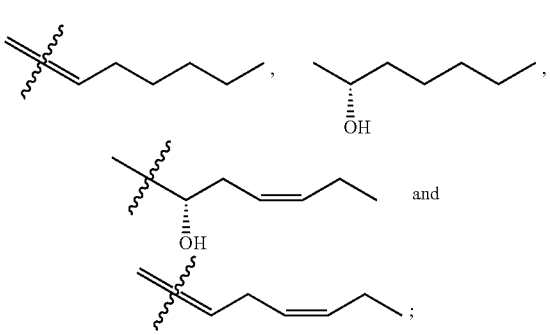

and wherein at least one carbon-carbon double bond has a Z/E-selectivity of 95/5, or 96/4, or 97/3, or 98/2, or 99/1, or >99/<1; by submitting an alcohol product of Formula (III),

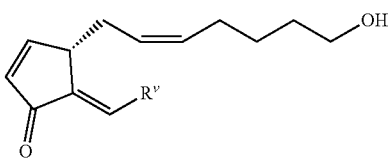

Formula (III)

wherein $R^v$ is selected from

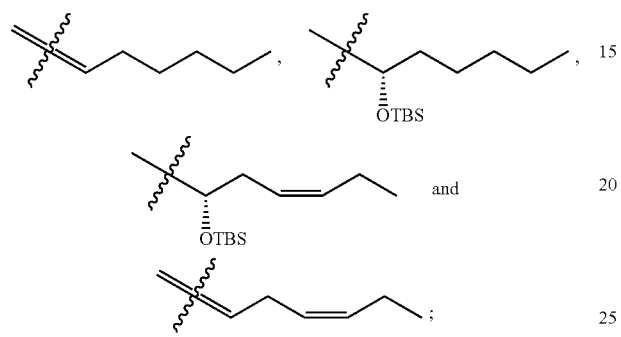

and to oxidation in the presence of tetrapropylammonium perruthenate and 4-methylmorpholine N-oxide monohydrate or to oxidation in the presence of pyridinium chlorochromate and sodium chlorite; wherein the alcohol product of Formula (III) is formed during the cross-metathesis reaction between a substrate represented by Formula (II)

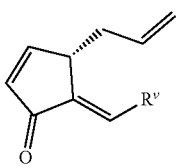

Formula (II)

and cis-octen-1-ol in the presence of a Z-selective ruthenium olefin metathesis catalyst represented by Formula (V); wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

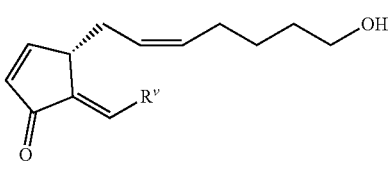

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

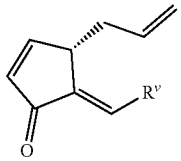

Formula (II)

wherein: $R^v$ is

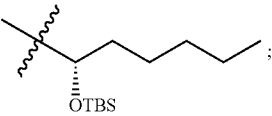 [SMILES: *[C@H](CCCCC)O[Si](C)(C)C(C)(C)C]

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

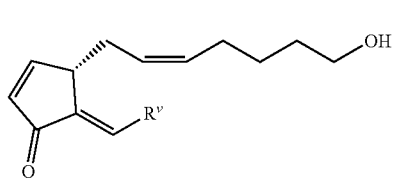

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

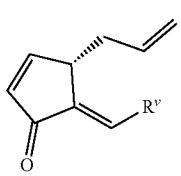

Formula (II)

wherein: $R^v$ is

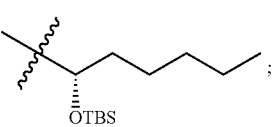 [SMILES: *[C@H](CCCCC)O[Si](C)(C)C(C)(C)C]

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is i-Pr;

$R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

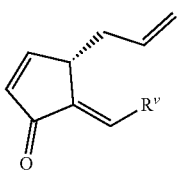

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

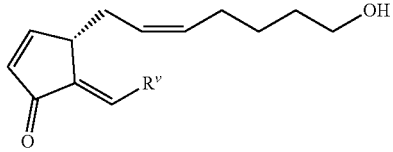

Formula (II)

wherein: $R^v$ is

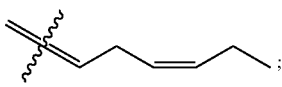

;

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is i; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

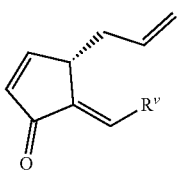

Formula (III)

wherein at least one carbon-carbon double bond has Z/E-selectivity of 95/5, or 96/4, or 97/3, or 98/2, or 99/1, or >99/<1; comprising: subjecting a substrate represented by Formula (II)

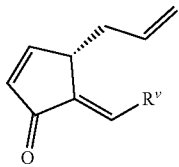

Formula (II)

wherein: $R^v$ is

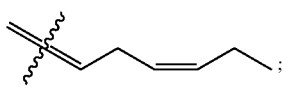 [SMILES: *=CC/C=C\CC]

;

with cis-5-octen-1-ol to a cross-metathesis reaction in the presence of a stereoretentive ruthenium olefin metathesis catalyst represented by Formula (I), wherein: X is S; Y is S; Z is N; W is O; $R^1$ is H; $R^2$ is H; $R^3$ is H; $R^4$ is H; $R^5$ is i-Pr $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

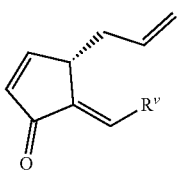

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

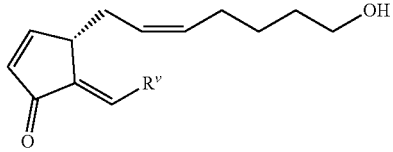

Formula (II)

wherein: $R^v$ is

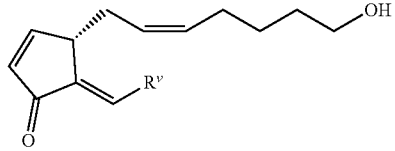

;

with cis-5-octen-1-ol to a cross-metathesis reaction in the presence of a Z-selective ruthenium olefin metathesis catalyst represented by Formula (V), wherein W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

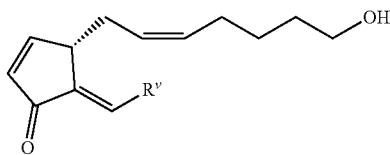
Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

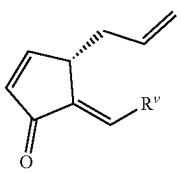
Formula (II)

wherein: $R^v$ is

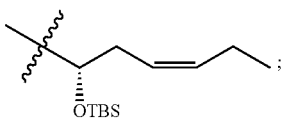 [SMILES: *[C@H](C/C=C\CC)O[Si](C)(C)C(C)(C)C]

with cis-5-octen-1-ol to a cross-metathesis reaction in the presence of a Z-selective ruthenium olefin metathesis catalyst represented by Formula (V), wherein W is O; $X^1$ is nitrate; $R^1$ is F; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

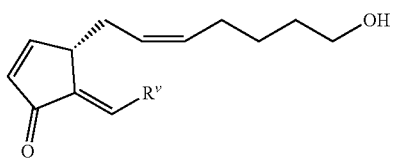
Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (II)

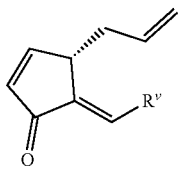
Formula (II)

wherein: $R^v$ is

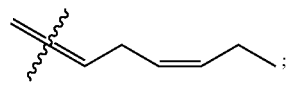 [SMILES: *=CC/C=C\CC]

with cis-5-octen-1-ol to a cross-metathesis reaction in the presence of a Z-selective ruthenium olefin metathesis catalyst represented by Formula (V), wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

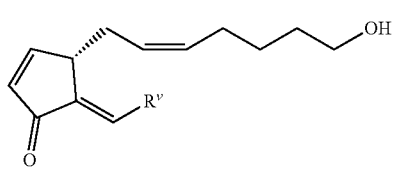
Formula (III)

wherein at least one carbon-carbon double bond has a Z/E-selectivity of 95/5, or 96/4, or 97/3, or 98/2, or 99/1, or >99/<1; comprising: subjecting a substrate represented by Formula (II)

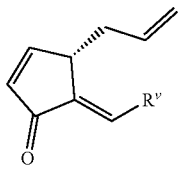
Formula (II)

wherein: $R^v$ is

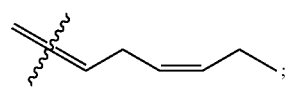 [SMILES: *=CC/C=C\CC]

with cis-5-octen-1-ol to a cross-metathesis reason in the presence of a Z-selective ruthenium olefin metathesis catalyst represented by Formula (V), wherein W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr $R^{20}$ is H; $R^{21}$ is H; $R^{22}$ is H; $R^{23}$ is H; $R^{24}$ is H.

In one embodiment, the invention provides a method for producing at least one alcohol product represented by Formula (III)

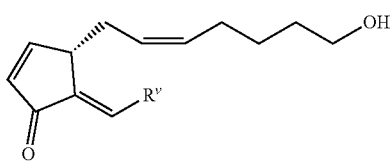

Formula (III)

wherein at least one carbon-carbon double bond has a Z/E-selectivity of 95/5, or 96/4, or 97/3, or 98/2, or 99/1, or >99/<1; comprising, subjecting a substrate represented by Formula (I)

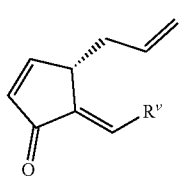

Formula (II)

wherein: $R^v$ is

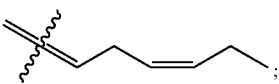

with cis-5-octen-1-ol to a cross-metathesis reaction in the presence of a stereoretentive ruthenium olefin metathesis catalyst represented Formula (I), wherein: X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one alcohol product represented by Formula (III)

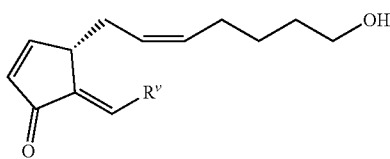

Formula (III)

wherein at least one carbon-carbon double bond has a Z/E-selectivity of 95/5, or 96/4, or 97/3, or 98/2, or 99/1, or >99/<1; comprising: subjecting a substrate represented by Formula (II)

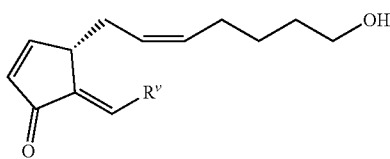

Formula (II)

wherein: $R^v$ is

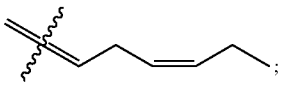

with cis-5-octen-1-ol to a cross-metathesis reaction in the presence of a stereoretentive ruthenium olefin metathesis catalyst represented by Formula (I), wherein X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr, $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is J.

In one embodiment, the invention provides a method for producing at least one $\Delta^{12}$-Prostaglandin J product represented by Formula (IV),

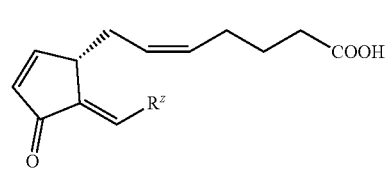

Formula (IV)

wherein: $R^z$ is

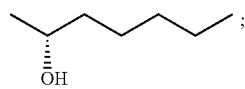

and wherein at least one carbon-carbon double bond has a Z/E-selectivity of 95/5, or 96/4, or 97/3, or 98/2, or 99/1, or >99/<1; comprising submitting an alcohol product of Formula II,

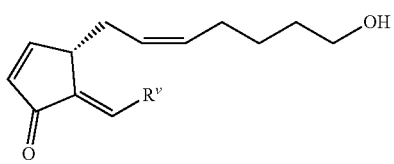

Formula (III)

wherein $R^v$ is

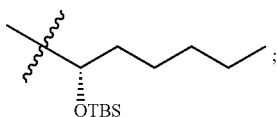 [SMILES: *[C@H](CCCCC)O[Si](C)(C)C(C)(C)C]

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

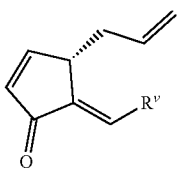

Formula (II)

and cis-octen-1-ol in the presence of a stereoretentive ruthenium olefin metathesis catalyst represented by Formula (I); wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

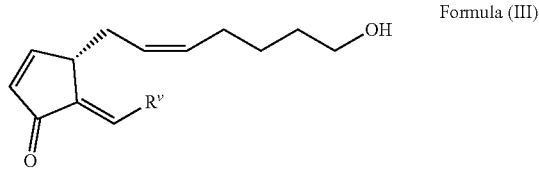

Formula (III)

wherein: $R^z$ is

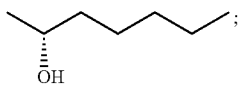

and wherein at least one carbon-carbon double bond has a Z/E-selectivity of 95/5, or 96/4, or 97/3, or 98/2, or 99/1, or >99/<1; comprising, submitting an alcohol product of Formula (III), wherein

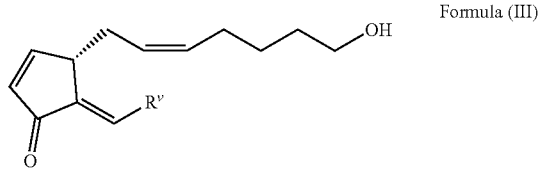

Formula (III)

$R^v$ is

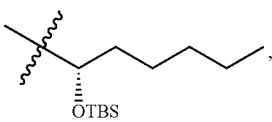 [SMILES: *[C@H](CCCCC)O[Si](C)(C)C(C)(C)C]

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

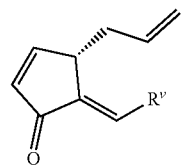

Formula (II)

and cis-octen-1-ol in the presence of a stereoretentive ruthenium olefin metathesis catalyst represented by Formula (I); wherein X is S; Y is S; Z is N; W is O; $R^1$ is H; $R^2$ is H; $R^3$ is if; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

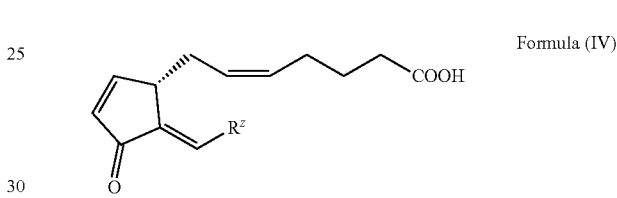

Formula (IV)

wherein: $R^z$ is selected from

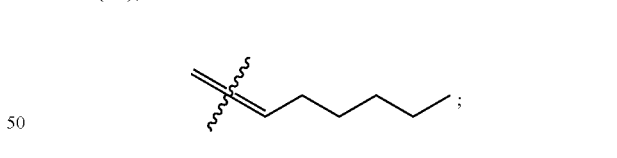

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

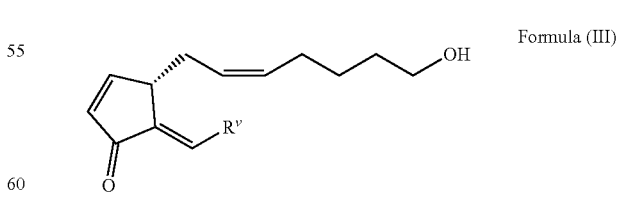

Formula (III)

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

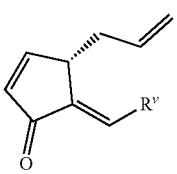

Formula (II)

and cis-octen-1-ol in the presence of a stereoretentive ruthenium olefin metathesis catalyst represented by Formula (I); wherein X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr, $R^{10}$ is i-Pr, $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr, $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

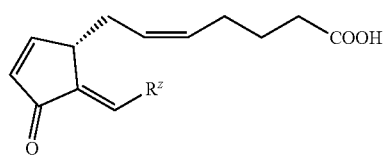

Formula (IV)

wherein: $R^z$ is selected from

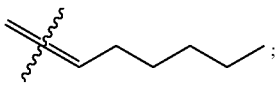 [SMILES: *=CCCCCC]

and wherein at least one carbon-carbon double bond has a Z/E-selectivity 95/5, or 96/4, or 97/3, or 98/2, or 99/1, or >99/<1; by submitting an alcohol product of Formula (III), wherein $R^v$ is

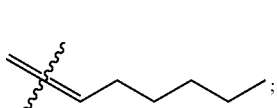

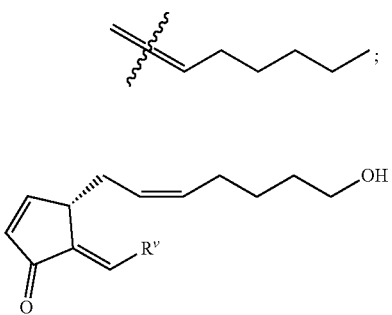

Formula (III)

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

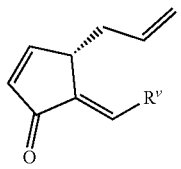

Formula (II)

and cis-octen-1-ol in the presence of a stereoretentive ruthenium olefin metathesis catalyst represented by Formula (I); wherein X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

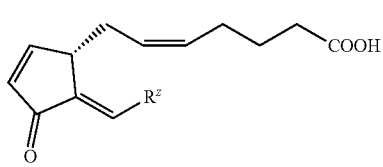

Formula (IV)

wherein: $R^z$ is

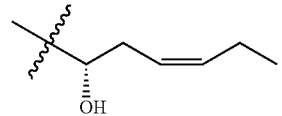

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

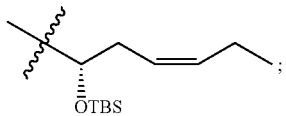

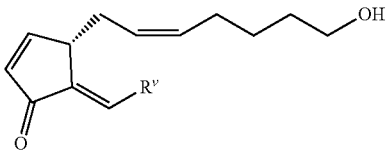

Formula (III)

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

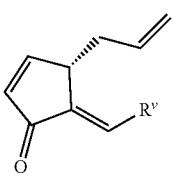
Formula (II)

and cis-octen-1-ol in the presence of a Z-selective ruthenium olefin metathesis catalyst represented by Formula (V); wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one $\Delta^{12}$-Prostaglandin J product represented by Formula (IV),

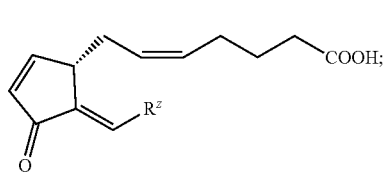
Formula (IV)

wherein: $R^z$ is

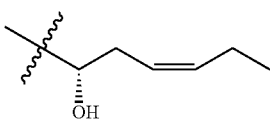 [SMILES: *[C@@H](O)C/C=C\CC]

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

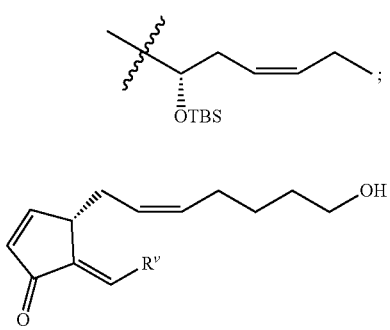
Formula (III)

to oxidation in the presence of tetrapropylammonium perruthenate and 4-methylmorpholine N-oxide monohydrate; wherein the alcohol product of Formula (III) is formed during the cross-metathesis reaction between a substrate represented by Formula (II)

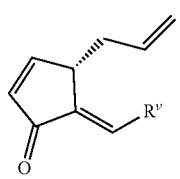
Formula (II)

and cis-octen-1-ol in the presence of a Z-selective ruthenium olefin metathesis catalyst represented by Formula (V); wherein: W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{22}$ is H; $R^{24}$ is H.

In one embodiment, the invention provides a method for producing at least one $\Delta^{12}$-Prostaglandin J product represented by Formula (IV),

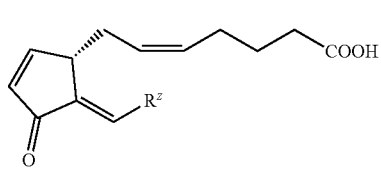
Formula (IV)

wherein: $R^z$ is selected from

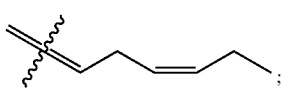 [SMILES: *=CC/C=C\CC]

and wherein at least one carbon-carbon double bond has a Z/E-selectivity of 95/5, or 96/4, or 97/3, or 98/2, or 99/1, or >99/<1; comprising, submitting an alcohol product of Formula III wherein $R^v$ is

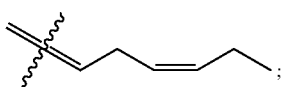 [SMILES: *=CC/C=C\CC]

Formula (III)

to oxidation in the presence of pyridinium chlorochromate and sodium chlorite; wherein the alcohol product of Formula (III) is formed during the cross-metathesis reaction between a substrate represented by Formula (II)

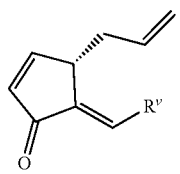
Formula (II)

and cis-octen-1-ol in the presence of a Z-selective ruthenium olefin metathesis catalyst represented by Formula (V); wherein W is O; X is nitrate; $R^1$ is H; $R^2$ is H; $R^3$ is H; $R^4$ is H; $R^5$ is i-Pr, $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one $\Delta^{12}$-Prostaglandin J product represented by Formula (IV).

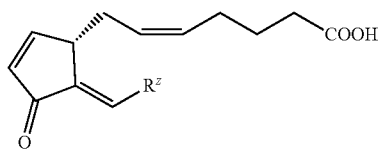

Formula (IV)

wherein: $R^z$ is

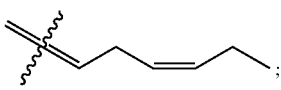

;

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

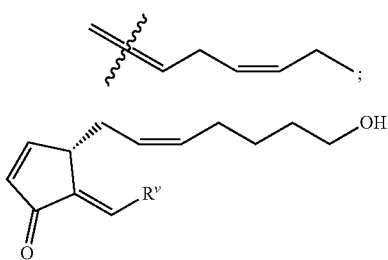

Formula (III)

to oxidation in the presence of pyridinium chlorochromate and sodium chlorite; wherein the alcohol product of Formula (I) is formed during the cross-metathesis reaction between a substrate represented by Formula (I)

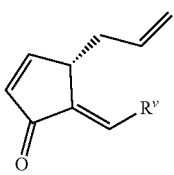

Formula (II)

and cis-octen-1-ol in the presence of a Z-selective ruthenium olefin metathesis catalyst represented by Formula (V); wherein W is O; $X^1$ is nitrate; $R^1$ is H; $R^2$ is H; $R^3$ is H; $R^4$ is H; $R^5$ is Me; $R^6$ is H; $R^7$ is Me; $R^8$ is H; $R^9$ is Me; $R^{19}$ is i-Pr; $R^{20}$ is H; $R^{21}$ is H; $R^{22}$ is H; $R^{23}$ is H; $R^{24}$ is H.

In one embodiment, the invention provides a method for producing at least one $\Delta^{12}$-Prostaglandin J product represented by Formula (IV),

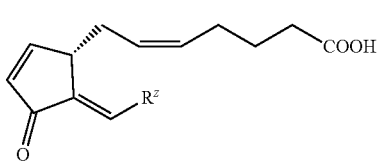

Formula (IV)

wherein: $R^z$ is

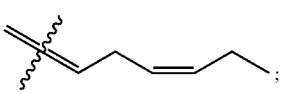 [SMILES: *=CC/C=C\CC]

;

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

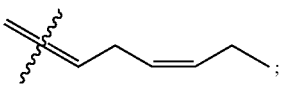

;

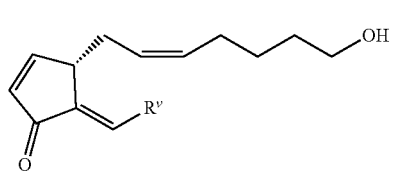

Formula (III)

to oxidation in the presence of pyridinium chlorochromate and sodium chlorite; wherein the alcohol product of Formula (III) is formed during the cross-metathesis reaction between a substrate represented by Formula (III)

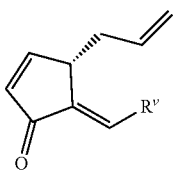

Formula (II)

and cis-octen-1-ol in the presence of a stereoretentive ruthenium olefin metathesis catalyst represented by Formula (I); wherein X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

In one embodiment, the invention provides a method for producing at least one $\Delta^{12}$-Prostaglandin J product represented by Formula (IV),

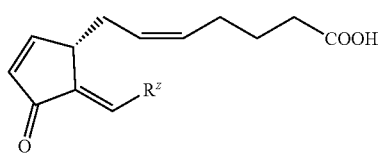

Formula (IV)

wherein: $R^z$ is

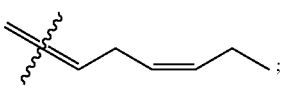 [SMILES: *=CC/C=C\CC]

and wherein at least one carbon-carbon double bond has a Z/E-selectivity of 95/5, or 96/4, or 97/3, or 98/2, or 99/1, or >99/<1; comprising, submitting an alcohol product of Formula (III), wherein $R^v$ is

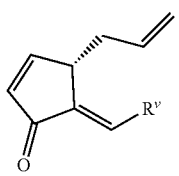

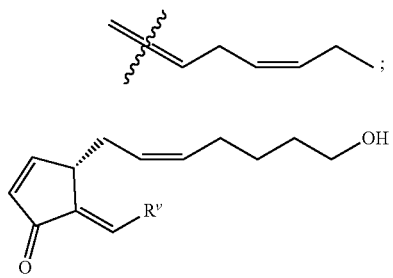

Formula (III)

to oxidation in the presence of pyridinium chlorochromate and sodium chlorite; wherein the alcohol product of Formula (III) is formed during the cross-metathesis reaction between a substrate represented by Formula (II)

Formula (II)

and cis-octen-1-ol in the presence of a stereoselective ruthenium olefin metathesis catalyst represented by Formula (I); wherein X is S; Y is S; Z is N; W is O; $R^1$ is H; $R^2$ is H; $R^3$ is H; $R^4$ is H; $R^5$ is Me; $R^6$ is H; $R^7$ is Me; $R^8$ is H; $R^9$ is Me; $R^{10}$ is Me; $R^{11}$ is H; $R^{12}$ is Me; $R^{13}$ is H; $R^{14}$ is Me; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees Celsius and pressure is at or near atmospheric. The examples are to be considered as not being limiting of the invention as described herein and are instead provided as representative examples of the catalyst compounds of the invention, of the methods that may be used in their preparation, and of the methods of using the inventive catalysts.

Materials and Methods

Unless noted in the specific procedure, reactions were performed in flame-dried glassware under argon atmosphere. All metathesis reactions were carried out under air-free conditions in dry glassware in a Vacuum Atmospheres Glovebox filled with $N_2$. General solvents were purified by passing through solvent purification columns. Commercially available substrates were used as received. All solvents and substrates were sparged with Ar before bringing into the glovebox and filtered over basic alumina (Brockmann I) prior to use. Reaction progress was monitored by thin-layer chromatography (TLC) using E. Merck silica gel 60 F254 precoated plates (0.25 mm) and visualized by UV fluorescence quenching, potassium permanganate, or p-anisaldehyde staining. Silicycle SiliaFlash P60 Academic Silica gel (particle size 0.040-0.063 mm) was used for flash chromatography. Analytical chiral HPLC was performed with an Agilent 1100 Series HPLC utilizing a Chiralcel OD-H column (4.6 mm×25 cm) obtained from Daicel Chemical Industries, Ltd. with visualization at 254 nm. Analytical SFC was performed with a Mettler SFC supercritical $CO_2$ analytical chromatography system utilizing Chiralcel (IC) column (4.6 mm×25 cm) obtained from Daicel Chemical Industries, Ltd. with visualization at 210 nm. GC conversion data was obtained using an HP-5 capillary column with an Agilent 6850 FID gas chromatograph. $^1H$ and $^{13}C$ NMR spectra were recorded on a Varian Inova 500 spectrometer (500 MHz and 126 MHz, respectively), a Bruker AV III HD spectrometer equipped with a Prodigy liquid nitrogen temperature cryoprobe (400 MHz and 101 MHz, respectively), or a Varian Mercury 300 spectrometer (300 MHz and 75 MHz, respectively) and are reported in terms of chemical shift relative to residual $CHCl_3$ (δ 7.26 and δ 77.16 ppm, respectively). Data for $^1H$ NMR spectra are reported as follows: chemical shift (δ ppm) (multiplicity, coupling constant (Hz), integration). Abbreviations are used as follows: s=singlet, bs=broad singlet, d=doublet, t=triplet, q=quartet, quint=quintet, m=complex multiplet. Infrared (IR) spectra were recorded on a Perkin Elmer Paragon 1000 spectrometer using neat samples on ATR diamond, and are reported in frequency of absorption ($cm^{-1}$). High-resolution mass spectra HRMS were acquired from the Caltech Mass Spectral Facility using fast-atom bombardment ($FAB^+$), electrospray ionization ($IOF\ ES^+$) or electron impact ($EI^+$). Optical rotations were measured on a Jasco P-2000 polarimeter using a 100 mm path-length cell at 589 nm.

The following abbreviations are used herein:
RT or r.t. room temperature
$CDCl_3$ deuterated chloroform
$CHCl_3$ chloroform
$C_6H_6$ benzene
THF tetrahydrofuran
$NaH_2PO_4 \cdot H_2O$ sodium dihydrogen phosphate monohydrate
$NaClO_2$ sodium chlorite
$NMO \cdot H_2O$ 4-methylmorpholine N-oxide monohydrate
TPAP tetrapropylammonium perruthenate
MeCN acetonitrile
$Et_2O$ diethyl ether
$NaHCO_3$ sodium bicarbonate
t-BuOH tert-butylalcohol
$DCM/CH_2Cl_2$ dichloromethane
DMAP 4-dimethylaminopyridine
$SiO_2$ silicagel

Example 1

Preparation of Alcohol 14

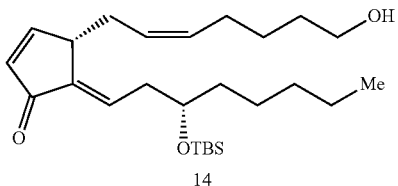 [SMILES: CCCCC[C@@H](C/C=C1/C(=O)C=C[C@@H]1C/C=C\CCCCO)O[Si](C)(C)C(C)(C)C]

14

In a nitrogen-filled glovebox, cis-5-octen-1-ol (150 mg, 1.17 mmol, 8.0 equiv) was dissolved in toluene (2 mL) in a 50 mL. Schlenk flask, and a solution of catalyst Ru-4 (9.9 mg, 11.7 μmol, 1 mol %) in THF (0.7 mL) was added. The Schlenk flask was sealed and brought out of the glovebox, and then connected to high vacuum. The valve was gradually opened (Caution: open slowly and stir well to avoid splashing). After 15 minutes stirring, the flask was refilled with argon and sealed, and was brought back into the glovebox. The residue was diluted with THF (0.5 mL), and an aliquot was taken for GC analysis (conversion of homodimerization step was >98% by GC analysis). A solution of 11 [CAS 2135628-52-1] (53 mg, 0.146 mmol, 1.0 equiv) in THF (0.5 mL) was added into the Schlenk flask and an additional portion of catalyst Ru-4 (6.2 mg, 7.3 μmol, 5 mol %) solution in THF (0.3 mL) was added. The Schlenk flask was sealed and brought out of glovebox. The reaction was stirred for 24 h at 40° C. before a few drops of ethyl vinyl ether were added. The solvent was removed under reduced pressure. The residue was purified by flash chromatography (SiO$_2$, hexanes/EtOAc 2:1) to give 14 (60 mg, 95%, >99:1 Z/E).

TLC (3:1 hexanes/EtOAc): Rf=0.23 (UV).

$^1$H NMR (400 MHz, CDCl$_3$): δ 7.50 (ddd, J=6.0, 2.6, 1.0 Hz, 1H), 6.59 (ddt, J=8.3, 7.0, 1.3 Hz, 1H), 6.33 (dd, J=6.0, 1.8 Hz. 1H), 5.49 (dddt, J=8.6, 7.2, 5.5, 1.5 Hz, 1H), 5.35 (dtt, J=11.0, 8.4, 1.6 Hz, 1H), 3.84 (quint, J=5.9 Hz, 1H), 3.63 (t, J=6.5 Hz, 2H), 3.46 (ddt, J=11.0, 4.2, 2.2 Hz, 1H), 2.63 (dddd, J=13.8, 6.5, 4.2, 1.5 Hz, 1H), 2.50-2.34 (m, 2H), 2.17 (dddd, 7=14.5, 9.4, 8.0, 1.3 Hz, 1H), 2.07-1.97 (m, 2H), 1.60-1.51 (m, 2H), 1.47-1.34 (m, 6H), 1.32-1.19 (m, 5H), 0.95-0.81 (m, 12H), 0.05 (s, 3H), 0.05 (s, 3H).

$^{13}$C NMR (101 MHz, CDCl$_3$): δ 196.5, 161.8, 138.8, 135.0, 132.7, 132.5, 125.4, 71.7, 62.9, 43.6, 37.5, 37.5, 32.5, 32.0, 30.7, 27.0, 26.0, 25.8, 25.1, 22.8, 18.2, 14.2, −4.2, −4.5.

FTIR (ATR): 3443, 2956, 2928, 2856, 1703, 1652, 1580, 1472, 1360, 1251, 1206, 1127, 1048, 1005, 975, 866, 834, 806, 773, 726, 664 cm$^{-1}$.

HRMS (TOF, ES$^+$, m/z): calc'd for C$_{26}$H$_{47}$O$_3$Si [M+H]$^+$ 435.3289, found: 435.3298.

[α]$^D_{23}$: +83.5° (c=1.0, CHCl$_3$).

Example 2

Preparation of Δ$^{12}$-Prostaglandin J$_2$ (1)

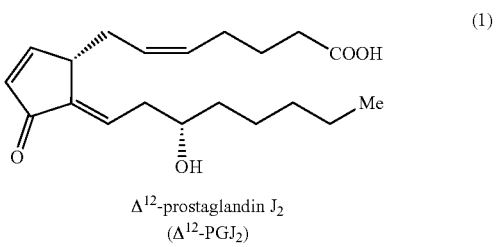 [SMILES: CCCCC[C@H](O)C/C=C1/C(=O)C=C[C@@H]1C/C=C\CCCC(=O)O]

Δ$^{12}$-prostaglandin J$_2$
(Δ$^{12}$-PGJ$_2$)

To a stirred solution of 14 (26 mg, 0.06 mmol, 1.0 equiv) in MeCN (0.3 mL) was added NMO·H$_2$O (81 mg, 6 mmol, 10.0 equiv). Tetrapropylammonium perruthenate (2.1 mg, 6 μmol, 0.1 equiv) was added until NMO·H$_2$O was fully dissolved, and the reaction was stirred at 23° C. for 3 hours. The solution was diluted with Et$_2$O (5 mL), passed through a short pad of silica gel, concentrated and was subjected to the next reaction without further purification. The residue was dissolved in MeCN (1.0 mL) and cooled to 0° C. A solution of hydrofluoric acid (48 wt. % in H$_2$O, 0.2 mL) In MeCN (0.4 mL) was added dropwisely. The solution was stirred in the same temperature for 30 min before saturated NaHCO$_3$ solution (1.5 mL) and brine (1.5 mL) were added. The aqueous phase was extracted with EtOAc (5×5 mL). The combined organic phases were dried over magnesium sulfate, filtered and concentrated (not to dryness). The residue was purified by flash chromatography (SiO$_2$, CH$_2$Cl$_2$/MeOH 20:1) to give 1 (18 mg, 89% over 2 steps) as a colorless liquid.

TLC (20:1 CH$_2$Cl$_2$/MeOH): Rf=0.14 (UV).

$^1$H NMR (500 MHz, CDCl$_2$): δ 7.57 (ddd, J=6.0, 2.6, 1.0 Hz, 1H), 6.58 (ddt, J=8.4, 7.2, 1.3 Hz, 1H), 6.36 (dd, J=6.0, 1.8 Hz, 1H), 5.54-5.38 (m, 2H), 3.86 (dtt, J=7.9, 6.4, 4.0 Hz, 1H), 3.47 (ddt, J=9.5, 4.0, 2.1 Hz, 1H), 2.78-2.68 (m. 1H), 2.57 (dt, J=14.8, 6.8 Hz, 1H), 2.52-2.42 (m, 1H), 2.40-2.33 (m, 2H), 2.20-2.02 (m, 3H), 1.77-1.64 (m, 2H), 1.61-1.41 (m, 3H), 1.40-1.24 (m, 5H), 0.90 (t, J=6.8 Hz, 3H).

$^{13}$C NMR (126 MHz, CDCl$_3$): δ 196.6, 177.3, 162.0, 139.8, 135.0, 131.8, 131.7, 126.2, 71.5, 43.9, 37.3, 36.7, 33.1, 31.9, 30.6, 26.6, 25.4, 24.6, 22.8, 14.2.

FTIR (ATR): 3445, 2960, 2929, 2858, 1699, 1646, 1579, 1463, 1406, 1265, 1237, 1135, 1084, 1033, 842, 810, 734, 702 cm$^{-1}$.

HRMS (TOF, ES$^+$, m/z): calc'd for C$_{20}$H$_{31}$O$_4$[M+H]$^+$ 335.2217, found: 335.2223.

[α]$^D_{23}$: +99.5° (c=0.2, CHCl$_3$).

Spectral data ($^1$H NMR, $^{13}$C NMR, HRMS matched with the published data: Acharya, H. P.; Kobayashi, Y. Highly Efficient Total Synthesis of Δ$^{12}$-PGJ$_2$, 15-Deoxy-Δ$^{12}$, —PGJ$_2$, and Their Analogues, *Tetrahedron* 2006, 62, 3329-3343.

Example 3

Preparation of Alcohol 17

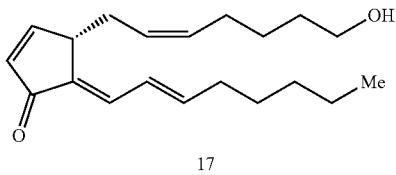 [SMILES: CCCCC/C=C/C=C1/C(=O)C=C[C@@H]1C/C=C\CCCCO]

17

In a nitrogen-filled glovebox, cis-5-octen-1-ol (113 mg, 0.88 mmol, 8.0 equiv) was dissolved in toluene (1 mL) in a 50 mL Schlenk flask and a solution of catalyst Ru-4 (7.5 mg. 8.8 µmol, mol %) in THF (0.6 mL) was added. The Schlenk flask was sealed and brought out of the glovebox, and then connected to high vacuum. The valve was gradually opened (Caution: open slowly and stir well to avoid splashing). After 15 minutes stirring, the flask was refilled with argon and sealed, and was brought back into the glovebox. The residue was diluted with THF (0.5 mL), and an aliquot was taken for GC analysis (conversion of homodimerization step was >98% by GC analysis). A solution of 16 [CAS 2254448-24-1] (25 mg, 0.11 mmol, 1.0 equiv) in THF (0.5 mL) was added into the Schlenk flask and an additional portion of catalyst Ru-4 (4.6 mg, 5.5 µmol, 5 mol %) solution in THF (0.2 mL) was added. The Schlenk flask was sealed and brought out of glovebox. The reaction was stirred for 24 h at 40° C. before a few drops of ethyl vinyl ether were added. The solvent was removed under reduced pressure. The residue was purified by flash chromatography (SiO$_2$, hexanes/EtOAc 2:1) to give 17 (31 mg, 93%, >99:1 Z/E, 87% ee by chiral HPLC analysis).

TLC (4:1 hexanes/EtOAc): Rf=0.2 (JV).

$^1$H NMR (400 MHz, CDCl$_3$) δ 7.48 (ddd, J=6.0, 2.6, 1.0 Hz, 1H), 6.95 (dt, J=11.0, 1.3 Hz, 1H), 6.35 (dd, J=6.0, 1.8 Hz, 1H), 6.34-6.19 (m, 2H), 5.52-5.44 (m, 1H), 5.38-5.30 (m, 1H), 3.63 (t, J=6.5 Hz, 2H), 3.60-3.55 (m, 1H), 2.60 (dddd, J=14.0, 6.2, 4.3, 1.4 Hz, 1H), 2.30 (dtd, J=14.4, 8.6, 1.2 Hz, 1H), 2.25-2.17 (m, 2H), 2.01 (qd, J=7.3, 1.4 Hz, 2H), 1.59-1.49 (m, 2H), 1.48-1.37 (m, 5H), 1.34-1.29 (m, 4H), 0.89 (t, J=7.0 Hz, 3H).

$^{13}$C NMR (101 MHz, CDCl$_3$): δ 197.6, 160.9, 147.0, 135.4, 135.3, 132.6, 131.8, 125.8, 125.3, 62.9, 43.7, 33.6, 32.5, 31.5, 30.9, 28.6, 27.2, 25.8, 22.6, 14.2.

FTIR (ATR): 3445, 2960, 2930, 2862, 1690, 1629, 1580, 1447, 1264, 1207, 1054, 979, 732 cm$^{-1}$.

HRMS (TOF, ES$^+$, m/z): calc'd for C$_{20}$H$_{31}$O$_2$[M+H]$^+$ 303.2319, found: 303.2320.

[α]$^D_{23}$: +115.8° (c=0.5, CHCl$_3$).

HPLC Conditions: 10% IPA, 1.0 mL/min, Chiralcel OD-H column, λ=254 nm, tR (min): major=10.12, minor=13.57.

Example 4

Preparation of 15-deoxy-Δ$^{12,14}$-Prostaglandin J$_2$ (2)

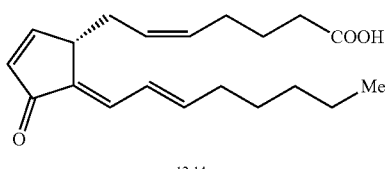

15-deoxy-Δ$^{12,14}$-prostaglandin J$_2$
(15d-PGJ$_2$)

To a stirred solution of 17 (14 mg, 0.046 mmol, 1.0 equiv) in MeCN (0.5 mL) was added NMO·H$_2$O (65 mg, 0.46 mmol, 10.0 equiv). Tetrapropylammonium perruthenate (1.7 mg. 4.6 µmol, 0.1 equiv) was added until NMO·H$_2$O was fully dissolved, and the reaction was stirred at 23° C. for 3 hours. The reaction mixture was stirred for 3 hours and the solvent was removed in vacuo. The residue was loaded onto a silica gel column, flushed with CH$_2$Cl$_2$ then CH$_2$Cl$_2$/MeOH (20:1). 15-deoxy-Δ$^{12,14}$-prostaglandin J$_2$ (2) was obtained as a colorless oil (10 mg, 68% yield).

TLC (100% EtOAc): Rf=0.70 (UV).

$^1$H NMR (400 MHz, CDCl$_3$): δ 7.47 (ddd, J=6.0, 2.6, 1.0 Hz, 1H), 6.95 (d. J=11.0 Hz, 1H), 6.38-6.35 (m, 1H), 6.33-6.20 (m, 2H), 5.50-5.33 (m, 2H), 3.59 (ddd, J=8.4, 4.1, 2.2 Hz, 1H), 2.59 (m, 1H), 2.36-2.19 (m, 5H), 2.05 (q, J=7.3 Hz, 2H), 1.68 (quint, J=7.5 Hz, 2H), 1.50-1.41 (m, 2H), 1.34-1.28 (m. 4H), 0.90 (t, J=7.0 Hz, 3H).

$^{13}$C NMR (101 MHz, CDCl$_3$): δ 197.6, 177.9, 160.8, 147.2, 135.5, 135.1, 131.9, 131.5, 126.2, 125.8, 43.6, 33.6, 33.2, 31.6, 30.8, 28.6, 26.7, 24.6, 22.6, 14.2.

FTIR (ATR): 2960, 2928, 2850, 1708, 1692, 1629, 1456, 1265, 1207, 978, 734, 703 cm$^{-1}$.

HRMS (TOF, ES$^+$, m/z): calc'd for C$_{20}$H$_{29}$O$_3$ [M+H]$^+$ 317.2111, found: 317.2127.

[α]$^D_{23}$: +106.2° (c=0.2, CHCl$_3$).

Spectral data ($^1$H NMR, $^{13}$C NMR, HRMS) matched with the published data:

Acharya, H. P.; Kobayashi, Y. Highly Efficient Total Synthesis of Δ12-PGJ$_2$, 15-Deoxy-Δ$^{12,14}$-PGJ$_2$, and Their Analogues. *Tetrahedron* 2006, 62, 3329-3343.

Brummond, K. M.; Sill. P. C.; Chen, H. The First Total Synthesis of 15-Deoxy-Δ$^{12,14}$-Prostaglandin J$_2$ and the Unambiguous Assignment of the C14 Stereochemistry. *Org. Lett.* 2004, 6, 149-152. Kim, N.-J.; Moon, H.; Park, T.; Yun, H.; Jung, J.-W.; Chang, D.-J.; Kim, D.-D.; Suh. Y.-G. Concise and Enantioselective Total Synthesis of 15-Deoxy-Δ$^{12,14}$-Prostaglandin J$_2$. *J. Org. Chem.* 2010, 75, 7458-7460. Egger, J.; Fischer, S.; Bretscher, P.; Freigang, S.; Kopf, M.; Carreira, E. M. Total Synthesis of Prostaglandin 15d-PGJ$_2$ and Investigation of Its Effect on the Secretion of IL-6 and IL-12. *Org. Lett.* 2015, 17, 4340-4343.

Example 5

Preparation of Alcohol 23 in the Presence of Ru-4

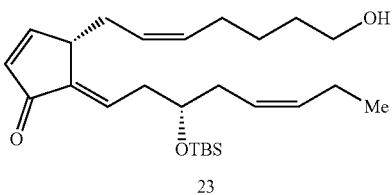 [SMILES: CC/C=C\C[C@@H](C/C=C1/C(=O)C=C[C@@H]1C/C=C\CCCCO)O[Si](C)(C)C(C)(C)C]

23

In a nitrogen-filled glovebox, cis-5-octen-1-ol (72 mg, 0.55 mmol, 6.7 equiv) was dissolved in toluene (1 mL) in a 50 mL Schlenk flask and a solution of catalyst Ru-4 (4.7 mg, 5.6 µmol, 1 mol %) in THF (0.6 mL) was added. The Schlenk flask was sealed and brought out of the glovebox, and then connected to high vacuum. The valve was gradually opened (Caution: open slowly and stir well to avoid splashing). After 15 minutes stirring, the flask was refilled with argon and sealed, and was brought back into the glovebox. The residue was diluted with 0.5 mL THF, and an aliquot was taken for GC analysis (conversion of homodimerization step was >98% by GC analysis). A solution of 22 [CAS 2254448-26-3] (30 mg, 0.083 mmol, 1 equiv) in 0.5 mL THF was added into the Schlenk flask and an additional 0.4 mL of catalyst solution with Ru-4 (2.9 mg, 3.5 µmol, 5 mol %) was added. The Schlenk flask was sealed and brought out of glovebox. The reaction was stirred for 12 h at 23° C. before a few drops of ethyl vinyl ether were added. The solvent was removed under reduced pressure. The residue was purified by flash chromatography (hexanes/EtOAc 10:1 to 2:1). 23 (16 mg. 44%) and 24 (8 mg, 31%) was isolated as two products.

Compound 23:

TLC (2:1 hexanes/EtOAc): Rf=0.28 (UV).

$^1$H NMR (400 MHz, CDCl$_3$) δ 7.50 (ddd, J=6.0, 2.7, 1.0 Hz, 1H), 6.60 (ddt, 8.2, 7.0, 1.3 Hz, 1H), 6.32 (dd, J=6.0, 1.8 Hz, 1H), 5.53-5.43 (m, 2H), 5.41-5.31 (m. 2H), 3.89 (quint, J=6.1 Hz. 1H), 3.64 (t, J=6.5 Hz, 2H), 3.45 (ddq, J=8.4, 4.3, 2.2 Hz, 1H). 2.68-2.55 (m, 1H), 2.43 (ddd, J=7.7, 6.4, 2.3 Hz, 2H), 2.29-2.11 (m, 3H), 2.08-1.91 (m, 4H), 1.62-1.51 (m, 2H), 1.48-1.36 (m, 2H), 0.94 (t, J=7.6 Hz, 3H), 0.88 (s, 9H), 0.06 (s, 3H), 0.05 (s, 3H).

$^{13}$C NMR (101 MHz, CDCl$_3$) δ 196.5, 161.8, 138.9, 135.0, 134.2, 132.7, 132.5, 125.5, 124.4, 71.7, 62.9, 43.6, 37.0, 35.3, 32.5, 30.8, 27.2, 26.0, 25.9, 20.9, 18.2, 14.3, −4.4, −4.4.

FTIR (ATR): 3429, 2956, 2928, 2856, 2361, 2327, 1702, 1652, 1580, 1472, 1360, 1251, 1213, 1066, 1005, 968, 834, 807, 774, 721, 668 cm$^{-1}$.

HRMS (FAB$^+$, m/z): calculated for C$_{26}$H$_{45}$O$_3$Si [M+H]$^+$ 433.3132. found: 433.3121.

[α]$^D_{23}$: +136.3° (c=1.0, C$_6$H$_6$).

Compound 24:

TLC (2:1 hexanes/EtOAc): Rf=0.6 (UV).

$^1$H NMR (400 MHz, CDCl$_3$): δ 7.43 (ddd, J=5.9, 2.8, 1.0 Hz, 1H), 6.80 (ddt, J=10.8, 8.8, 1.3 Hz, 1H), 6.31 (dd, J=5.9, 1.7 Hz, 1H), 5.76 (q, J=9.1 Hz. 1H), 5.61 (dddd, J=11.9, 10.7, 5.2, 1.2 Hz, 1H). 4.08-4.02 (m, 1H), 3.27 (d, 9.6 Hz, 1H), 2.38 (dd, J=9.5, 3.0 Hz, 210, 2.24 (q, J=11.6 Hz, 2H), 2.17-1.95 (m. 2H), 0.91 (s. 9H), 0.11 (s, 3H), 0.08 (s, 3H).

$^{13}$C NMR (101 MHz, CDCl$_3$): δ 196.4, 162.3, 141.3, 134.0, 132.4, 130.6, 129.6, 73.1, 44.2, 34.7, 34.5, 32.6, 26.0, 18.3, −4.6, −4.7.

FTIR (ATR): 2952, 2926, 2886, 2855, 2359, 2339, 1705, 1654, 1586, 1471, 1369, 1251, 1190, 1077, 1039, 997, 980, 938, 855, 835, 808, 790, 774, 727.668 cm$^{-1}$.

HRMS (FAB$^+$, m/z): calculated for C$_{18}$H$_{29}$O$_2$Si [M+H]$^+$ 305.1931, found: 305.1942.

[α]$^D_{23}$: −27.8° (c=0.8, CHCl$_3$)

Example 6

Preparation of Alcohol 23 in the Presence of Ru-2

In a nitrogen-filled glovebox, 22 (64 mg, 0.18 mmol, 1.0 equiv) and 5-hexen-1-ol (142 mg, 1.42 mmol, 8.0 equiv) were weighed into a 4 mL vial. THF (0.3 mL) was added to dissolve the mixture. Catalyst Ru-2 (24 mg, 20 mol %) was dissolved in THF (0.4 ml) and 0.1 mL of this catalyst solution was transferred into the vial. The vial was sealed with a 14/20 septum and brought out of the glovebox. The reaction was stirred at 40° C. with a stream of argon (saturated with anhydrous THF) bubbling through a needle. A portion of the catalyst solution (0.1 mL) was added into the vial in each 1 hour. After all the catalyst was added, the reaction mixture was continued to stir for 4 h with argon bubbling. A few drops of ethyl vinyl ether were added, and the reaction mixture was concentrated in vacuo. The residue was purified by column chromatography (SiO$_2$, hexanes/EtOAc 2:1) to afford 23 (40 mg, 52%) as a colorless liquid. Compound 26 was the proposed by-product (molar ratio of 23:26 was 32:1 as determined by crude NMR analysis).

Compound 23: Characterization data were in agreement with previously obtained data.

Compound 26: Characterization data not available due to the difficulty in separation, mass data was obtained by LC-MS (TOF, ES$^+$, m/z): calculated for C$_{24}$H$_{41}$O$_3$Si [M+H]$^+$ 405.2819, found: 405.2801.

Example 7

Preparation of Δ$^{12}$-Prostaglandin J$_3$ (3)

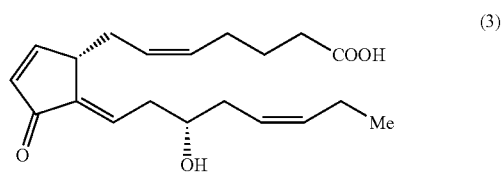

Δ$^{12}$-prostaglandin J$_3$
(Δ$^{12}$-PGJ$_3$)

(3)

To a stirred solution of 23 (21.6 mg, 0.05 mmol, 1.0 equiv) in MeCN (0.5 mL) was added NMO·H$_2$O (67.5 mg, 0.5 mmol, 10.0 equiv). Tetrapropylammonium perruthenate (1.8 mg, 5 µmol, 0.1 equiv) was added until NMO·H$_2$O was fully dissolved, and the reaction was stirred at 23° C. for 3 hours. The solution was diluted with Et$_2$O (5 mL), passed through a short pad of silica gel, concentrated and was subjected to the next reaction without further purification.

The residue was dissolved in MeCN (1.0 mL) and cooled to 0° C. A solution of hydrofluoric acid (48 wt. % in H$_2$O, 0.2 mL) in MeCN (0.4 mL) was added dropwisely. The solution was stirred in the same temperature for 30 min before saturated NaHCO$_3$ solution (1.5 mL) and brine (1.5 mL) were added. The aqueous phase was extracted with EtOAc (5×5 mL). The combined organic phase was dried over magnesium sulfate, filtered and concentrated (not to dryness). The residue was purified by flash chromatography (SiO$_2$, CH$_2$Cl$_2$/MeOH 20:1) and through BiotageR SNAP Ultra C$_{18}$ column (H$_2$O/MeOH) to give 3 (10 mg, 60% over 2 steps) as a colorless liquid.

TLC (100% EtOAc): Rf=0.55 (UV).

$^1$H NMR (400 MHz, CDCl$_3$): δ 7.58 (ddd, J=6.0, 2.6, 1.0 Hz, 1H), 6.57 (ddt, J=8.4, 7.0, 1.2 Hz, 1H), 6.36 (dd, J=6.0, 1.8 Hz, 1H), 5.69-5.60 (m, 1H), 5.60-5.45 (m, 2H), 5.45-5.35 (m, 1H), 3.91 (quint, J=6.8 Hz, 1H), 3.50-3.44 (m, 1H), 2.75 (ddd, J=13.9, 6.9, 4.4 Hz, 1H), 2.68-2.58 (m. 1H), 2.49 (ddd, J=15.2, 8.4, 7.0 Hz, 1H), 2.36 (t, J=6.8 Hz, 2H), 2.33-2.28 (m, 2H), 2.20-1.98 (m. 5H), 1.68 (quint, J=7.0 Hz, 2H), 0.96 (t, J=7.5 Hz, 3H).

$^{13}$C NMR (101 MHz, CDCl$_3$): δ 196.4, 175.8, 161.8, 139.9, 136.4, 135.1, 131.7, 131.2, 126.3, 123.6, 71.1, 44.0, 36.3, 34.5, 32.9, 30.7, 26.6, 24.7, 20.9, 14.4.

FTIR (ATR): 3449, 3010, 2956, 2919, 2850, 1728, 1703, 1650, 1579, 1455, 1375, 1222, 1182, 1046, 959, 838, 809, 721 cm$^{-1}$.

HRMS (FAB$^+$, m/z): calc'd for C$_{20}$H$_{29}$O$_4$ [M+H]$^+$ 333.2060, found: 333.2060.

$[\alpha]^P_{23}$: +122.6° (c=0.5, C$_6$H$_6$).

Spectral data ($^1$H NMR, $^{13}$C NMR, HRMS) matched with the published data.6 Comparisons of $^1$H NMR data of natural and synthetic Δ$^{12}$-prostaglandin J$_3$ (3) are listed in Table S2 of *J. Am. Chem. Soc.,*

Example 8

Preparation of Alcohol 29 in the Presence of Ru-4

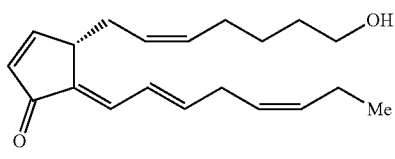

29

In a nitrogen-filled glovebox, cis-5-octen-1-ol (205 mg, 1.6 mmol. 8.0 equiv) was dissolved in toluene (I mL) in a 50 mL Schlenk flask and a solution of catalyst Ru-4 (13.6 mg, 16 μmol, 1 mol %) in THF (0.6 mL) was added. The Schlenk flask was sealed and brought out of the glovebox, and then connected to high vacuum. The valve was gradually opened (Caution: open slowly and stir well to avoid splashing). After 15 minutes stirring, the flask was refilled with argon and sealed, and was brought back into the glovebox. The residue was diluted with 0.5 mL THF, and an aliquot was taken for GC analysis (conversion of homodimerization step was >98% by GC analysis). A solution of 28 [CAS 2254448-29-6] (46 mg, 0.2 mmol, 1.0 equiv) in 0.5 mL THF was added into the Schlenk flask and an additional 0.4 mL of catalyst solution with Ru-4 (8.5 mg, 10 μmol, 5 mol %) was added. The Schlenk flask was sealed and brought out of glovebox. The reaction was stirred for 12 h at 23° C. before a few drops of ethyl vinyl ether were added. The solvent was removed under reduced pressure. The residue was purified by column chromatography (SiO$_2$, hexanes/EtOAc 2:1). Compounds 29 (22 mg, 36%) and 30 were separated as a mixture (28 mg, molar ratio of 29:30 was 3:1 as determined by crude NMR analysis).

Compound 29: Characterization data not available due to the difficulty in separation.

Mass data was obtained by LC-MS (TOF. ES$^+$, m/z): calc'd for C$_{20}$H$_{29}$O$_2$ [M+H]$^+$ 301.2162, found: 301.2080.

Compound 30: Characterization data not available due to the difficulty in separation, mass data was obtained by LC-MS (TOF, ES$^+$, m/z): calculated for C$_{18}$H$_{25}$O$_2$ [M+H]$^+$ 273.1849, found: 273.1759.

Example 9

Preparation of Alcohol 29 in the Presence of Ru-2

In a nitrogen-filled glovebox, 28 (23 mg, 0.1 mmol, 1.0 equiv) and 5-hexen-1-ol (80 mg, 0.8 mmol, 8.0 equiv) were weighed into a 4 mL vial. THF (0.1 mL) was added to dissolve the mixture. Catalyst Ru-2 (13.6 mg, 20 mol %) was dissolved in THF (0.4 mL) and 0.1 mL of this catalyst solution was transferred into the vial. The vial was sealed with a 14/20 septum and brought out of the glovebox. The reaction was stirred at 40° C. with a stream of argon (saturated with anhydrous THF) bubbling through a needle. A portion of the catalyst solution (0.1 mL) was added into the vial in each 1 hour. After all the catalyst was added, the reaction mixture was continued to stir for 2 h with argon bubbling. A few drops of ethyl vinyl ether were added, and the reaction mixture was concentrated in vacuo. The residue was purified by column chromatography (SiO$_2$, hexanes/EtOAc 2:1). Compounds 29 (9.2 mg, 31%) and 30 were separated as a mixture (12 mg, molar ratio of 29:30 was 3:1 as determined by crude NMR analysis).

Compound 29: Characterization data not available due to the difficulty in separation. Mass data was obtained by LC-MS (TOF, ES$^+$, m/z): calc'd for C$_{18}$H$_{25}$O$_2$[M+H]$^+$ 273.1849, found: 273.1855.

Example 10

Preparation of 15-deoxy-Δ$^{124}$-Prostaglandin J$_3$ (4) from 29

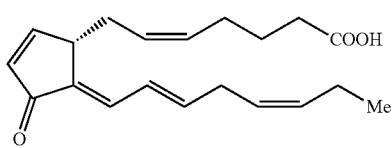

(4)

15-deoxy-Δ$^{12,14}$-prostaglandin J$_3$
(15d-PGJ$_3$)

Pyridinium chlorochromate (22 mg, 0.1 mmol, 3.0 equiv) was added to a solution of 29 (mixed with by-product 30) (10 mg, 0.033 mmol, 1.0 equiv) in CH$_2$Cl$_2$ (0.5 mL) at 23° C. The reaction was monitored by TLC and was diluted with Et$_2$O (3 mL) after stirring for 3 h. The resulting solution was filtered through a short pad of silica gel and was subjected to the next step without further purification. The residue was dissolved in t-BuOH (0.5 mL) at 23° C., and 2-methyl-2-butene (35 μL, 0.33 mmol, 10 equiv), a solution of NaH$_2$PO$_4$·H$_2$O (6.9 mg, 0.05 mmol, 1.5 equiv) in H$_2$O (0.12 mL) and a solution of NaClO$_2$ (80%, 5.6 mg, 0.05 mmol, 1.5 equiv) in H$_2$O (0.12 ml) was added sequentially. After stirring at 23° C. for 30 minutes, the reaction mixture was diluted with a solution of NaH$_2$PO$_4$·H$_2$O (108 mg) in H$_2$O (2 mL) and extracted with EtOAc (5×5 mL). The combined organic extracts were dried over anhydrous magnesium sulfate, filtered, and concentrated under reduced pressure.

Flash column chromatography (SiO$_2$, CH$_2$Cl$_2$/MeOH 20:1) and purification through BiotageR SNAP Ultra C18 column (H$_2$O/MeOH) afforded pure compound 4 (4 mg, 0.013 mmol, 12% yield from 28) as a colorless oil.

TLC (10:1 CH$_2$Cl$_2$/MeOH): Rf=0.44 (UV).

$^1$H NMR (500 MHz, CDCl$_3$): δ 7.48 (ddd, J=6.1, 2.6, 1.0 Hz, 1H), 6.96 (d, J=11.5 Hz, 1H), 6.42-6.31 (m, 2H), 6.22 (dt, J=14.9, 6.3 Hz, 1H), 5.57-5.51 (m, 1H), 5.50-5.43 (m, 1H), 5.37 (dtt, J=10.1, 6.8, 1.7 Hz, 2H), 3.64-3.55 (m, 1H), 2.98 (t, J=6.8 Hz, 2H), 2.60 (dt, J=12.3, 5.9 Hz, 1H), 2.43-2.25 (m, 3H), 2.12-2.00 (m, 4H), 1.69 (quint, J=7.4 Hz, 2H), 0.99 (t, J=7.5 Hz, 3H).

$^{13}$C NMR (101 MHz, CDCl$_3$): δ 197.6, 176.6, 160.9, 144.5, 135.5, 135.5, 134.2, 131.6, 131.5, 126.1, 125.8, 124.6, 43.6, 33.0, 31.2, 30.9, 26.7, 24.6, 20.7, 14.3.

FTIR (ATR): 3010, 2960, 2926, 2874, 2854, 1710, 1693, 1626, 1578, 1512, 1455, 1208, 1154, 1087, 1024, 977, 817, 728 cm$^{-1}$.

HRMS (FAB+, m/z): calc'd for C$_{20}$H$_{27}$O$_3$ [M+H]$^+$ 315.1955, found: 315.1968.

[α]$^D_{23}$: +129.6° (c=0.07, C$_6$H$_6$).

Spectral data ($^1$H NMR, $^{13}$C NMR, HRMS) matched with the published data:

Nicolaou, K. C.; Pulukuri, K. K.; Rigol, S.; Heretsch. P.; Yu, R.; Grove, C. I.; Hale, C. R. H.; ElMarrouni, A.; Fetz, V.; Bronstrup, M.; Aujay M.; Sandoval J.; Gavrilyuk J. Synthesis and Biological Investigation of Δ$^{12}$-Prostaglandin J$_3$ (Δ$^{12}$-PGJ$_3$) Analogues and Related Compounds. *J. Am. Chem. Soc.* 2016, 138, 6550-6560.

What is claimed is:

1. A method for producing at least one Δ$^{12}$-Prostaglandin J product represented by Formula (IV),

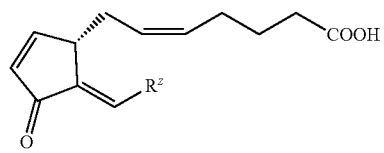

Formula (IV)

wherein: R$^z$ is selected from

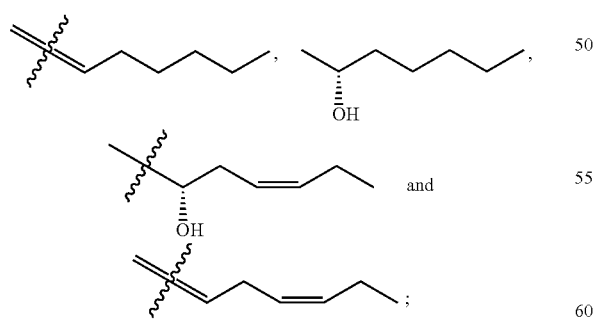

and wherein at least one carbon-carbon double bond has a Z/E-selectivity of 95/5, or 96/4, or 97/3, or 98/2, or 99/1, or >99/<1;

comprising, submitting an alcohol product of Formula (III)

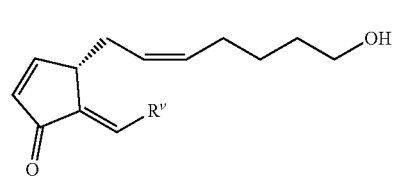

Formula (III)

to oxidation conditions; wherein the alcohol product of Formula (III) is formed during a cross-metathesis reaction between a substrate represented by Formula (II)

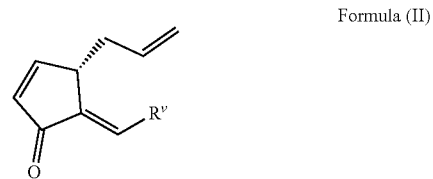

Formula (II)

and cis-5-octen-1-ol in the presence of a ruthenium olefin metathesis catalyst; and wherein R$^v$ is selected from

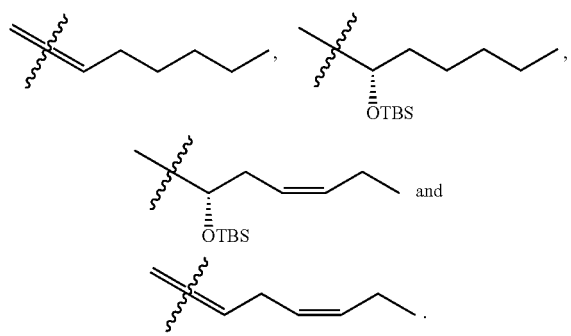

2. The method according to claim 1, wherein the ruthenium catalyst is a stereoretentive ruthenium olefin metathesis catalyst represented by Formula (I) is

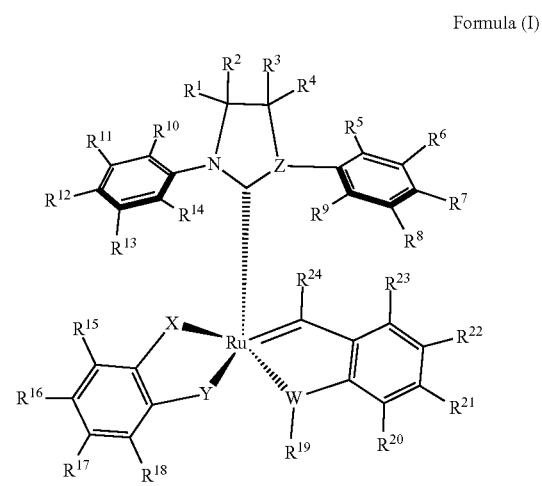

Formula (I)

X is O or S;
Y is O or S;
Z is N or $CR^{32}$;
W is O, halogen, $NR^{33}$ or S;
$R^1$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;

$R^2$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;

$R^3$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;

$R^4$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;

$R^5$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;

$R^6$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;

$R^7$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;

$R^8$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;

$R^9$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;

$R^{10}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ can form an optionally substituted polycyclic ring;

$R^{11}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{10}$ or together with $R^{12}$ can form an optionally substituted polycyclic ring;

$R^{12}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{11}$ or together with $R^{13}$ can form an optionally substituted polycyclic ring;

$R^{13}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{14}$ or together with $R^{12}$ can form an optionally substituted polycyclic ring;

$R^{14}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{13}$ can form a polycyclic ring;

$R^{15}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{16}$ can form an optionally substituted polycyclic ring;

$R^{16}$ is H, optionally substituted $C_{1-24}$ alkyl, halogen, $-C(O)R^{25}$, $-OR^{26}$, CN, $-NR^{27}R^{28}$, $NO_2$, $-CF_3$, $-S(O)_xR^{29}$, $-P(O)(OH)_2$, $-OP(O)(OH)_2$, $-SR^{31}$, optionally substituted heterocycle, optionally substituted $C_{3-8}$ cycloalkyl, optionally substituted $C_{5-24}$ aryl or optionally substituted $C_{3-8}$ cycloalkenyl, or together with $R^{15}$ or together with $R^{17}$ can form an optionally substituted polycyclic ring;

$R^{17}$ is H, optionally substituted $C_{1-24}$ alkyl, halogen, $-C(O)R^{25}$, $-OR^{26}$, CN, $-NR^{27}R^{28}$, $NO_2$, $-CF_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl, or together with R$^{18}$ or together with R$^{16}$ can form an optionally substituted polycyclic ring;

R$^{18}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl, or together with R$^{17}$ can form an optionally substituted polycyclic ring;

R$^{19}$ is H, optionally substituted C$_{1-24}$ alkyl, —C(R$^{34}$)(R$^{35}$)COOR$^{36}$, —C(R$^{34}$)(R$^{35}$)C(O)H, —C(R$^{34}$)(R$^{35}$)C(O)R$^{37}$, —C(R$^{34}$)(R$^{35}$)CR$^{38}$(OR$^{39}$)(OR$^{40}$), —C(R$^{34}$)(R$^{35}$)C(O)NR$^{41}$R$^{42}$, —C(R$^{34}$)(R$^{35}$)C(O)NR$^{41}$OR$^{40}$, —C(O)R$^{25}$, optionally substituted heterocycle, optionally substituted C$_{3-8}$ cycloalkyl, optionally substituted C$_{5-24}$ aryl, optionally substituted C$_{3-8}$ cycloalkenyl, or together with R$^{33}$ can form an optionally substituted heterocyclic ring or is nil when W is halogen;

R$^{20}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{21}$ can form a polycyclic ring;

R$^{21}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{20}$ or together with R$^{22}$ can form a polycyclic ring;

R$^{22}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{21}$ or together with R$^{23}$ can form a polycyclic ring;

R$^{23}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl, optionally substituted C$_{3-8}$ cycloalkenyl or together with R$^{22}$ can form a polycyclic ring;

R$^{24}$ is H, optionally substituted C$_{1-24}$ alkyl, halogen, —C(O)R$^{25}$, —OR$^{26}$, CN, —NR$^{27}$R$^{28}$, NO$_2$, —CF$_3$, —S(O)$_x$R$^{29}$, —P(O)(OH)$_2$, —OP(O)(OH)$_2$, —SR$^{31}$, optionally substituted heterocycle, optionally substituted C$_{3-8}$ cycloalkyl, optionally substituted C$_{5-24}$ aryl or optionally substituted C$_{3-8}$ cycloalkenyl;

R$^{25}$ is OH, OR$^{30}$, NR$^{27}$R$^{28}$, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl, R$^{26}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{27}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{28}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{29}$ is H, optionally substituted C$_{1-24}$ alkyl, OR$^{26}$, —NR$^{27}$R$^{28}$, optionally substituted heterocycle, optionally substituted C$_{3-8}$ cycloalkyl, optionally substituted C$_{5-24}$ aryl or optionally substituted C$_{3-8}$ cycloalkenyl;

R$^{30}$ is optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{31}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{32}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{33}$ is H, optionally substituted C$_{1-24}$ alkyl, optionally substituted C$_{3-8}$ cycloalkyl, optionally substituted heterocycle, optionally substituted C$_{5-24}$ aryl, optionally substituted C$_{3-8}$ cycloalkenyl, or together with R$^{19}$ can form an optionally substituted heterocyclic ring;

R$^{34}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{35}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{36}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{37}$ is optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{38}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{39}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{40}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{41}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl;

R$^{42}$ is H, optionally substituted C$_{1-24}$ alkyl, optionally substituted C$_{3-8}$ cycloalkyl, optionally substituted heterocycle, optionally substituted C$_{5-24}$ aryl or optionally substituted C$_{3-8}$ cycloalkenyl; and x is 1 or 2.

3. The method according to claim 1, wherein the ruthenium catalyst is a Z-selective ruthenium olefin metathesis catalyst represented by Formula (V) is

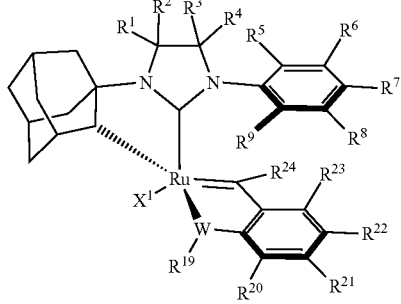

Formula (V)

wherein:
W is O, halogen, $NR^{33}$ or S;
$X^1$ is hydrogen, halide, nitrate, optionally substituted $C_1$-$C_{20}$ alkyl, optionally substituted $C_5$-$C_{24}$ aryl, optionally substituted $C_1$-$C_{20}$ alkoxy, optionally substituted $C_1$-$C_{20}$ alkylcarboxylate, optionally substituted $C_5$-$C_{24}$ aryloxy, optionally substituted $C_2$-$C_{20}$ alkoxycarbonyl, optionally substituted $C_6$-$C_{24}$ aryloxycarbonyl, optionally substituted $C_6$-$C_{24}$ arylcarboxylate, optionally substituted $C_2$-$C_{24}$ acyl, optionally substituted $C_2$-$C_{24}$ acyloxy, optionally substituted $C_1$-$C_{20}$ alkylsulfonato, optionally substituted $C_5$-$C_{24}$ arylsulfonato, optionally substituted $C_1$-$C_{20}$ alkylsulfanyl, optionally substituted $C_5$-$C_{24}$ arylsulfanyl, optionally substituted $C_1$-$C_{20}$ alkylsulfinyl, or optionally substituted $C_5$-$C_{24}$ arylsulfinyl;
$R^1$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^2$ can form a spiro compound or together with $R^3$ or together with $R^4$ can form a polycyclic ring;
$R^2$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^1$ can form a spiro compound or together with $R^3$ or together with $R^4$ can form a polycyclic ring;
$R^3$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl or optionally substituted $C_{3-8}$ cycloalkenyl or together with $R^2$ or together with $R^1$ can form a polycyclic ring or together with $R^4$ can form a spiro compound;
$R^4$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^3$ can form a spiro compound or together with $R^2$ or together with $R^1$ can form a polycyclic ring;
$R^5$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^6$ can form an optionally substituted polycyclic ring;
$R^6$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^5$ or together with $R^7$ can form an optionally substituted polycyclic ring;
$R^7$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl optionally substituted $C_{3-8}$ cycloalkenyl, or together with $R^6$ or together with $R^8$ can form an optionally substituted polycyclic ring;
$R^8$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^7$ or together with $R^9$ can form an optionally substituted polycyclic ring;
$R^9$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^8$ can form an optionally substituted polycyclic ring;
$R^{19}$ is H, optionally substituted $C_{1-24}$ alkyl, —C($R^{34}$)($R^{35}$)COO$R^{36}$, —C($R^{34}$)($R^{35}$)C(O)H, —C($R^{34}$)($R^{35}$)C(O)$R^{37}$, —C($R^{34}$)($R^{35}$)C$R^{38}$(O$R^{39}$)(O$R^{40}$), —C($R^{34}$)($R^{35}$)C(O)N$R^{41}R^{42}$, —C($R^{34}$)($R^{35}$)C(O)N$R^{41}$O$R^{40}$, —C(O)$R^{25}$, optionally substituted heterocycle, optionally substituted $C_{3-8}$ cycloalkyl, optionally substituted $C_{5-24}$ aryl, optionally substituted $C_{3-8}$ cycloalkenyl, or together with $R^{33}$ can form an optionally substituted heterocyclic ring or is nil when W is halogen;
$R^{20}$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ can form a polycyclic ring;
$R^{21}$ is H, optionally substituted $C_{1-24}$ alkyl, halogen, —C(O)$R^{25}$, —O$R^{26}$, CN, —N$R^{27}R^{28}$, $NO_2$, —$CF_3$, —S(O)$_xR^{29}$, —P(O)(OH)$_2$, —OP(O)(OH)$_2$, —$SR^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{20}$ or together with $R^{22}$ can form a polycyclic ring;

$R^{22}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{21}$ or together with $R^{23}$ can form a polycyclic ring;

$R^{23}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl, optionally substituted $C_{3-8}$ cycloalkenyl or together with $R^{22}$ can form a polycyclic ring;

$R^{24}$ is H, optionally substituted $C_{1-24}$ alkyl, halogen, —C(O)$R^{25}$, —O$R^{26}$, CN, —N$R^{27}R^{28}$, NO$_2$, —CF$_3$, —S(O)$_x R^{29}$, —P(O)(OH)$_2$, —OP(O)(OH)$_2$, —S$R^{31}$, optionally substituted heterocycle, optionally substituted $C_{3-8}$ cycloalkyl, optionally substituted $C_{5-24}$ aryl or optionally substituted $C_{3-8}$ cycloalkenyl;

$R^{25}$ is OH, O$R^{30}$, N$R^{27}R^{28}$, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl, $R^{26}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{27}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{28}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{29}$ is H, optionally substituted $C_{1-24}$ alkyl, O$R^{26}$, —N$R^{27}R^{28}$, optionally substituted heterocycle, optionally substituted $C_{3-8}$ cycloalkyl, optionally substituted $C_{5-24}$ aryl or optionally substituted $C_{3-8}$ cycloalkenyl;

$R^{30}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{31}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{32}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{33}$ is H, optionally substituted $C_{1-24}$ alkyl, optionally substituted $C_{3-8}$ cycloalkyl, optionally substituted heterocycle, optionally substituted $C_{5-24}$ aryl, optionally substituted $C_{3-8}$ cycloalkenyl, or together with $R^{19}$ can form an optionally substituted heterocyclic ring;

$R^{34}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{35}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{36}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{37}$ is optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{38}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{39}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{40}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{41}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl;

$R^{42}$ is H, optionally substituted $C_{1-24}$ alkyl, optionally substituted $C_{3-8}$ cycloalkyl, optionally substituted heterocycle, optionally substituted $C_{5-24}$ aryl or optionally substituted $C_{3-8}$ cycloalkenyl; and x is 1 or 2.

4. The method according to claim 1, wherein the oxidation takes place in the presence of tetrapropylammonium perruthenate and 4-methylmorpholine N-oxide monohydrate.

5. The method according to claim 1, wherein the oxidation takes place in the presence of pyridinium chlorochromate and sodium chlorite.

6. The method according to claim 4, wherein $R^z$ is

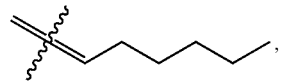 [SMILES: *=CCCCCC], $R^v$ is

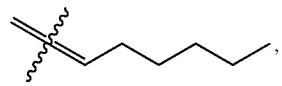 [SMILES: *=CCCCCC], and the ruthenium catalyst is a stereoretentive catalyst represented by Formula (I) wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

7. The method according to claim 4, wherein $R^z$ is

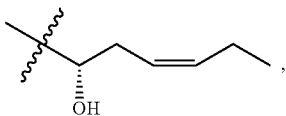 [SMILES: *[C@@H](O)C/C=C\CC], $R^v$ is

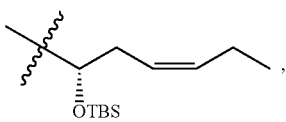 [SMILES: *[C@H](C/C=C\CC)O[Si](C)(C)C(C)(C)C], and the ruthenium catalyst is a Z-selective catalyst represented by Formula (V) wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is H; $R^{22}$ is H; $R^{23}$ is H; $R^{24}$ is H.

8. The method according to claim 5, wherein $R^z$ is

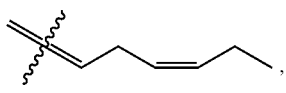 [SMILES: *=CC/C=C\CC], $R^v$ is

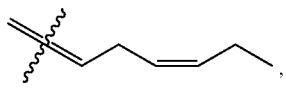 [SMILES: *=CC/C=C\CC], and the ruthenium catalyst is a stereoretentive catalyst represented by Formula (I) wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

9. The method according to claim 5, wherein $R^z$ is

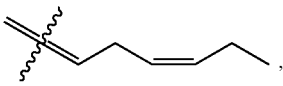 [SMILES: *=CC/C=C\CC], $R^v$ is

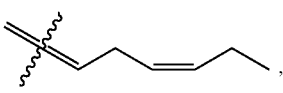 [SMILES: *=CC/C=C\CC], and the ruthenium catalyst is a Z-selective catalyst represented by Formula (V) wherein W is O; $X^1$ is nitrate; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{19}$ is i-Pr; $R^{20}$ is H; $R^{21}$ is —; H $R^{22}$ is H; $R^{23}$ is H; $R^{24}$ is H.

10. The method according to claim 5, wherein $R^z$ is

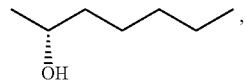, $R^v$ is

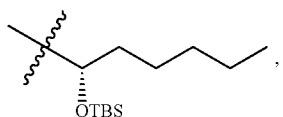 [SMILES: *[C@H](CCCCC)O[Si](C)(C)C(C)(C)C], and the ruthenium catalyst is a stereoretentive catalyst represented by Formula (I) wherein: X is S; Y is S; Z is N; W is O; $R^1$ is H; $R^2$ is H; $R^3$ is H; $R^4$ is H; $R^5$ is i-Pr; $R^6$ is H; $R^7$ is H; $R^8$ is H; $R^9$ is i-Pr; $R^{10}$ is i-Pr; $R^{11}$ is H; $R^{12}$ is H; $R^{13}$ is H; $R^{14}$ is i-Pr; $R^{15}$ is Cl; $R^{16}$ is H; $R^{17}$ is H; $R^{18}$ is Cl; $R^{19}$ is i-Pr; $R^{20}$ is H; $R^{21}$ is H; $R^{22}$ is H; $R^{23}$ is H; and $R^{24}$ is H.

* * * * *